United States Patent
Hebrok et al.

(10) Patent No.: US 11,299,711 B2
(45) Date of Patent: Apr. 12, 2022

(54) PRODUCTION OF FULLY FUNCTIONAL MATURE BETA CELLS FROM HUMAN PANCREATIC PROGENITORS

(71) Applicant: THE REGENTS OF THE UNIVERSITY OF CALIFORNIA, Oakland, CA (US)

(72) Inventors: Matthias Hebrok, Belmont, CA (US); Holger Andreas Russ, San Francisco, CA (US); Gopika G. Nair, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 398 days.

(21) Appl. No.: 16/092,166

(22) PCT Filed: Apr. 7, 2017

(86) PCT No.: PCT/US2017/026651
§ 371 (c)(1),
(2) Date: Oct. 8, 2018

(87) PCT Pub. No.: WO2017/177163
PCT Pub. Date: Oct. 12, 2017

(65) Prior Publication Data
US 2019/0177697 A1    Jun. 13, 2019

Related U.S. Application Data

(60) Provisional application No. 62/463,561, filed on Feb. 24, 2017, provisional application No. 62/320,185, filed on Apr. 8, 2016.

(51) Int. Cl.
| | |
|---|---|
| *C12N 5/071* | (2010.01) |
| *A61K 35/39* | (2015.01) |
| *A61K 35/545* | (2015.01) |
| *A61P 5/48* | (2006.01) |
| *A61P 3/10* | (2006.01) |

(52) U.S. Cl.
CPC ............ *C12N 5/0678* (2013.01); *A61K 35/39* (2013.01); *A61K 35/545* (2013.01); *A61P 3/10* (2018.01); *A61P 5/48* (2018.01); *C12N 5/0676* (2013.01); *C12N 2500/25* (2013.01); *C12N 2501/11* (2013.01); *C12N 2501/117* (2013.01); *C12N 2501/15* (2013.01); *C12N 2501/16* (2013.01); *C12N 2501/195* (2013.01); *C12N 2501/395* (2013.01); *C12N 2501/415* (2013.01); *C12N 2501/727* (2013.01); *C12N 2501/999* (2013.01); *C12N 2506/02* (2013.01); *C12N 2535/00* (2013.01)

(58) Field of Classification Search
CPC .................................................. C12N 5/0678
See application file for complete search history.

(56) References Cited

U.S. PATENT DOCUMENTS

| | | | |
|---|---|---|---|
| 2010/0112691 A1 | 5/2010 | Green et al. | |
| 2013/0164787 A1 | 6/2013 | Agulnick et al. | |
| 2015/0104430 A1 | 4/2015 | Keller et al. | |
| 2015/0329828 A1* | 11/2015 | Rezania | C12N 5/0676 |
| | | | 435/377 |

FOREIGN PATENT DOCUMENTS

| | | |
|---|---|---|
| WO | WO 2014/105543 | 7/2014 |
| WO | WO 2015/002724 | 1/2015 |
| WO | WO-2015/002724 A2 | 1/2015 |
| WO | WO-2016/172564 A1 | 10/2016 |
| WO | WO 2017/019702 | 2/2017 |

OTHER PUBLICATIONS

Holger et al.—IDS Feb. 28, 2019 (Year: 2015).*
Russ et al. (ePUB Apr. 23, 2015, The EMBO J., vol. 34(13), pp. 1759-1772) (Year: 2015).*
Pagliuca et al. (2014, Cell, vol. 159, pp. 428-439). (Year: 2014).*
European Search Report from Application No. 17779928.5 dated Sep. 24, 2019.
Kumar et al., "Recent Developments in β-Cell Differentiation of Pluripotent Stem Cells Induced by Small and Large Molecules," Int. J. Mol. Sci. 15:23418-23447 (2014).
Adewala et al., "Microfluidic perifusion and imaging device for multi-parametric islet function assessment," Biomed. Microdevices 12:409-417 (2010.
Aguayo-Mazzucato et al., "Mafa expression enhances glucose-responsive insulin secretion in neonatal rat beta cells," Diabetologia, 54(3):583-593 (2011).
Arda et al., "Age-Dependent Pancreatic Gene Regulation Reveals Mechanisms Governing Human? Cell Function," Cell Metabolism 23(5):909-920 (2016).
Bader et al., "Identification of proliferative and mature ?-cells in the islets of Langerhans," Nature 535(7612)430-434 (2016).
Barton et al., "Improvement in Outcomes of Clinical Islet Transplantation: 1999-2010," Diabetes Care 35:1436-1445(2012).
Blum et al., "Functional beta-cell maturation is marked by an increased glucose threshold and by expression of urocortin 3," Nat Biotech 30(3):261-264 (2012).
Borden et al., "Sympathetic Innervation during Development Is Necessary for Pancreatic Islet Architecture and Functional Maturation," Cell Reports 4(2):287-301 (2013).

(Continued)

*Primary Examiner* — Thaian N. Ton
*Assistant Examiner* — David A Montanari
(74) *Attorney, Agent, or Firm* — Marshall, Gerstein & Borun LLP

(57) ABSTRACT

Methods are provided for the simple, fast, effective and safe directed differentiation of embryonic stem cells into the mature beta cells of enriched beta clusters, wherein the beta cells rapidly and reliably secrete insulin in response to glucose levels. The cells are useful transplant therapeutics for diabetic individuals. These cells can also be used for drug screening purposes to identify factors/chemicals capable of increasing beta cell functions, proliferation, survival, and resistance to immune assault.

14 Claims, 40 Drawing Sheets

Specification includes a Sequence Listing.

(56) References Cited

OTHER PUBLICATIONS

Bouwens et al., "The use of stem cells for pancreatic regeneration in diabetes mellitus," Nat Rev Endocrinol 9:598-606 (2013).
Cabrera et al, "The unique cytoarchitecture of human pancreatic islets has implications for islet cell function," Proc. Natl. Acad. Sci. U.S.A. 103:2334-2339 (2006).
Chen et al., "A small molecule that directs differentiation of human ESCs into the pancreatic lineage," Nat. Chem. Biol. 5:258-265 (2009).
Cogliati et al., "Mitochondrial Cristae: Where Beauty Meets Functionality," Trends in Biochemical Sciences 41(3):261-273 (2016).
D'Amour et al., "Efficient differentiation of human embryonic stem cells to definitive endoderm," Nat. Biotechnol. 23: 1534-1541 (2005).
D'Amour et al., "Production of pancreatic hormone-expressing endocrine cells from human embryonic stem cells," Nat. Biotechnol. 24:1392-1401 (2006).
Dai et al., "Islet-enriched gene expression and glucose-induced insulin secretion in human and mouse islets," Diabetologia 55(3)707-718 (2012).
De Krijger et al., "The midgestational human fetal pancreas contains cells coexpressing islet hormones," Developmental Biology 153:368-375 (1992).
Dhawan et al., "DNA methylation directs functional maturation of pancreatic β cells," The Journal of Clinical Investigation 125(7):p. 2851-2860 (2015).
Dorrell et al., "Human islets contain four distinct subtypes of β cells," Nature Communications 7:11756 (2016).
Dorrell et al., "Transcriptomes of the major human pancreatic cell types," Diabetologia 54(11)2832-2844 (2011).
Ediger et al., "Islet-1 Is Essential for Pancreatic β-Cell Function. Diabetes," 63(12):4206-4217 (2014).
Efrat et al., "Making β cells from adult tissues," Trends in Endocrinology & Metabolism 23:278-285 (2012).
Fiaschi-Taesch et al., "Induction of Human-Cell Proliferation and Engraftment Using a Single G1/S Regulatory Molecule, cdk6," Diabetes 59:1926-1936 (2010).
Gosmain et al., "Pax6 Is Crucial for β-Cell Function, Insulin Biosynthesis, and Glucose Induced Insulin Secretion," Molecular Endocrinology, 26(4):696-709 (2012).
Gregg et al., "Formation of a Human β-Cell Population within Pancreatic Islets Is Set Early in Life," The Journal of Clinical Endocrinology & Metabolism, 97(9):3197-3206 (2012).
Gu et al., "Direct evidence for the pancreatic lineage: NGN3+ cells are islet progenitors and are distinct from duct progenitors," Development 129:2447-2457 (2002).
Gu et al., "Pancreatic β Cells Require NeuroD to Achieve and Maintain Functional Maturity," Cell Metabolism 11(4): 298-310 (2010).
Guo et a., "Inactivation of specific β cell transcription factors in type 2 diabetes," J. Clin. Invest. 123:3305-3316 (2013).
Guo et al., "Factors Expressed by Murine Embryonic Pancreatic Mesenchyme Enhance Generation of Insulin-Producing Cells From hESCs," Diabetes 62:1581-1592 (2013).
Haataja et al., "Proinsulin intermolecular interactions during secretory trafficking in pancreatic β cells," Journal of Biological Chemistry 288:1896-1906 (2013).
Hawdon et al., "The role of pancreatic insulin secretion in neonatal glucoregulation. I. Healthy term and preterm infants," Archives of Disease in Childhood 68:274-279 (1993).
Hebrok, "Generating β Cells from Stem Cells—the Story so Far," Cold Spring Harb Perspect Med 2: a007674 (2012).
Hebrok, "Hedgehog signaling in pancreas development," Mech. Dev. 120:45-57 (2003).
Hellerström et al., "Functional Maturation and Proliferation of Fetal Pancreatic ?-Cells," Diabetes 40(Supplement 2):89-93 (1991).
Henquin et al., "Dynamics and Regulation of Insulin Secretion in Pancreatic Islets from Normal Young Children," PLoS One, 11(11):e0165961 (2016).
Herrera et al,. "Pancreatic cell lineage analyses in mice," Endocrine 19:267-278 (2002).
Hua et al., "iPSC-derived β cells model diabetes due to glucokinase deficiency," J. Clin. Invest 123(7):3146-3153 (2013).
International Search Report and Written Opinion from International Application No. PCT/US2017/026651 dated Oct. 12, 2017.
Jacovetti et al., "Postnatal β-cell maturation is associated with islet-specific microRNA changes induced by nutrient shifts at weaning," Nature Communications 6:8084, 14 pages (2015).
Jennings et al., "Development of the human pancreas from foregut to endocrine commitment," Diabetes 62:3514-3522 (2013).
Jeon et al., "Endocrine cell clustering during human pancreas development," J Histochem Cytochem, 57:811-824 (2009).
Jermendy et al., "Rat neonatal beta cells lack the specialised metabolic phenotype of mature beta cells," Diabetologia 54(3):594-604 (2011).
Johansson et al., "Temporal control of neurogenin3 activity in pancreas progenitors reveals competence windows for the generation of different endocrine cell types," Developmental Cell 12:457-465 (2007).
Kaye et al., "The response of blood glucose, ketones, and plasma nonesterified fatty acids to fasting and epinephrine injection in infants and children," The Journal of Pediatrics 59(6):836-847 (1961).
Kelly et al., "Cell-surface markers for the isolation of pancreatic cell types derived from human embryonic stem cells," Nat. Biotechnol. 29:750-756 (2011).
Konstantinova et al., "EphA-Ephrin-A-Mediated β Cell Communication Regulates Insulin Secretion from Pancreatic Islets," Cell 129(2):359-370 (2011).
Kroon et al., "Pancreatic endoderm derived from human embryonic stem cells generates glucose-responsive insulin-secreting cells in vivo," Nat. Biotechnol. 26:443-452 (2008).
Lehmann et al., Superiority of small islets in human islet transplantation, Diabetes, 56(3):594-603 (2007).
Lemaire et al., "Disallowed and Allowed Gene Expression: Two Faces of Mature Islet Beta Cells," Annual Review of Nutrition 36(1):45-71 (2016).
Liu et al., "Systematically labeling developmental stage-specific genes for the study of pancreatic β-cell differentiation from human embryonic stem cells," Cell Res. 24:1181-1200 (2014).
Maehr et al., "Generation of pluripotent stem cells from patients with type 1 diabetes," Proc. Natl. Acad. Sci. U.S.A. 106:15768-15773 (2009).
Mfopou et al., "Noggin, retinoids, and fibroblast growth factor regulate hepatic or pancreatic fate of human embryonic stem cells," Gastroenterology 138:2233-2245 (2010).
Micallef et al., "INSGFP/w human embryonic stem cells facilitate isolation of in vitro derived insulin-producing cells," Diabetologia 55:694-706 (2012).
Mootha et al., "PGC-1α-responsive genes involved in oxidative phosphorylation are coordinately downregulated in human diabetes," Nat. Genet. 34:267-273 (2003).
Murtaugh et al. "Genes, signals, and lineages in pancreas development," Annu. Rev. Cell Dev. Biol. 19:71-89 (2003).
Nair et al., "Islet formation in mice and men: lessons for the generation of functional insulin-producing β-cells from human pluripotent stem cells," Current Opinion in Genetics & Development 32:171-180 (2015).
Nostro et al., "Generation of beta cells from human pluripotent stem cells: Potential for regenerative medicine," Seminars in Cell and Developmental Biology 23:701-710 (2012).
Nostro et al., "Stage-specific signaling through TGFβ family members and WNT regulates patterning and pancreatic specification of human pluripotent stem cells," Development 138:861-871 (2011).
Pagliuca et al., "Generation of Functional Human Pancreatic β Cells In Vitro," Cell 159:428-439 (2014).
Pagliuca et al., "How to make a functional β-cell," Development 140:2472-2483 (2013).
Pan et al., "Pancreas organogenesis: from bud to plexus to gland," Dev. Dyn. 240:530-565 (2011).
Parnaud et al., "Cadherin Engagement Protects Human β-Cells from Apoptosis," Endocrinology 152(12):4601-4609 (2011).

(56) References Cited

OTHER PUBLICATIONS

Pisania et al, "Quantitative analysis of cell composition and purity of human pancreatic islet preparations," Lab Invest 90(11):1661-1675 (2010).
Posselt et al., "Islet Transplantation in Type 1 Diabetic Patients Using Calcineurin Inhibitor-Free Immunosuppressive Protocols Based on T-Cell Adhesion or Costimulation Blockade," Transplantation 90:1595-1601 (2010).
Rahier et al., "Cell populations in the endocrine pancreas of human neonates and infants," Diabetologia 20(5):540-546 (1981).
Rezania et al., "Maturation of Human Embryonic Stem Cell-Derived Pancreatic Progenitors Into Functional Islets Capable of Treating Pre-existing Diabetes in Mice," Diabetes 61:2016-2029 (2012).
Rezania et al., "Production of functional glucagon-secreting a-cells from human embryonic stem cells," Diabetes 60:239-247 (2011).
Rezania et al., "Reversal of diabetes with insulin-producing cells derived in vitro from human pluripotent stem cells," Nat Biotech 32(11):1121-1133 (2014).
Riedel et al., "Immunohistochemical characterisation of cells co-producing insulin and glucagon in the developing human pancreas," Diabetologia 55:372-381 (2011).
Roark et al., "Complex regulation controls Neurogenin3 proteolysis," Biol Open 1:1264-1272 (2012).
Russ et al., "Controlled induction of human pancreatic progenitors produces functional beta-like cells in vitro," EMBO J 34(13):1759-1772 (2015).
Russ et al., "In-Vivo Functional Assessment of Engineered Human Insulin-Producing Cells," In: Yarmush ML, Langer RS, editors; Soto-Gutierrez A, Navarro-Alvarez N, Fox IJ, editors. Cell Transplantation. Norwood, MA: Artech House, Methods in Bioengineering pp. 35-46 (2011).
Rutter et al., "Pancreatic ?-cell identity, glucose sensing and the control of insulin secretion," Biochemical Journal 466(2):203-218 (2015).
Schaffer et al., "Nkx6 Transcription Factors and Ptf1 a Function as Antagonistic Lineage Determinants in Multipotent Pancreatic Progenitors," Developmental Cell 18:1022-1029 (2010).
Schulz et al., "A scalable system for production of functional pancreatic progenitors from human embryonic stem cells," PLoS One 7: e37004, 17 pages (2012).
Scoville et al., "MLL3 and MLL4 Methyltransferases Bind to the MAFA and MAFB Transcription Factors to Regulate Islet ?-Cell Function," Diabetes 64(11):3772-3783 (2015).
Seymour et al., "Historical Perspective: Beginnings of the -Cell: Current Perspectives in -Cell Development," Diabetes 60:364-376 (2011).
Shaikh et al., "Microfluidic Device for Multimodal Characterization of Pancreatic Islets," Lab Chip. 9:97-106 (2009).
Shang et al., "β-cell dysfunction due to increased ER stress in a stem cell model of Wolfram syndrome," Diabetes 63:923-933 (2014).
Shapiro et al., "Islet transplantation in seven patients with type 1 diabetes mellitus using a glucocorticoid-free immunosuppressive regimen," N. Engl. J. Med. 343:230-238 (2000).
Shih et al., "A Notch-dependent molecular circuitry initiates pancreatic endocrine and ductal cell differentiation," Development 139: 2488-2499 (2012).
Shim et al., "Pancreatic islet-like three dimensional aggregates derived from human embryonic stem cells ameliorate hyperglycemia in streptozotocin induced diabetic mice," Cell Transplantation 24:2155-2168 (2015).
Stolovich-Rain et al., "Weaning Triggers a Maturation Step of Pancreatic β Cells," Developmental Cell. 32(5):535-545 (2015).
Subramanian et al., "Gene set enrichment analysis: A knowledge-based approach for interpreting genome-wide expression profiles," PNAS 102:15545-15550 (2005).
Szot et al., "Tolerance Induction and Reversal of Diabetes in Mice Transplanted with Human Embryonic-Stem-Cell-Derived Pancreatic Endoderm," Cell Stem Cell 16:148-157 (2015).
Szot et al., "Transplantation of Pancreatic Islets Into the Kidney Capsule of Diabetic Mice," J Vis Exp. (2007).
Taylor et al., "Nkx6.1 Is Essential for Maintaining the Functional State of Pancreatic Beta Cells," Cell Reports 4(6):1262-1275 (2013).
Trapnell et al., "TopHat: discovering splice junctions with RNA-Seq," Bioinformatics 25:1105-1111 (2009).
Tudurí et al., "Reprogramming gut and pancreas endocrine cells to treat diabetes," Diabetes, Obesity and Metabolism 13(Suppl 1):53-59 (2011).
Van Hoof et al., "Differentiation of human embryonic stem cells into pancreatic endoderm in patterned size-controlled clusters," Stem Cell Res 6:276-285 (2011).
Wijesekara et al., "Beta cell-specific Znt8 deletion in mice causes marked defects in insulin processing, crystallisation and secretion," Diabetologia 53(8):1656-1668 (2010).
Wojtusciszyn et al., "Insulin secretion from human beta cells is heterogeneous and dependent on cell-to-cell contacts," Diabetologia 51(10):1843-1852 (2008).
Xu et al., "Activin, BMP and FGF pathways cooperate to promote endoderm and pancreatic lineage cell differentiation from human embryonic stem cells," Mech. Dev 128:412-427 (2011).
Yoshihara et al., "ERR? Is Required for the Metabolic Maturation of Therapeutically Functional Glucose-Responsive β Cells," Cell Metabolism 23(4):622-634 (2016).
Zhou et al., "Extreme makeover: converting one cell into another," Cell Stem Cell 3:382-388 (2008).
Zhu et al., "Human pancreatic beta-like cells converted from fibroblasts," Nature Communications 7:10080, 13 pages (2016).

* cited by examiner

A

| Condition | Factors | |
|---|---|---|
| | d6-8 | d9-9.5 |
| 1 | Base | Base |
| 2 | C | C |
| 3 | N | N |
| 4 | R | R |
| 5 | RC | RC |
| 6 | RCN | RCN |
| 7 | Base | EK |
| 8 | C | EK |
| 9 | N | EK |
| 10 | R | EK |
| 11 | RC | EK |
| 12 | RCN | EK |
| 13 | Base | EKN |
| 14 | C | EKN |
| 15 | N | EKN |
| 16 | R | EKN |
| 17 | RC | EKN |
| 18 | RCN | EKN |
| BASE=B27 only control, R= Retinoic acid, C= Cyclopamine, N=Noggin, E=EGF, K= KGF. | | |

Conditions 1-6 are Group 1, 7-12 are Group 2, 13-18 are Group 3.

Figure 2

SEQUENCE LISTING

<160> NUMBER OF SEQ ID NOS: 4

<210> SEQ ID NO 1
<211> LENGTH: 20
<212> TYPE: DNA
<213> ORGANISM: Homo sapiens
<220> FEATURE:
<221> NAME/KEY: misc_feature
<223> OTHER INFORMATION: mtDNA 16S rRNA

<400> SEQUENCE: 1

```
gccttccccc gtaaatgata                                              20

<210> SEQ ID NO 2
<211> LENGTH: 20
<212> TYPE: DNA
<213> ORGANISM: Homo sapiens
<220> FEATURE:
<221> NAME/KEY: misc_feature
<223> OTHER INFORMATION: mtDNA 16S rRNA

<400> SEQUENCE: 2
ttatgcgatt accgggctct                                              20

<210> SEQ ID NO 3
<211> LENGTH: 25
<212> TYPE: DNA
<213> ORGANISM: Homo sapiens
<220> FEATURE:
<221> NAME/KEY: misc_feature
<223> OTHER INFORMATION: B2M

<400> SEQUENCE: 3
tgctgtctcc atgtttgatg tatct                                        25

<210> SEQ ID NO 4
<211> LENGTH: 22
<212> TYPE: DNA
<213> ORGANISM: Homo sapiens
<220> FEATURE:
<221> NAME/KEY: misc_feature
<223> OTHER INFORMATION: B2M

<400> SEQUENCE: 4
tctctgctcc ccacctctaa gt                                           22
```

PRODUCTION OF FULLY FUNCTIONAL MATURE BETA CELLS FROM HUMAN PANCREATIC PROGENITORS

CROSS REFERENCE TO RELATED APPLICATIONS

This application claims priority to U.S. Provisional Patent Application No. 62/320,185, filed Apr. 8, 2016 and U.S. Provisional Application No. 62/463,561, filed Feb. 24, 2017, which are hereby incorporated by reference in their entireties.

GOVERNMENT SUPPORT

This invention was made with government support under Grant No. R01 DK105831 awarded by the National Institutes of Health. The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 51589A_Seqlisting.txt; 1,141 bytes, created Apr. 7, 2017.

FIELD OF THE DISCLOSURE

The disclosure relates generally to the fields of stem cell biology and the treatment of diabetes mellitus.

BACKGROUND

Directed differentiation of human pluripotent stem cells into fully functional mature pancreatic beta cells holds great promise for cell replacement therapy for patients suffering from diabetes. This approach also offers the unique opportunity to study otherwise inaccessible aspects of human beta cell development and function in vitro.

Diabetes mellitus type 1 and 2 (T1D, T2D) are diseases characterized by autoimmune destruction or progressive dysfunction and subsequent loss of insulin-producing pancreatic beta cells, respectively. Current treatments for both types of patients with diabetes consist of regulating blood glucose levels through injections of exogenous insulin. While this approach provides reasonable management of the diseases, unwanted risks and long-term complications persist due to the inability of tightly maintaining glucose levels within a normal physiological range. Complications include life-threatening episodes of hypoglycemia, as well as long-term complications from hyperglycemia resulting in micro- and macro-angiopathy leading to cardiovascular pathologies and kidney failure, as well as neuropathy. Thus, there is a need for distinct treatments that provide superior control of glucose metabolism to minimize, or ideally eliminate long-term complications.

One existing approach to treating diabetes is transplantation of human cadaveric islet preparations into patients. This procedure typically results in better glycemic control, can render patients insulin independent for prolonged periods of time, and improves overall quality of life (Shapiro et al, 2000; Barton et al, 2012; Posselt et al, 2010). However, the severe shortage of cadaveric organ donors, requirement for lifelong immunosuppression, and variability between islet preparations hampers the use of islet transplantation as a readily available treatment for people with diabetes. Consequently, numerous research efforts have focused on identifying abundant alternative sources of surrogate glucose responsive insulin-producing cells (Hebrok, 2012; Efrat & Russ, 2012; Nostro & Keller, 2012; Tudurí & Kieffer, 2011; Bouwens et al, 2013; Zhou & Melton, 2008; Pagliuca & Melton, 2013). One of the most appealing approaches is the directed differentiation into insulin-producing cells from pluripotent human embryonic stem cells (hESC) (D'Amour et al, 2005; Nostro et al, 2011; Guo et al, 2013b; Van Hoof et al, 2011; Mfopou et al, 2010; Chen et al, 2009; Xu et al, 2011; Shim et al, 2014; Pagliuca et al 2014; Rezania et al 2014; Russ et al 2015) and more recently, induced pluripotent stem cells (Maehr et al, 2009; Shang et al, 2014; Hua et al, 2013).

Comprehensive knowledge of signaling events and temporal transcription factor (TF) expression patterns during rodent pancreas organogenesis (Pan & Wright, 2011; Seymour & Sander, 2011; Hebrok, 2003; Murtaugh & Melton, 2003) have accelerated the identification of culture conditions that allow the generation of pancreatic cell types from human pluripotent stem cells (hPSC). Early developmental stages, including definitive endoderm, gut tube-like cells and pancreatic progenitors can be efficiently induced in vitro. Subsequent transitions towards hormone-expressing cells in vitro are less efficient, however, and frequently lead to the formation of a mixed population of different pancreatic progenitors and polyhormonal endocrine cells (Guo et al, 2013a; Nostro et al, 2011; D'Amour et al, 2006). Such polyhormonal cells express insulin among other hormones, but lack expression of key beta cell transcription factors and do not secrete insulin in vitro in response to a glucose challenge—the hallmark function of bona fide beta cells (Guo et al, 2013a; Nostro et al, 2011; D'Amour et al, 2006). Nonetheless, transplantation of such heterogeneous cultures into surrogate mice results in the formation of glucose responsive beta-like cells after several months in vivo (Rezania et al, 2012; Kroon et al, 2008; Szot et al, 2014).

Sophisticated sorting experiments identified progenitor cells expressing Pancreatic and Duodenal Homeobox 1 TF (PDX1, also known as IPF1) and homeobox protein NKX6.1 as the source for these functional beta-like cells (Kelly et al, 2011). While polyhormonal cells have been identified in human fetal pancreas, suggesting that they may reflect aspects of the normal embryonic differentiation process (Riedel et al, 2011; De Krijger et al, 1992), increasing evidence indicates that hESC-derived polyhormonal cells preferentially give rise to single hormone positive alpha-like cells (Rezania et al, 2011). Thus, to fully replicate human beta cell development in vitro, it is imperative to better understand and accurately recapitulate the sequence of embryonic signals required for the proper specification of beta cell precursors, rather than alpha cell precursors.

During normal in vivo pancreatic organogenesis, functional beta cells are generated through a step-wise specification process starting with pancreatic progenitors, identified by the expression of PDX1 (Herrera et al, 2002). While PDX1+ cells can give rise to all pancreatic lineages (Herrera et al, 2002), the subsequent induction of NKX6.1 in these cells restricts their differentiation potential to only endocrine and ductal cells (Schaffer et al, 2010). Endocrine differentiation is then initiated in PDX1+/NKX6.1+ progenitors by short-lived expression of the basic helix loop helix TF Neurogenin 3 (NEUROG3, also known as NGN3) (Gu et al, 2002). Interestingly, the timing of NEUROG3 expression has been shown to be crucial in promoting the formation of diverse endocrine islet cell types (Johansson et al, 2007). For example, precocious induction of endocrine differentiation by forced expression of NEUROG3 in mice results predominantly in the generation of alpha cells (Johansson et al, 2007).

While several manuscripts published over the last few years (Pagliuca, Cell 159(2):428-439 (2014); Rezania, et al., Nat Biotech 32(11):1121-1133 (2014); Russ, et al., EMBO J 34:1759-1772 (2015); Zhu, et al., Nature Communications 7:10080 (2016)), described the formation of β-like-cells from hPSCs, these cells still possess limited functionality. For instance, β-like-cells fail to rapidly secrete insulin in dynamic perifusion assays indicating absent or delayed first phase insulin secretion. In addition, β-like-cells display suboptimal calcium responses to glucose that are slower and smaller in amplitude when compared with adult human islets (Pagliuca (2014) and Rezania et al. (2014)). Thus, despite the tremendous progress made in generating β-like-cells, the as of yet insurmountable challenge in the field has been to develop conditions conducive for full maturation of hPSC-derived-β-like-cells in vitro without genetic modifications.

Maturation of β-cells occurs gradually during postnatal development in both rodents (Blum, et al., Nat Biotech, 30:261-264 (2012); Aguayo-Mazzucato, et al., Diabetologia, 54:583-593 (2011); Jermendy, et al., Diabetologia, 54:594-604 (2011); Dhawan, et al., The Journal of Clinical Investigation 125:2851-2860 (2015)) and human (Arda, et al., Cell Metabolism, 23:909-920 (2016); Gregg et al., The Journal of Clinical Endocrinology & Metabolism, 97:3197-3206 (2012)). The process is characterized by acquisition of robust glucose stimulated insulin secretion (GSIS) at the correct physiological set point to prevent hypo- and hyperglycemia. Neonatal rodent β-cell function is profoundly different from adults as the threshold glucose concentration for secretion is lower and as a consequence, GSIS is blunted (Blum et al., (2012) and Dhawan et al. (2015)). Dramatic changes in the β-cell, both enhanced expression of transcription factors such as Neurod, Pdx1, Pax6, Mafb and Mafa (Gu, et al., Cell Metabolism 11:298-310 (2010), Gosmain, et al., Molecular Endocrinology 26:696-709 (2012), Dai, et al., Diabetologia 55:707-718 (2012), Scoville, et al., Diabetes 64:3772-3783 (2015)), and repression of disallowed genes including Hk1, Ldha and Mct1 (Dhawan et al., (2015) and Lemaire, et al., Annual Review of Nutrition 36:45-71 (2016)) have been attributed to maturation. Furthermore, a switch in glucose metabolism in maturing cells, from anaerobic glycolysis to mitochondrial oxidative phosphorylation is emerging as key mechanism enabling and enhancing β-cell function. For example, ectopic expression of a mitochondrial regulator, ERRγ, led to enhanced function of hPSC-derived-β-like-cells (Yoshihara, et al., Cell Metabolism 23:622-634 (2016)). Although recent evidence indicates marked changes in gene expression between young and adult human β-cells (Arda et al., (2016)), temporal dynamics of human β-cell maturation remain unclear. Neonates possess immature β-cells because they display larger spikes in plasma insulin on infusion of amino acids than glucose, and show higher plasma insulin/glucose ratios compared to infants and adults (Hawdon, et al., Archives of Disease in Childhood, 68:274-279 (1993), Kaye, et al., The Journal of Pediatrics, 59:836-847 (1961)). Importantly, infant islets (1-3 years old) secrete insulin in an identical manner to adult islets on stimulation with various secretagogues (Henquin, et al., PLoS ONE 11:e0165961 (2016)), indicating that they are functionally mature by one-year of age. Thus, human β-cells appear to mature after birth to assume a juvenile mature state and then age over time to become adult mature β-cells. The secretory capacity of juvenile mature human β-cells continues to increase until puberty with enrichment of factors such as MAFA, SIX2 and SIX3 (Arda et al., 2016 and Scoville et al., 2015)), suggesting that likely MAFB and other factors may play an indispensable role in attaining early function.

In addition to the intracellular processes, endocrine cell clustering, compaction and formation of definitive islets are morphological processes that proceed well into postnatal development and coincide with maturation. Studies of pancreas organogenesis in vivo have shown that cells expressing endocrine hormone first appear scattered in the pancreatic epithelium; subsequently, these cells migrate and aggregate into islet-like clusters where they acquire functional maturity (Gregg et al. (2012), Nair, et al., Current Opinion in Genetics & Development 32:171-180 (2015), Jeon, et al., J Histochem Cytochem 57:811-824 (2009); Rahier, et al., Diabetologia 20:540-546 (1981)). In contrast, current in vitro hPSC differentiation protocols produce a mixed population of PDX1+NKX6.1+ pancreatic progenitors intermingled with differentiated endocrine cells, possibly because the delamination and clustering events present during endogenous islet formation and maturation are not incorporated.

For all of the foregoing reasons, a need continues to exist in the art for materials and methods that provide for the directed differentiation of pluripotent stem cells (e.g., human pluripotent stem cells) into functional insulin-producing mature beta cells for treatment of diabetes.

SUMMARY

Cell therapies utilizing functional insulin-producing beta cells produced from human stem cells hold great promise for the treatment of diabetes. The disclosure provides a simplified suspension-culture-based differentiation protocol that allows for the correct temporal specification of pancreatic and endocrine progenitors into immature beta-like cells, and subsequent maturation of these cells into fully functional beta cells, in vitro. This approach provides a fast and reproducible supply of functional human beta cells and enables detailed investigations into human pancreas development and beta cell biology. Salient features of the technology disclosed herein includes the exclusion of commonly used BMP inhibitors during human embryonic stem cell-to-pancreatic progenitor cell differentiation prevents precocious endocrine induction. Sequential exposure of foregut cells to retinoic acid followed by combined EGF/KGF treatment establishes highly pure PDX1$^+$ and PDX1$^+$/NKX6.1$^+$ progenitor populations, respectively. Precise temporal induction of endocrine differentiation in PDX1$^+$/NKX6.1$^+$ progenitors, but not in PDX1$^+$/NKX6.1$^-$ progenitors, results in the generation of monohormonal beta-like cells in vitro.

Elaborating on the preceding observations, current pancreatic progenitor differentiation protocols promote precocious endocrine commitment, ultimately resulting in the generation of non-functional polyhormonal cells. Omission of commonly used BMP inhibitors during pancreatic specification prevents precocious endocrine formation while treatment with retinoic acid followed by combined EGF/KGF efficiently generates both PDX1$^+$ and subsequent PDX1$^+$/NKX6.1$^+$ pancreatic progenitor populations, respectively. Precise temporal activation of endocrine differentiation in PDX1$^+$/NKX6.1$^+$ progenitors produces glucose-responsive beta-like cells in vitro. Thus, the simplified and scalable system disclosed herein accurately recapitulates key early steps of human pancreas development, and provides a fast and reproducible supply of pancreatic insulin-producing cells.

In one aspect, the disclosure provides a method of producing endocrine progenitor cells from pluripotent stem cells comprising: (a) incubating pluripotent stem cells (PSCs) in culture medium comprising Wnt3a, Activin A, TGβi, and keratinocyte growth factor (KGF) for 3-7 days; (b) exposing the cells resulting from step (a) to medium comprising retinoic acid (RA) for 2-3 days; and (c) culturing the cells resulting from step (b) in medium comprising RA, epidermal growth factor (EGF), and KGF, thereby producing a culture comprising greater than 70% PDX1$^+$ NKX6.1$^+$ endocrine progenitor cells. In some embodiments, the pluripotent stem cells are human. In some embodiments, the incubating step (a) is five days, and/or the exposing step (b) is two days, and/or the culturing step (c) is 3-5 days.

A related aspect of the disclosure provides a method as described above that further comprises incubating the culture comprising PDX1$^+$ NKX6.1$^+$ endocrine progenitor cells in medium comprising Alki, T3, XXi, LDN, NEAA, N-acetyl Cysteine, zinc sulfate, heparin, glutamax, and vitamin C for at least 8 days, thereby producing INS$^+$ NKX6.1$^+$ GCG$^-$ immature β-like cells. In some embodiments, the culture is incubated for 8-10 days. In some embodiments, the method further comprises sorting the cells in the culture to enrich for INS$^+$ NKX6.1$^+$ GCG$^-$ immature β-like cells, such as by subjecting the cells to flow cytometry. In some embodiments, the methods described herein further comprise re-aggregating the immature beta-like cells into clusters of about 100-150 μm. In some embodiments, the re-aggregating is accomplished using Aggrewells, the GravityPLUS Hanging Drop System or Perfecta3D Hanging Drop Plates. In some embodiments, the method further comprises sorting and re-aggregating and maintaining the cells in CMRL (5.5 mM glucose) containing B27 (or FBS), Glutamax, NEAA, Rock inhibitor, ALKi II, vitamin C, T3, N-acetyl cysteine, zinc sulfate and heparin for at least 6 days, such as for 6-14 days, thereby producing mature beta cells in islet-sized clusters, called enhanced beta-clusters (eBCs). In some embodiments, the eBCs respond to in vivo glucose challenges within about three days of transplantation of the cells into a subject. It is expected that this response will occur upon transplantation of eBCs into a human. In some embodiments, culturing of the re-aggregated clusters produces no detectable cell types of exocrine pancreatic lineages. In some embodiments, culturing produces no duct cell or acinar cell. In some embodiments, culturing of the re-aggregated clusters produces less than 4% NKX6.1$^+$ PDX1$^+$ C-peptide$^-$ pancreatic epithelial progenitor cells in eBCs. In some embodiments, at least 95% of the cells in eBCs express chromogranin A. In some embodiments, at least 95% or all of the cells of the eBCs stain positive for synaptophysin, such as embodiments in which all of the cells of eBCs stain positive for synaptophysin. In some embodiments, up to 80% of the eBC-cells are monohormonal C-peptide$^+$ cells, or up to 90% of the eBC-cells are monohormonal C-peptide$^+$ cells. In some embodiments, 80% of the eBC-cells are double positive for C-peptide and NKX6.1, including embodiments wherein 87% of the eBC-cells are double positive for C-peptide and NKX6.1.

In some embodiments, the basal oxygen consumption rate of eBCs is more than about 10.799 (i.e., 7.285+3.514) picomoles of oxygen consumed per minute per nanogram of C-peptide. In some embodiments, the basal oxygen consumption rate of eBCs is more than about 3.771 (i.e., 7.285−3.514) picomoles of oxygen consumed per minute per nanogram of C-peptide. In some embodiments, the extracellular acidification rate of eBCs is at most 0.6922 (1.365−0.6728) milli pH units per minute per nanogram of C-peptide. In some embodiments, the extracellular acidification rate of eBCs is at most 2.0378 (1.365+0.6728) milli pH units per minute per nanogram of C-peptide.

Another aspect of the disclosure is a method for producing beta cells, e.g., fully functional mature beta cells, from INS$^+$ NKX6.1$^+$ GCG$^-$ immature β-like cells comprising sorting the INS$^+$ NKX6.1$^+$ GCG$^-$ immature β-like cells in a culture to enrich for INS$^+$ NKX6.1$^+$ GCG$^-$ immature β-like cells and re-aggregating the cells into islet-sized clusters, for example into 100-150 μm diameter islet-sized clusters with about 500-2,000 cells/cluster in micro-patterned wells, such as Aggrewell™ microwells, the Gravity PLUS Hanging Drop System, or Perfecta 3D Hanging Drop Plates, and maintaining the clusters in CMRL (5.5 mM glucose) containing B27 (or FBS), Glutamax, NEAA, Rock inhibitor, ALKi II, vitamin C, T3, N-acetyl cysteine, zinc sulfate and heparin for at least 6 days, thereby producing mature beta cells. In some embodiments, the sorting comprises subjecting the cells to flow cytometry. In some embodiments, maturation of beta cells is achieved through activation of mitochondrial oxidative respiration.

In another aspect, the disclosure provides a method of producing mature beta cells from sorted INS$^+$ NKX6.1$^+$ GCG$^-$ immature β-like cells comprising re-aggregating the cells, for example into 100-150 μm islet-sized clusters with about 500-2000 cells/cluster in Aggrewell™ microwells, Gravity PLUS Hanging Drop System or Perfecta 3D Hanging Drop Plates, and maintaining the clusters in CMRL (5.5 mM glucose) containing B27 (or FBS), Glutamax, NEAA, Rock inhibitor, ALKi II, vitamin C, T3, N-acetyl cysteine, zinc sulfate and heparin for at least 6 days, thereby producing mature beta cells. In some embodiments, the cells are maintained for 6-14 days.

Yet another aspect of the disclosure is the beta cell produced according to any of the above-described methods.

Still another aspect of the disclosure is drawn to a method of treating diabetes mellitus comprising administering an effective amount of the beta cell disclosed above. In some embodiments, the subject is immune-modulated or immuno-compromised. In some embodiments, the beta cells described herein are administered in an encapsulated form. In some embodiments, the diabetes mellitus is type I or type II diabetes mellitus.

In another aspect, the disclosure provides a method of generating a PDX1$^+$ progenitor cell comprising contacting an embryonic stem cell with an effective amount of a retinoic acid compound, thereby inducing formation of a PDX1$^+$ progenitor cell. In some embodiments, the embryonic stem cell is a human embryonic stem cell. In some embodiments, the embryonic stem cell is contacted with a retinoic acid compound in vitro. Embodiments are also contemplated that further comprise not contacting the embryonic stem cell with a bone morphogenic protein (BMP) inhibitor prior to expression of NKX6.1 by the cell.

In some embodiments of this aspect of the disclosure, the method further comprises contacting the cell with effective amounts of epidermal growth factor and keratinocyte growth factor, thereby inducing formation of a PDX1$^+$/NKX6.1$^+$ progenitor cell. In some of these embodiments, the cell expresses NKX6.1 prior to the cell contacting at least one of epidermal growth factor and keratinocyte growth factor (K). In some of these embodiments, the cell expresses NKX6.1 prior to contacting epidermal growth factor and keratinocyte growth factor.

In yet other embodiments, the method further comprises inducing the PDX1$^+$/NKX6.1$^+$ progenitor cell to express NEUROG3, resulting in production of an INS$^+$/NKX6.1$^+$ beta-like cell. In some embodiment, the NEUROG3 expression is induced by contacting the PDX1$^+$/NKX6.1$^+$ progenitor cell with an effective amount of an inhibitor of bone morphogenetic protein, an inhibitor of TGFβ/ALK, or an inhibitor of sonic hedgehog. Embodiments are contemplated wherein the PDX1$^+$/NKX6.1$^+$ progenitor cell is contacted by an effective amount of bone morphogenetic protein and an effective amount of an inhibitor of TGFβ/ALK. In some embodiments, the PDX1$^+$/NKX6.1$^+$ progenitor cell is contacted by an effective amount of bone morphogenetic protein and an effective amount of an inhibitor of sonic hedgehog. In some embodiments, the inhibitor of bone morphogenetic protein is Noggin or the inhibitor of sonic hedgehog is Cyclopamine.

This aspect of the disclosure further comprehends methods wherein the NEUROG3 expression is induced by exposure of the PDX1$^+$/NKX6.1$^+$ progenitor cell to effective amounts of a TATA-Binding Protein, an Activin receptor-Like Kinase inhibitor, Noggin and Keratinocyte Growth Factor, or K. In some embodiments, the NEUROG3 expression begins before expression of NKX2.2 is detected. In some embodiments, no more than 5% of the generated cells are polyhormonal cells. In some embodiments, the INS$^+$/NKX6.1$^+$ beta-like cell is responsive to glucose levels. In some of these embodiments, the INS$^+$/NKX6.1$^+$ beta-like cell secretes an increased level of insulin in response to an increased glucose level. In some embodiments, the INS$^+$/NKX6.1$^+$ beta-like cell does not express a detectable level of the Ki67 marker. In some embodiments, the INS$^+$/NKX6.1$^+$ beta-like cell is an insulin$^+$ beta cell, a glucagon– beta cell, or an insulin$^+$/glucagon– beta cell. In a related aspect, the method further comprises transplanting the INS$^+$/NKX6.1$^+$ beta-like cell into a human, such as a human who is diabetic.

A related aspect of the disclosure provides the method described above, further comprising (a) sorting the INS-expressing cells to obtain immature beta-like cells; and (b) re-aggregating the immature beta cells into islet-sized clusters (e.g., about 100-150 µm; typically 500-2,000 cells) by culturing the cells in micro-patterned wells comprising CMRL (5.5 mM glucose) containing B27 (or FBS), Glutamax, NEAA, Rock inhibitor, ALKi II, vitamin C, T3, N-acetyl cysteine, zinc sulfate and heparin to produce beta cell-enriched islet-like clusters. In some embodiments, greater than 95% of the resulting re-aggregated clusters are beta cells.

Some embodiments of the methods according to the disclosure are provided wherein the INS$^+$/NKX6.1$^+$ beta-like cell does not express a detectable level of the Ki67 marker.

Another aspect of the disclosure is a method for generating an INS$^+$/NKX6.1$^+$ beta-like cell further compromising transplanting the INS$^+$/NKX6.1$^+$ beta-like cell into a human. In some embodiments, the human is diabetic.

Still another aspect of the disclosure is a method of treating diabetes comprising transplanting an effective amount of eBCs to a diabetic subject. Also disclosed is a method of screening for candidate modulators of insulin response to glucose comprising: administering a candidate modulator to an eBC; exposing the eBC to glucose; and measuring the insulin production in response to glucose exposure, wherein a candidate modulator is identified as a modulator of insulin response to glucose if the insulin production of the eBC in the presence of the candidate modulator differs from the insulin production of the eBC in the absence of the candidate modulator. The disclosure further provides a method of increasing pancreatic beta cell function in a diabetic subject comprising transplanting an effective amount of eBCs into the subject, thereby increasing the level of beta cell function in the subject. In some embodiments, the beta cell function is production of insulin in response to glucose challenge. In some embodiments, the diabetes is type I or type II diabetes.

Another aspect of the disclosure is a method of screening compound toxicity comprising administering a compound to an eBC and measuring the function of the eBC, wherein a compound exhibits a toxic effect if the eBC function differs in the presence compared to the absence of the compound. In some embodiments, toxicity is measured by determining cell viability. Yet another aspect provides a method of screening for a candidate therapeutic comprising identifying a single nucleotide polymorphism linked to diabetes, producing an eBC comprising beta cells bearing the single nucleotide polymorphism, exposing the eBC to a candidate therapeutic, and measuring eBC function in the presence compared to the absence of the candidate therapeutic, wherein the candidate therapeutic is identified as a therapeutic if the eBC function differs in the presence of the candidate therapeutic compared to the eBC function in the absence of the candidate therapeutic.

A further aspect of the disclosure is a method of screening for a candidate therapeutic comprising identifying a single nucleotide polymorphism linked to diabetes, producing an eBC comprising beta cells bearing the single nucleotide polymorphism, generating an eBC comprising beta cells that do not bear the single nucleotide polymorphism, exposing each eBC to a candidate therapeutic, and measuring the function of each eBC in the presence of the candidate therapeutic, wherein the candidate therapeutic is identified as a therapeutic if the function in the two eBCs differ. In some embodiments, the function is insulin production in response to glucose.

Another aspect is drawn to a method of generating a bio-artificial pancreas or pancreatic tissue comprising administering a therapeutically effective amount of an eBC to a pancreatic organ or tissue.

In yet another aspect, the disclosure provides a method of screening for a cell-encapsulation technology for transplantation and development of a bio-artificial pancreas or pancreatic tissue comprising contacting the cell-encapsulation technology with an eBC, encapsulating the eBC, and measuring the secretion of insulin from the cell-encapsulation technology in response to exposure to glucose. Another aspect of the disclosure is a method of measuring the effect of a stressor on a beta cell comprising contacting an eBC comprising a beta cell with a stressor and measuring the effect of the stressor on the eBC. In some embodiments, the stressor is hypoxia, an ER stressor, or an oxidative stressor. In some embodiments, the effect being measured is viability or glucose-responsive insulin production.

The disclosure also provides a method of measuring the effect of a β-cell on the immune system comprising contacting an immune cell or an immune system with an eBC comprising a beta cell and measuring the immune function of the immune cell or the immune system. In some embodiments, the eBC contacts the immune system or the immune cell in vivo. In some embodiments, the eBC contact the immune cell in vitro. Further provided is a method of developing a tissue or an organ comprising culturing an eBC with at least one of an alpha cell, a delta cell, an endothelial cell, a neural cell, a mesenchymal cell, or a pericyte. In some embodiments, the tissue or organ is developed on a chip. In some embodiments, the tissue is an islet of Langerhans. The method can further comprise a cell from an organ or tissue other than pancreas or pancreatic tissue, e.g., a liver, a heart, fat, muscle, bone, spleen, stomach, intestine, kidney, adrenal gland, thyroid gland, thymus, brain, skin, or blood.

Other features and advantages of the disclosure will be better understood by reference to the following detailed description, including the drawing and the examples.

DETAILED DESCRIPTION

Figure 1:
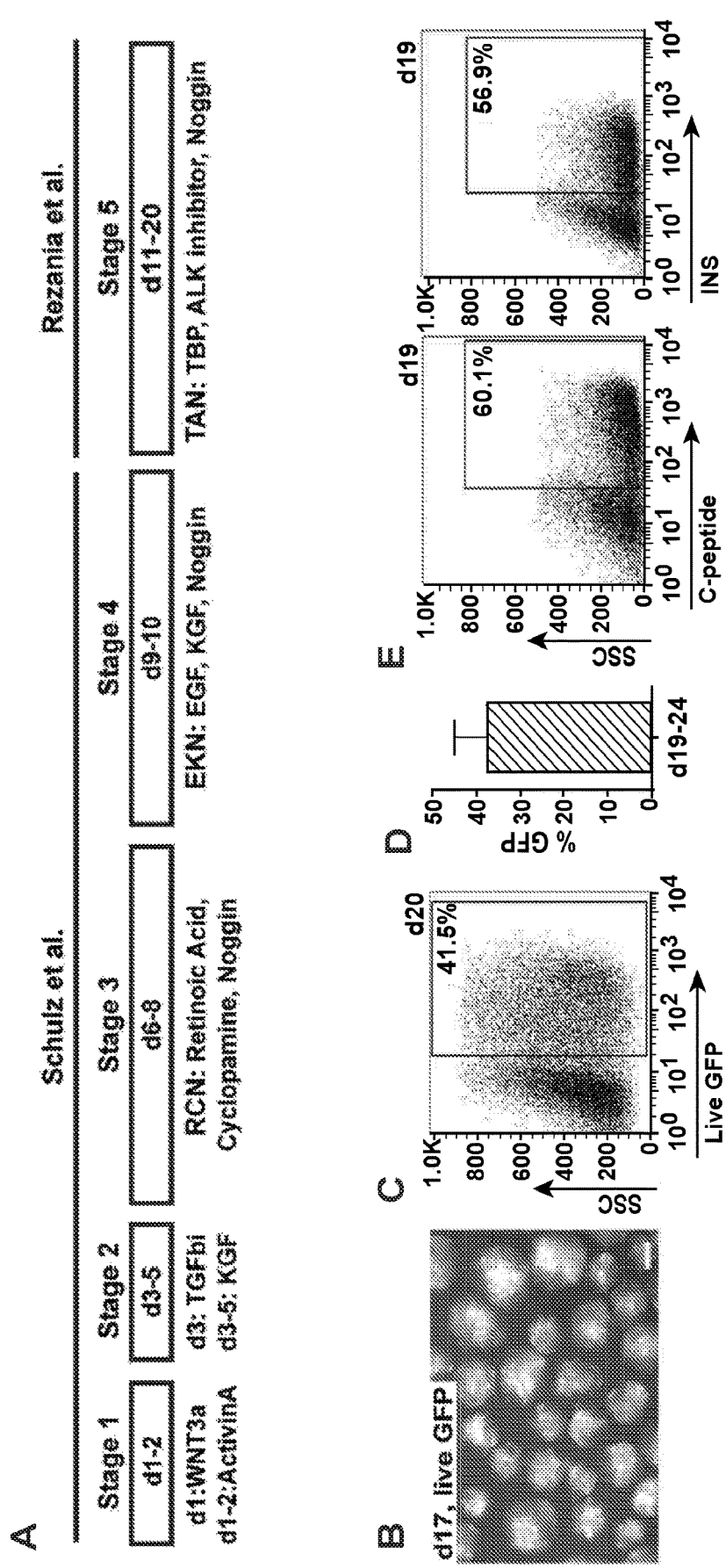
FIG. 1. Pancreatic differentiation of hESCs using a large-scale culture system results in two distinct subsets of insulin-producing cells. A: Schematic outlining the differentiation method employed. R=Retinoic acid, C=Cyclopamine, N=Noggin, E=Epidermal growth factor, K=Keratinocyte growth factor, T=TBP, and A=ALK inhibitor. B: Micrograph of MEL1INS-GFP cell clusters after 17 days of differentiation demonstrating strong GFP expression (GFP expression in white). Scale bar=200 µm. C: Flow cytometric analysis at day 20 of differentiation showing 41.5% of all cells expressing GFP under the control of the endogenous insulin promoter. D: Quantification by flow cytometry of the average percentage of GFP$^+$ cells within differentiated cultures after 19-24 days. n=7. Values are average±standard deviation (SD). E: Flow cytometric analysis of intracellular human-specific C-peptide (C-PEP) and insulin (INS) shows comparable percentages of C-PEP and INS positive cells. F: Immunofluorescence staining for C-PEP and glucagon (GCG), and flow cytometric quantification of GCG$^+$/C-PEP$^+$ (red gate), GCG$^-$/C-PEP$^+$ (black gate) populations at days 13 and 19 of differentiation. G: Immunofluorescence staining for C-PEP and NKX6.1, and flow cytometric quantification of NKX6.1$^+$/INS$^+$ (green gate) and NKX6.1$^-$/INS$^+$ (red gate) populations at days 13 and 19. Immunofluorescence insets show two distinct phenotypes for C-PEP$^+$ cells (NKX6.1$^+$ and NKX6.1$^-$). A robust INS/NKX6.1 double positive population is only detected at day 19. H: Transmission electron microscopy of day 20 clusters. Cells contain both secretory vesicles with electron dense cores surrounded by electron light halos (green box), akin to bona fide beta cell vesicles, as well as other granules similar to those found in non-beta pancreatic cells (red boxes).
Figure 1:
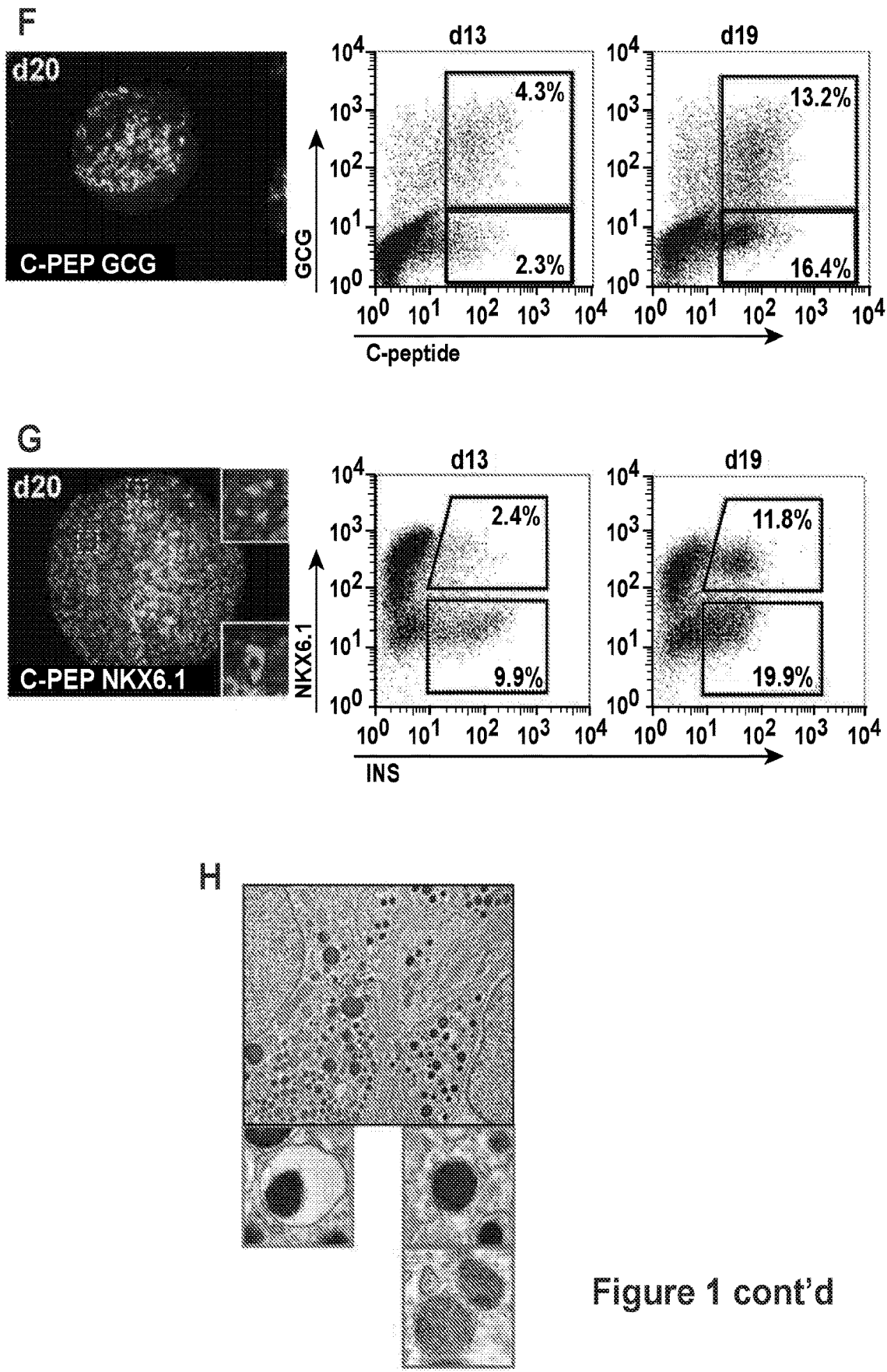

The disclosure provides methods of generating fully functional mature β-cells in enriched 3 clusters from human pluripotent stem cells comprising the steps of exposing progenitor cells to temporally ordered inducing agents, cell sorting and re-aggregation of immature β-like cells generated from hPSCs to form enriched Beta-clusters (eBCs). In general terms, the methods disclosed herein provide for isolating hPSC-derived β-like cells using any technique known in the art, such as fluorescence-activated cell sorting (FACS) cytometry with the coding region for Green Fluorescence Protein (GFP) operably linked to the insulin promoter. In principle, other techniques are available, including Magnetic-activated cell sorting (MACS) with antibodies that specifically enrich for endocrine cells and/or deplete progenitor cells, antibodies raised against synthetic epitopes ectopically driven by the insulin promoter or selective destruction of progenitor cells using antibody-drug conjugates. In addition, mechanical isolation, taking advantage of specific properties of immature β-cells and pancreatic progenitors, is also contemplated. The isolated, or sorted, hPSC-derived β-like cells are re-aggregated into about 100-150 μm-sized clusters with about 500-2,000 cells/cluster in Aggrewell™ micro-wells, the GravityPLUS Hanging Drop System, or Perfecta3D Hanging Drop Plates. The clusters generated by this technique are called 'enhanced β-clusters' (eBCs). The eBCs are further cultured in optimized media conditions constituting 'maturation media' for 6-14 days. Medium ingredients for this culturing step include reduced glucose concentration (about 5.5 mM) as well as high concentrations of Alk5 inhibitor II and T3. An exemplary medium is CMRL (5.5 mM glucose) containing B27 (or FBS), Glutamax, NEAA, Rock inhibitor, ALKi II, vitamin C, T3, N-acetyl cysteine, zinc sulfate and heparin. These clusters exclusively constitute cells committed to the endocrine lineage, particularly enriched in the β-cell lineage.

The disclosure provides eBCs, and methods of producing and using eBCs, that display superior functional properties in vitro and in vivo, analogous to human islets. Without wishing to be bound by theory, it is believed that, mechanistically, coalescence of immature β-like cells induces metabolic maturation and drives mitochondrial oxidative respiration, central elements of stimulus-secretion coupling in β-cells. The resulting mature β-cells are highly similar to primary adult β-cells by transcriptome, immunohistochemical, and functional analyses. The findings disclosed herein point to endocrine cell clustering as a significant step in the maturation of hPSC-derived-β-like-cells under cell culture conditions.

Given that hESC-derived polyhormonal cells have been shown to give rise to alpha cells (Rezania et al, 2011), we expected the in vitro generation of polyhormonal endocrine cells to result from premature assignment to the endocrine fate. To address this issue, a detailed step-wise analysis of pancreatic progenitor generation and endocrine induction was performed. Most current protocols efficiently establish PDX1$^+$ progenitors by using Retinoic Acid in combination with molecules to inhibit bone morphogenic protein (BMP) and sonic hedgehog (SHH) signaling pathways, while simultaneously adding either fibroblast growth factor 10 or keratinocyte growth factor (KGF, also known as FGF7) (Rezania et al, 2012; Hua et al, 2013; Guo et al, 2013b; Nostro & Keller, 2012; Mfopou et al, 2010). Disclosed herein is the need to temporally control the introduction of inducing agents in the pathway of directed differentiation of embryonic stem cells to functional beta-like pancreatic cells. For example, the early or indiscriminate use of BMP inhibitors to specify pancreatic cells promotes the precocious induction of endocrine differentiation in PDX1$^+$ pancreatic progenitors, which results in the formation of polyhormonal cells. BMP inhibitors do have a role in directed differentiation of ES cells to beta-like cells, but only if the inhibitors are introduced later in the process, i.e., after the cells have begun to express NKX6.1. Simplified culture conditions have been identified that replicate fetal endocrine development and allow for the precise and efficient generation of PDX1$^+$ and PDX1$^+$/NKX6.1$^+$ progenitor populations without precocious activation of the endocrine marker NEUROG3. Subsequent induction of endocrine differentiation in correctly specified PDX1$^+$/NKX6.1$^+$ progenitor cells results in the formation of glucose-responsive insulin-expressing beta-like cells in vitro within, or less than, three weeks. Our study, therefore, details a simplified directed differentiation protocol that closely recapitulates key aspects of human endocrine development and results in the formation of large numbers of glucose-responsive beta-like cells under cell culture conditions.

Figure 5:
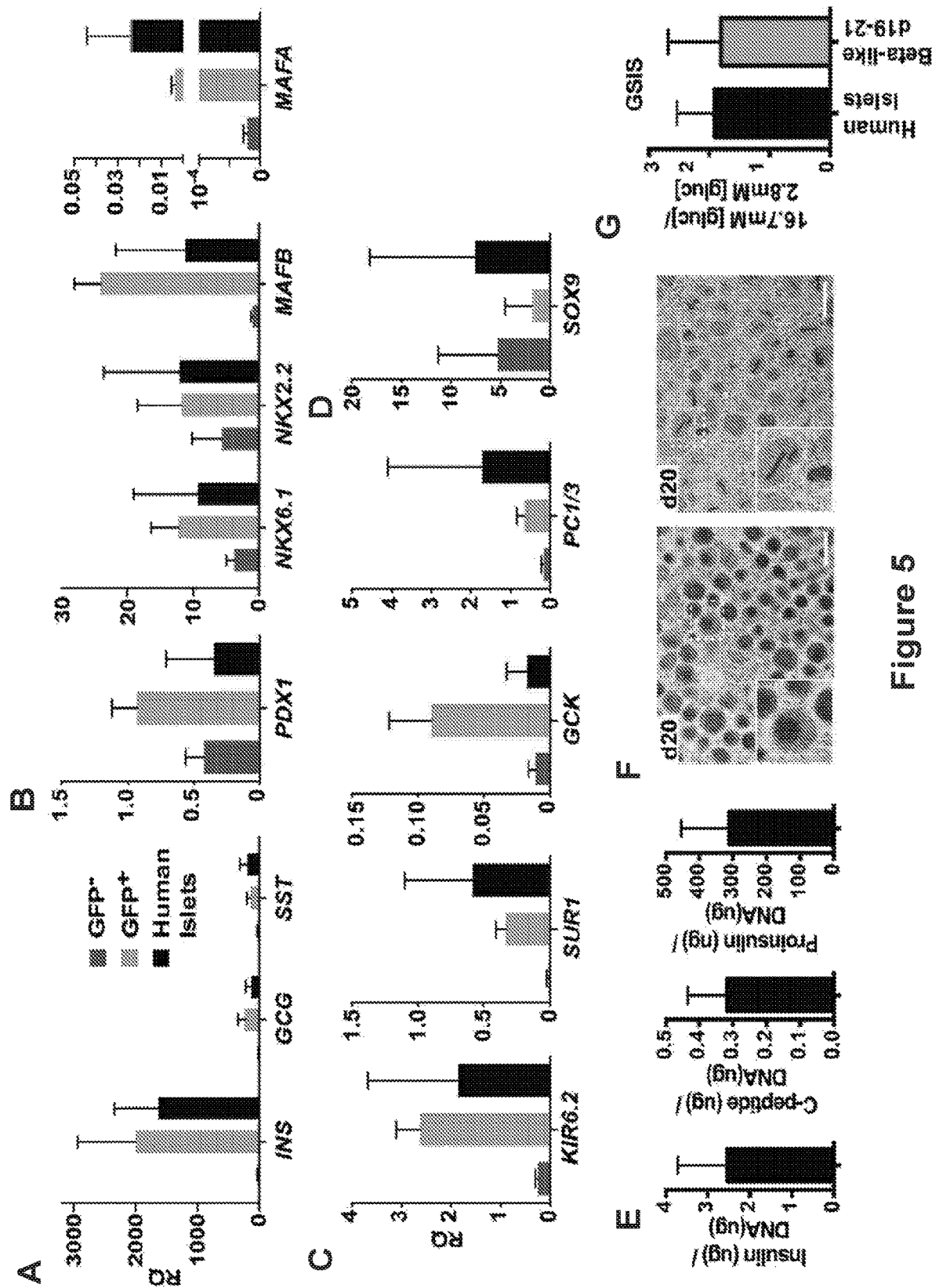
FIG. 5. Beta-like cells exhibit key features of bona fide human beta cells and are glucose responsive. A-D: Quantitative PCR analysis of selected gene transcripts in sorted GFP$^+$ beta-like cells (green bars), GFP– populations (blue bars) and human islet preparations (black bars). Results shown relative to the endogenous control GAPDH. RQ=relative quantification. Values are average±SD. n=4 independent experiments for hESC-derived cell populations at days 19-20 and n=3 for human islets. E: Insulin, human C-peptide, and proinsulin content relative to DNA in beta-like cells at day 19. Data presented is average±standard error (n=3 independent experiments, technical duplicates). F: Transmission electron microscopy images of beta-like cells at day 20. One of three experiments with similar results is shown. Scale bar=500 nm. Insets represent secretory vesicles akin to granules present in bona fide human beta cells. G: Glucose-stimulated insulin secretion (GSIS) of human islets and beta-like cells at days 19-20. "Y' axis indicates ratio of insulin secreted in low glucose conditions to that secreted in high glucose conditions. Values are average±standard deviation (SD) (n=3 for human islets and n=10 for beta-like cells).
Figure 6:
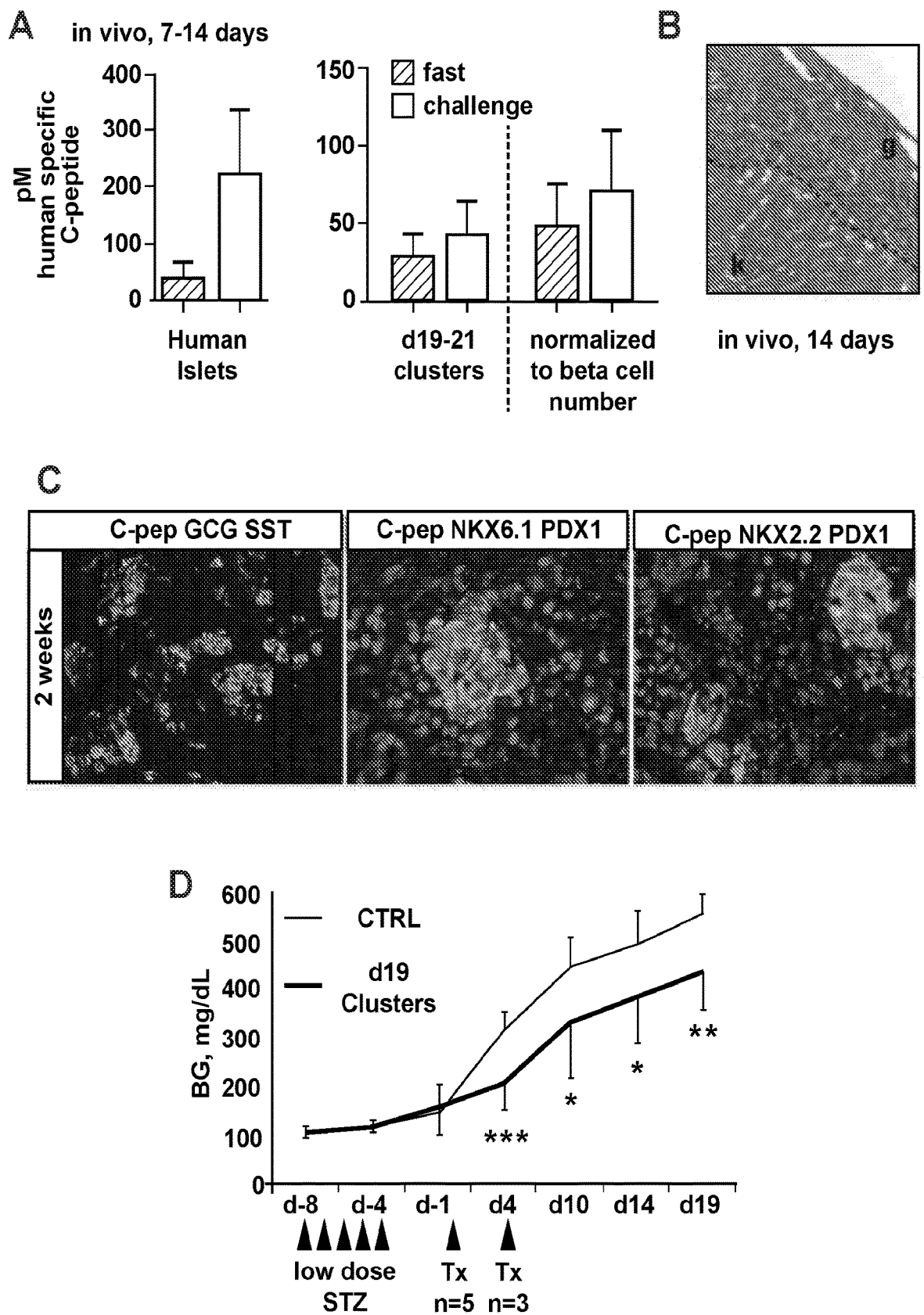
FIG. 6. Beta-like cells remain glucose responsive after short-term transplantation. A: Levels of circulating human c-peptide measured in sera of mice 7-10 days after transplantation with either 4000 human islets or $5.0 \times 10^6$ direct-differentiated cells (containing approximately $1.15 \times 10^6$ beta-like cells). Fasting and challenge sera were collected following an overnight fast and 1 hour after intraperitoneal glucose challenge, respectively. Dashed line separates raw data from serum c-peptide measurements normalized to the number of beta cells present in each human islet graft (4000 human islets transplanted each containing about 1000 cells, approximately 50% of which are beta cells, hence $2.0 \times 10^6$ beta cells present in grafts total). n=5 for human islets and n=12 for hES-derived grafts. B: Hematoxylin and Eosin staining of day 14 graft. k=kidney, g=graft. Representative data from one of three mice are shown. C: Immunofluorescence staining of differentiated hES grafts 2 weeks post-transplantation for human C-peptide, Glucagon (GCG), Somatostatin (SST), PDX1, NKX6.1, and NKX2.2. Representative data from one of three mice are shown. D: Blood glucose (BG) levels of mice treated with streptozotocin to ablate endogenous beta cells (STZ) followed by transplantation (Tx) of beta-like cell containing clusters either at day 0 or day 4, as indicated (n=8, two independent differentiation experiments). Values are average±standard deviation. Statistical significance was calculated using two-tailed t-test. p=*<0.05, <0.01, and *<0.001. Control (CTRL)=6-9 animals.
Figure 11:
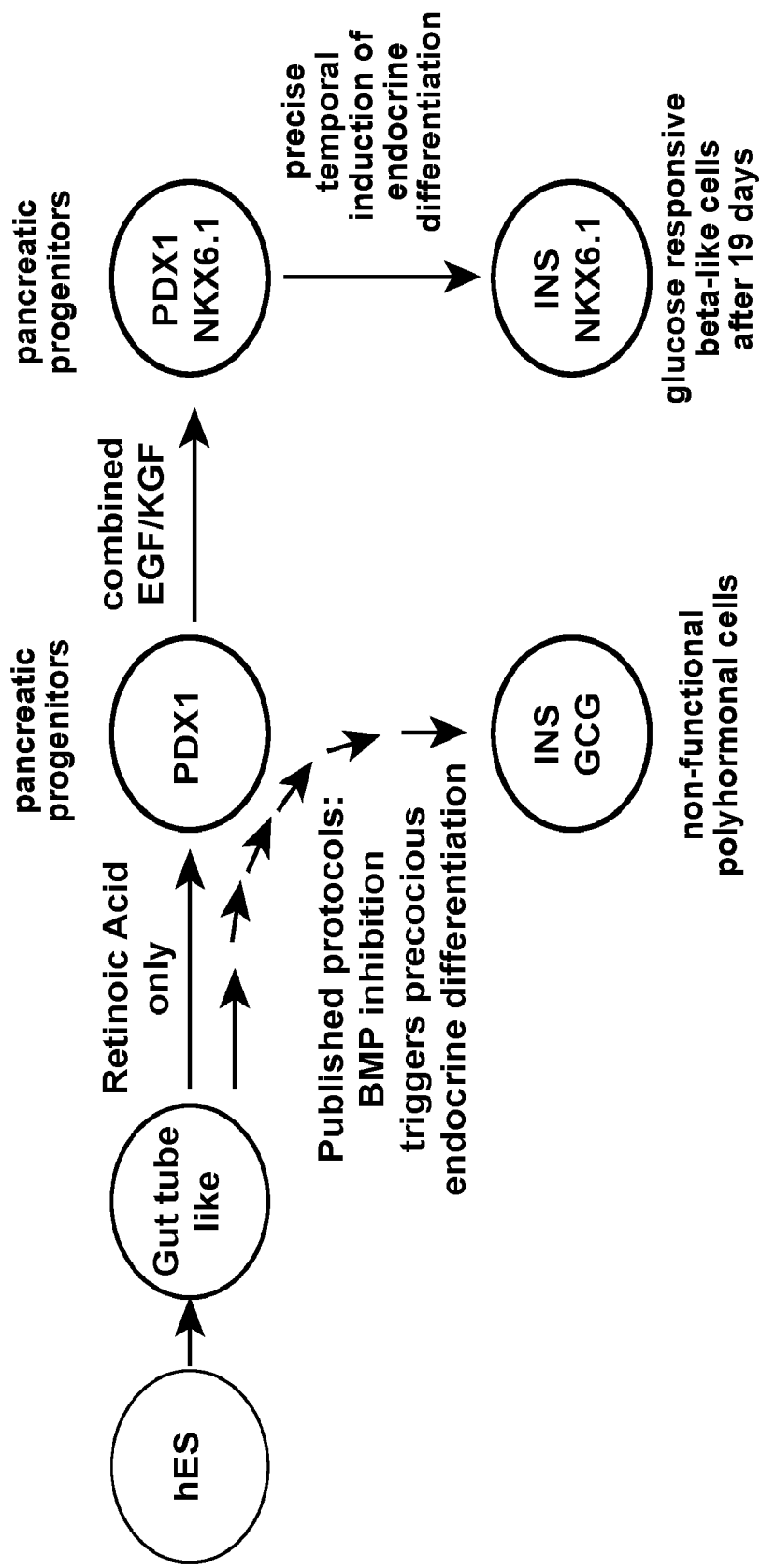
FIG. 11. Schematic comparative illustration of pancreatic cell (e.g., beta islet cell) directed differentiation protocols known in the art and disclosed herein. Provided is an illustration comparing directed differentiation protocols for eliciting differentiation of human embryonic stem cells (hES) to pancreatic cells such as beta islet cells. Conventional protocols proceed from hES through foregut to the column in the center of the Figure proceeding through PDX1 to NGN3 and then to INSGCG. The methodology disclosed herein proceeds from hES through foregut, PDX1, PDX1/NKX6.1, NGN3, and then to INS NKX6.1.

A simplified differentiation protocol is disclosed herein that replicates key steps of embryonic pancreas organogenesis for the defined generation of human pancreatic progenitor and endocrine cell types from human embryonic stem cells (hESCs) that results in the formation of glucose-responsive beta-like cells in vitro. A straightforward schematic comparing the protocol disclosed herein to conventional protocols is provided in FIG. 11. hESC derived beta-like cells exhibit key features of cadaveric human beta cells both in vitro and in vivo, most notably their ability to respond to physiological increases in glucose concentrations by secreting insulin. Gene expression analysis of beta-like cells indicates the presence of factors essential for beta cell function, proper biosynthesis of mature insulin, glucose metabolism, and insulin secretion at levels comparable to human islets (FIG. 5). In addition, beta-like cells display ultrastructural features of bonafide human beta cells, such as appropriate secretory vesicles. Thus, critical elements necessary for the generation and appropriate processing, packaging and storing of insulin in its bioactive mature form are present in these hESC-derived cells. Finally, beta-like cells remained functional after short-term transplantation and reduced blood glucose levels in a murine model of diabetes, further confirming the correct differentiation state of the cells (FIG. 6).

Recently, two other groups have reported the derivation of glucose responsive beta-like cells from hESC cells that share many characteristics of the beta-like cells described herein (Rezania et al, 2014; Pagliuca et al, 2014). Both of these studies, however, focused on optimizing the later stages of direct differentiation, while employing parts of published protocols, namely the addition of RCN, to establish pancreatic progenitor populations. Data disclosed herein demonstrate that generation of pancreatic progenitors using this method also results in the undesirable generation of immature polyhormonal endocrine cells that lack expression of the critical beta cell transcription factor NKX6.1. Indeed, both published studies do note appreciable populations of C-peptide/insulin positive cells that lack NKX6.1 expression. We demonstrate that polyhormonal cells result from precocious endocrine induction in PDX1$^+$ pancreatic progenitors (lacking NKX6.1 expression), which can be avoided by omitting BMP inhibitors during the pancreas specification stage. Further, our detailed analysis of the effects of individual RCN factors on expression of key pancreatic markers revealed that retinoic acid alone is sufficient to induce proficient generation of more than 98% PDX1$^+$ pancreatic progenitors. Subsequent exposure to EGF and KGF results in the rapid and effective activation of NKX6.1 in these cells, generating PDX1$^+$/NKX6.1$^+$ progenitor cells with the ability to give rise to beta-like cells in vitro. These simplified differentiation conditions enable the efficient generation of human pancreatic and more restricted endocrine progenitor populations from pluripotent stem cells without unwanted formation of polyhormonal cells. This simplified differentiation protocol more closely resembles key aspects of early human pancreas development and, as such, represents an improvement over published protocols.

Studies in rodents have shown an important role for Notch signaling in the endocrine differentiation of progenitor cells in vivo. While initially required for the generation of competent progenitor cells, a subsequent reduction of Notch signaling is necessary for the induction of NEUROG3 expression that initiates endocrine differentiation (Shih et al, 2012). In the context of in vitro differentiation, previous studies have shown that direct inhibition of Notch signaling by gamma secretase inhibitors or the use of BMP and TGFβ/ALK inhibitors results in increased insulin expression at later stages (Mfopou et al, 2010; Nostro et al, 2011; Pagliuca et al, 2014; Rezania et al, 2014). We employed BMP and Activin receptor-Like Kinase (ALK) inhibition over a 5-day window to induce NEUROG3 expression specifically in PDX1+/NKX6.1+ progenitors, which resulted in the efficient generation of INS+/NKX6.1+ beta-like cells, while only few polyhormonal cells were observed (about 3%, which is less than 5%). Likely, these unwanted cells originated from the small percentage of PDX1 pancreatic progenitors present at the time of endocrine induction. In contrast to the formation of PDX1+ and PDX1+/NKX6.1+ progenitors that occurs rapidly (36-48 hours after addition of inducing factor(s)) and uniformly in the majority of cells, endocrine differentiation occurs over a prolonged period and is confined to a small subset of total cells. This might be a reflection of the situation observed during normal human pancreas development, where only few progenitor cells initiate the endocrine differentiation program at any given time (Jennings et al, 2013). While simultaneous widespread induction of endocrine differentiation in a majority of PDX1+/NKX6.1+ progenitor population would greatly reduce differentiation time and increase beta-like cell yield, our results point to a regulation of NEUROG3 expression that requires subtle, yet temporally precise, adjustment that appears more complex than just Notch inhibition. As our differentiation protocol allows for a tight control of NEUROG3 expression, it could be used in future studies to identify novel regulators of NEUROG3 gene expression, and ideally to achieve uniform NEUROG3 activation during direct differentiation in vitro.

While cadaveric islet preparations are widely accepted as the gold standard for studying human beta cells, several problems associated with their use remain. For example, their performance and utility depend on a number of confounding factors: genetic variance, age and life style of the donor, isolation time, islet purity and shipping conditions. By eliminating the constraints of availability and reproducibility, we expect hESC-derived beta cells to provide an important therapeutic and a tool to accelerate understanding of the biology of human beta cells.

Without wishing to be bound by theory, the methodology disclosed herein resulted from approaching the problem of engineering fully functional mature β-cells by adopting a developmental perspective that recapitulated an important process in β-cell development unheeded in hPSC differentiations until now: the clustering or coalescence of newly born β-cells observed during islet formation in vivo. Islet formation is initiated towards the end of gestation in humans and rodents, wherein delaminating β-cells, coalesce into small islet-like aggregates that progressively form larger clusters during postnatal development[21]. This period of neonatal growth is coincident with gradual functional maturation of β-cells, which broadly encompasses acquisition of glucose sensing, dense core granule biogenesis, stimulus-secretion coupling, and ultimate metamorphosis into adult β-cells. Consistent with this, incorporating a re-aggregation step permits maturation of in vitro-generated hPSC-derived-β-like cells into eBCs with superior functional properties, including the stereotypical rapid and robust release of C-peptide highly synchronous with glucose concentrations, elevated calcium signaling on glucose stimulation that was ablated on removal of stimulus, highly sensitive K-ATP channels that can be reversibly closed and opened, and mitochondrial energization analogous to adult human islets. Disclosed herein are detailed functional analyses of in vitro hPSC-derived-β-cells, illuminating the remarkable similarity of in vitro-generated islet-like eBCs to human islets. The formation of these alpha and delta cells provides further evidence that the eBCs are capable of inducing the formation of beta islet structures that more closely resemble native human islets, and by structure and functional assay appear to be beta cells capable of providing, or restoring, glucose responsiveness in an organism. Notably, the size (100 μm) of eBCs falls within the range of smaller human islets that have better function in vitro and improved outcome post-transplantation[33]. eBCs function rapidly within a few days (3-days) of transplantation, like human islets, and prevent STZ-induced diabetes in mice. In addition to C-peptide-expressing cells, single-hormone-positive cells expressing glucagon and somatostatin organized in islet-like structures are observed in eBC grafts 48 days following transplantation, further supporting the robust function of eBCs in vivo.

Neonatal β-cells change their transcriptional profile during maturation; expression of 'allowed' genes required for regulated insulin secretion is increased while 'disallowed' housekeeping genes are repressed to circumvent inappropriate function. 'Allowed' genes include those promoting mature β-cell identity such as PDX1, NKX6.1, NEUROD1, ISL1 and PAX6[12, 13, 27, 34]. Greater than 80-90% of cells in eBCs are co-positive for these transcription factors and C-peptide. Moreover, these markers are more strongly expressed in eBCs than immature d20 β-like-cells. Importantly, C-peptide is expressed at higher intensity in eBCs compared with immature d20 β-like cells[16], a finding in line with previous reports of enhanced insulin content in mature β-cells[7, 8]. Of note, eBCs contain high levels of MAFB, but are low in MAFA expression. This is reminiscent of 'juvenile β-cells', which are fully functional, expressing high levels of MAFB for several years before MAFA levels increase[10]. Maturation also increases expression of genes regulating glucose sensing and secretion; these genes are similarly expressed in eBCs and human islets. In particular, SLC30A8, vital for insulin granule maturation and exocytosis[35], is highly enriched in eBCs. Concurrent with increase in genes coding for critical aspects of mature β-cell function, 'disallowed' genes capable of decoupling stimulus-secretion need to fade during maturation. Two such genes, HK1 and LDHA, were examined for repressive DNA methylation marks and found them to be hypermethylated in eBCs in a pattern akin to human islets [9]. Thus, eBCs are functionally mature and equipped to appropriately respond to glucose excursions during meals while remaining inactive during fasting.

Although the relevance of β-cell-cell contacts in human and mouse islet function has been underscored by several reports[36-38], the surprising outcome of clustering immature β-like-cells as disclosed herein was induction of mitochondrial metabolic maturation. β-cells in eBCs were enriched in oxidative metabolic pathways, including OXPHOS, electron transport chain, TCA cycle and ATP biosynthesis when compared with β-cells residing in progenitor-rich environments. We observed increased mitochondrial respiration, mitochondrial mass and differential membrane depolarization on glucose stimulation in β-cells of eBCs. Additionally, cristae in the mitochondrion of these mature β-cells were highly folded and stacked, a noteworthy observation given the recent discoveries linking dynamics of cristae morphology to function of OXPHOS system[31]. The findings disclosed herein are in concert with the transition from glycolysis-centric to OXPHOS-centric metabolism posited to occur during postnatal functional maturation [8, 17, 30, 39], a process that might in part be driven by coalescence of β-cells. Furthermore, clustering resulted in enrichment of ERRγ, a mitochondrial regulator of the metabolic transition, suggesting that re-aggregation activates endogenous processes driving increased mitochondrial activity.

Correlation analysis from RNA-seq experiments unveiled that the hPSC-derived-β-cells are highly similar to primary β-cells (R=0.9253). Nonetheless, differences in expression of certain adult β-cell markers, including MAFA, UCN3 and G6PC2, were found between the two groups. These data are in line with an extended postnatal maturation period in humans lasting through childhood[11] wherein juvenile yet functionally mature β-cells have high expression of MAFB [10] but not MAFA as observed in the disclosed eBCs. Furthermore, emerging data sheds light on heterogeneity within β-cells of human islets, especially indicating the existence of distinct populations of β-cells with distinguishable functional capabilities. On closely comparing the ex vivo-generated β-cells with four β-cell subtypes described by Dorrell et al.[40], the cells were found to be CD9low and ST8SIA1low, and hence probably represent β1-subtype, the most abundant and glucose-responsive β-cell subtype. On the contrary, there was no enrichment of Fltp/Cfap126, a marker separating mature β-cells from replication competent β-cells in mice[41], in the mature fully functional β-cells compared with immature β-cells. Interestingly, Fltp/Cfap126 was also reported to increase upon endocrine cell clustering and compaction in that study. Although not Fltp/Cfap126, the RNA-seq results provided herein revealed enrichment of other cilia- and flagella-associated proteins, namely Cfap20, Cfap36 and Cfap97, in the mature versus immature hPSC-derived-β-cells ($p<0.05$).

In summary, clustering/re-aggregation of immature β-like-cells has been demonstrated herein to be an important step in the maturation and generation of fully functional β-cells from hPSCs, in vitro. Our data strongly indicate that coalescence of immature β-like cells induces metabolic maturation of mitochondria capable of generating the necessary ATP currency for mature β-cell function such as insulin synthesis, packaging and exocytosis. This improved protocol provides the methodology for hPSC-derived-β-cell therapeutics for diabetes and delivers a cell type equivalent, if not identical, to human β-cells for such therapy as well as drug discovery and disease modeling.

Taken together, the fast and simplified protocol disclosed herein provides precise temporal control over the generation of subsequent pancreatic progenitor and endocrine cell types and results in the establishment of human beta-like cells that exhibit glucose responsiveness in vitro and in vivo. The suspension-based direct differentiation approach is scalable, and the ability to produce large numbers of beta-like cells provides a safe and effective cell therapy to patients suffering from diabetes. Furthermore, through the production and maintenance of different developmental cell populations, the approach can be used for more detailed investigations into human pancreas development and human beta cell function that were previously impossible due to limited donor material, such as large scale drug screens and genome-wide gene function studies.

The following examples illustrate embodiments of the disclosure.

Example 1

Materials and Methods
Cell Culture
Undifferentiated MEL1 INS$^{GFP}$/w reporter cells (Micallef et al, 2012) were maintained on mouse embryo fibroblast feeder layers (Millipore) in hESC media as described (Guo et al, 2013b). Suspension-based differentiations were carried out as follows. Briefly, confluent cultures were dissociated into single cell suspension by incubation with TrypLE (Gibco). Cells were counted and each well of 6-well low-adherence plates were seeded with $5.5\times10^6$ cells in 5.5 ml hES media supplemented with 10 ng/ml Activin A (R&D systems) and 10 ng/ml HeregulinB1 (Peprotech). Plates were placed on an orbital shaker at 100 rpm to induce sphere formation, as described (Schulz et al, 2012). To induce definitive endoderm differentiation, aggregates were collected 24 hours later in a 50 ml falcon tube, allowed to settle by gravity, washed once with PBS and re-suspended in d1 media (RPMI (Gibco) containing 0.2% FBS, 1:5000 ITS (Gibco), 100 ng/ml Activin A, and 50 ng/ml WNT3a (R&D systems)). Clusters from 3 wells were combined into 2 wells at this point and distributed into fresh low-attachment plates in 5.5 ml d1 media. Media thereafter was changed daily, by removing either 4.5 ml media (at the end of d1) or 5.5 ml media the following days and adding back 5.5 ml fresh media until day 9. After day 9, only 5 ml of media was removed and added daily.

Differentiation employing published protocols has been described (Schulz et al, 2012; Rezania et al, 2012). Media in our simplified differentiation protocol consists of, d2: RPMI containing 0.2% FBS, 1:2000 ITS, and 100 ng/ml Activin A; d3: RPMI containing 0.2% FBS, 1:1000 ITS, 2.5 µM TGFbi IV (CalBioChem), and 25 ng/ml KGF (R&D systems); d4-5: RPMI containing 0.4% FBS, 1:1000 ITS, and 25 ng/ml KGF. d6-7: DMEM (Gibco) with 25 mM Glucose containing 1:100 B27 (Gibco), 3 nM TTNBP (Sigma); d8: DMEM with 25 mM Glucose containing 1:100 B27, 3 nM TTNBP, and 50 ng/ml EGF (R&D systems); d9: DMEM with 25 mM Glucose containing 1:100 B27, 50 ng/ml EGF, and 50 ng/ml KGF. d10-14: DMEM with 25 mM Glucose containing 1:100 B27, 500 nM LDN-193189 (Stemgent), 30 nM TATA-Binding Protein (TBP; Millipore), 1000 nM Alki II (Axxora), and 25 ng/ml KGF; d15-21: DMEM with 2.8 mM Glucose containing 1:100 Glutamax (Gibco) and 1:100 NEAA (Gibco). Human islets were from Prodo Laboratories or the UCSF Islets and Cellular Production Facility.

Mice
NOD.Cg-Prkdcscid Il2rgtm1 Wjl/SzJ mice (NSG) were obtained from Jackson Laboratories. Mice used in this study were maintained according to protocols approved by the University of California, San Francisco Committee on Laboratory Animal Resource Center. For kidney capsule grafts, approximately $5.0\times10^6$ hESC differentiated cells in spheres and 4000 human islet equivalents were transplanted as described (Russ & Efrat, 2011; Szot et al, 2007). For glucose-induced insulin secretion, mice were fasted overnight and serum was collected before and after intraperitoneal administration of 3 g/kg D-glucose solution. For induction of diabetes, mice were administered 35 mg/kg streptozotocin via intraperitoneal injection for 5 days. Graft bearing kidneys were removed for immunofluorescence analysis. No statistical method was employed to determine sample size, mice were not randomized and analysis was not blinded.

Cell Sorting and Flow Cytometric Analysis
Briefly, spheres were collected and allowed to settle by gravity. Clusters were washed once in PBS and dissociated by gentle pipetting after 12-15 minutes incubation in Accumax (innovative cell technologies). For sorting, cell suspension were filtered and re-suspended in FACS buffer consisting of phosphate-buffered saline (PBS) (UCSF cell culture facility) containing 2 mM EDTA (Ambion) and 1% BSA (Sigma). Dead cells were excluded by DAPI (Sigma) staining. Cell sorting was performed on a FACS Aria II (BD Bioscience). For flow-based analysis, dissociated cells were fixed with 4% paraformaldehyde (Electron Microscopy Science) for 15 minutes at room temperature, followed by two washes in PBS. Samples were either stored at 4 C or immediately stained with directly conjugated antibodies. Data analysis was performed with FlowJo software. Mouse Glucagon and mouse human C-peptide antibodies were conjugated in-house by the UCSF Antibody Core and/or with Antibody Labeling Kits (Molecular Probes) according to manufacturer's instructions. Commercially available directly conjugated antibodies, i.e., antibodies Human PAX6-Alexa647, Islet-1-PE, NKX6.1-Alexa647, NKX6.1-PE, ChromograninA-PE, NeuroD1-Alexa647, PDX1-PE, and Ki67-Alexa647, were from BD Bioscience.

Electron Microscopic Analysis

Spheres were fixed by adding 37° C. 0.1M sodium cacodylate solution (Sigma) containing 2% paraformaldehyde (Electron Microscopy Science) and 2.5% glutaraldehyde (Electron Microscopy Science), 3 mM $CaCl_2$ (Sigma), final pH 7.4. Spheres were then transferred to 4° C. for approximately 18 hours, followed by standard processing and analysis by the Electron Microscope Lab/Diabetes Center Microscope Core.

Immunofluorescence Analysis

Spheres were fixed for 15-30 minutes at room temperature with 4% paraformaldehyde, followed by multiple washes in PBS. Whole mount staining was performed in suspension, by first blocking overnight at 4° C. in blocking buffer consisting of CAS-block (Invitrogen) with 0.2% TritonX (Fisher). Primary antibodies were incubated overnight at 4° C. in blocking buffer, followed by washes in PBS containing 0.1% Tween-20 (PBS-T, Sigma) and incubation in appropriate secondary antibodies diluted in PBS-T overnight at 4° C. The next day, clusters were washed in PBS-T followed by PBS and mounted with Vectashield (Vector) on glass slides. For sectioning of clusters, spheres were embedded in 2% Agar (Sigma), followed by dehydration, paraffin embedding, and sectioning. Cut sections were rehydrated and treated with an antigen retrieval solution (Biogenex) before incubation with primary antibodies overnight at 4° C. in blocking buffer. The next day, sections were washed 3 times in PBS-T and incubated with appropriate secondary antibodies for 30-40 minutes at room temperature in PBS-T. Appropriate Alexa-conjugated secondary antibodies were purchased from JAX or Molecular Probes and used at 1:500 dilutions. Slides were washed in PBS-T and PBS before mounting in Vectashield. Nuclei were visualized with DAPI. Images were acquired using a Leica SP5 microscope or a Zeiss ApoTome. Primary antibodies were employed as indicated in Table 1.

TABLE 1

| Antigen | Species | Dilution | Manufacturer |
| --- | --- | --- | --- |
| Human C-peptide | Mouse | 1:200 | Chemicon |
| Human C-peptide | Rat | 1:1000 | DSHB |
| Insulin | Mouse | 1:1000 | Sigma |
| Insulin | Guinea pig | 1:500 | DAKO |
| Glucagon | Mouse | 1:1000 | Sigma |
| NKX6.1 | Mouse | 1:100 | DSHB |
| NKX2.2 | Mouse | 1:20 | DSHB |
| PDX1 | Goat | 1:200 | R&D systems |
| Human NEUROG3 | Sheep | 1:300 | R&D systems |
| Ki67 | Rabbit | 1:100 | NovoCastra | qPCR Analysis

Total RNA was isolated with TRIZOL (Sigma) or micro/mini RNAeasy kit (Qiagen) and reverse transcribed using the iScript cDNA Kit (Bio-Rad) according to manufacturer's instructions. qPCR analysis was performed on an ABI 7900 HT Fast Real-Time PCR System (Applied Biosystems) and CFX Connect Real Time System (Biorad) using standard protocols. Primers were Taqman Probes (Applied Biosystems) and/or as published previously (Liu et al, 2014). P-values were calculated using a two-tailed student's t-test.

Content Analysis

Insulin, human C-peptide and proinsulin analyses were performed by measuring an aliquot of acidic ethanol lysed clusters with commercially available ELISA kits (Insulin Cat. 80-INSMR-CH10, human C-peptide cat. 80-CPTHU-CH01, and proinsulin Cat. 80-PINHUT-CH01; all from Alpco). Total DNA was quantified by PicoGreen (Invitrogen) assay and normalized to the percentage of C-peptide-positive cells in each sample.

Western Blotting for Proinsulin/Insulin:

Cell lysates were resolved on 4-12% acrylamide gradient SDS-PAGE gels (NuPAGE, Invitrogen) normalized to cellular DNA (Quant-iT dsDNA, Molecular Probes). The samples were then electrotransferred to nitrocellulose membranes and immunoblotted with guinea pig anti-insulin, which recognizes both proinsulin and insulin, as previously described (Haataja et al, 2013). Immunoblotting with anti-tubulin was used as a confirmatory loading control. HRP-conjugated secondary antibodies (Jackson ImmunoResearch) were used for enhanced chemiluminescence detection (Millipore). The analysis was performed four times with isolated human islets used as a positive control.

Glucose Stimulated Insulin Secretion

Human islets or hES-derived spheres were transferred into tubes and washed twice with Krebs-Ringer Bicarbonate buffer (KRB) containing 2.8 mM Glucose. Samples were incubated for one hour in 2.8 mM glucose containing KRB to allow equilibration of cells. The 2.8 mM buffer was removed and replaced with fresh KRB containing 2.8 mM glucose for one hour followed by incubation for another hour in KRB containing 16.7 mM glucose. After the incubation period, buffers were collected for human C-peptide-specific ELISA analysis using a commercially available kit (Alpco).

Additional Materials and Methods Used in Examples 8-13

Cell Culture

Mel1 Ins-GFP human embryonic stem cells were maintained and propagated on mouse embryonic fibroblasts (MEFs) in hESC media. The cells were passaged by enzymatic dissociation using TrypLE (Gibco). To initiate differentiation, confluent hESC cultures were dissociated into single-cell suspension using TrypLE, counted and seeded at $5.5 \times 10^6$ cells/well in 6-well suspension plates in 5.5 ml hESC media supplemented with 10 ng/ml Activin A (R&D Systems) and 10 ng/ml hereguinB (Peprotech). The plates were incubated at 37° C. and 5% $CO_2$ on an orbital shaker at 100 rpm to induce 3D sphere formation. After 24 hours, the spheres were collected in 50 ml falcon tubes, allowed to settle by gravity, washed once with PBS and resuspended in day 1 media. The resuspended spheres in day 1 media were distributed into fresh 6-well suspension plates with 5.5 ml of media/well. Thereafter, media was changed every day. Until day 3, spheres were fed by removing 5 ml of media and replenishing with 5.5 ml of fresh media. From day 4 until day 20, 4.5 ml media was removed and 5 ml of fresh media was added. Media compositions are as follows: Day 1: RPMI (Gibco) containing 0.2% FBS, 1:5,000 ITS (Gibco), 100 ng/ml activin A, and 50 ng/ml WNT3a (R&D Systems). Day 2: RPMI containing 0.2% FBS, 1:2,000 ITS, and 100 ng/ml activin A; Day 3: RPMI containing 0.2% FBS, 1:1,000 ITS, 2.5 µM TGFbi IV (CalBioChem), and 25 ng/ml KGF (R&D Systems); Day 4-5: RPMI containing 0.4% FBS, 1:1,000 ITS, and 25 ng/ml KGF; Day 6-7: DMEM (Gibco) with 25 mM glucose containing 1:100 B27 (Gibco), 3 nM TTNBP (Sigma); Day 8: DMEM with 25 mM glucose containing 1:100 B27, 3 nM TTNBP, and 50 ng/ml EGF (R&D Systems); Day 9-11: DMEM with 25 mM glucose containing 1:100 B27, 50 ng/ml EGF, and 50 ng/ml KGF; Day 12-20: DMEM with 25 mM glucose containing 1:100 B27, 1:100 Glutamax (Gibco), 1:100 NEAA (Gibco), 10 µM ALKi II (Axxora), 500 nM LDN-193189 (Stemgent), 1 µM Xxi (Millipore), 1 µM T3 (Sigma-Aldrich), 10-2000 µM (e.g., 0.5 mM) vitamin C, 1 mM N-acetyl cysteine (Sigma-Aldrich), 10 µM zinc sulfate (Sigma-Aldrich) and 10 µg/ml of heparin sulfate. Day 20: The spheres were collected, incubated with Accumax briefly and dissociated into single cells for flow cytometry. Live GFPhigh cells were sorted on Aria II at low flow rates and re-aggregated in Aggrewell™ 400 plates (StemCell Technologies) at 1,000 cells/cluster in CMRL containing 1:100 B27 (or 10% FBS), 1:100 Glutamax (Gibco), 1:100 NEAA (Gibco), 10 µM ALKi II (Axxora), 0.5 mM vitamin C, 1 µM T3 (Sigma-Aldrich), 1 mM N-acetyl cysteine (Sigma-Aldrich), 10 µM zinc sulfate (Sigma-Aldrich) and 10 µg/ml of heparin sulfate. Day 22-23: The re-aggregated enhanced Beta-clusters (eBCs) were transferred from Aggrewells into 6-well suspension plates and placed on orbital shakers at 100 rpm. From day 23 onwards, eBCs were maintained in 6-well suspension plates until the end of the experiment. Media was changed every third day following re-aggregation. Human islets used in the experiments were obtained from the UCSF Islet Core. They were used for functional and RNA-seq analysis within 24-48 hours of isolation.

Immunofluorescent Staining

Clusters were fixed with 4% PFA for 15 minutes at room temperature, washed with PBS, and stored at 4° C. until processing for paraffin sectioning. Clusters were first embedded in 2% agar, followed by dehydration, paraffin embedding, and sectioning at 5 µm thickness. Cut sections were then stained according to the protocol described previously (Russ et al., EMBO J 2015). Primary antibodies employed are detailed in Table 2. Secondary antibodies were conjugated AlexaFluors 488, 568 and 647 (Molecular probes) of appropriate species, and were used at 1:500 dilution. Cells were counterstained with DAPI to mark nuclei. Slides were mounted with coverslips using Prolong® Diamond Antifade reagent (Invitrogen). Images were generated using a Leica SP5 confocal microscope or a Zeiss apotome.

TABLE 2

| Antigen | Species | Dilution | Manufacturer |
|---|---|---|---|
| Human C-peptide | Mouse | 1:200 | Chemicon |
| Human C-peptide | Rat | 1:1000 | DSHB |
| Insulin | Mouse | 1:1000 | Sigma |
| Insulin | Guinea pig | 1:500 | DAKO |

TABLE 2-continued

| Antigen | Species | Dilution | Manufacturer |
|---|---|---|---|
| Glucagon | Mouse | 1:1000 | Sigma |
| NKX6.1 | Mouse | 1:100 | DSHB |
| NKX2.2 | Mouse | 1:20 | DSHB |
| PDX1 | Goat | 1:200 | R&D systems |
| SOX9 | | | |
| Amylase | | | |
| CK19 | | | |

Flow Cytometry

Clusters at indicated stages were dissociated, fixed, permeabilized and stained for various intracellular markers for quantitative analysis on LSRFortessa X20 Dual, as described previously Russ et al., EMBO J 2015). Data were analyzed with FlowJo software. Anti-Glucagon and anti-human C-peptide antibodies were conjugated in-house using the Molecular Probes Antibody Labeling Kits according to manufacturer's instructions. Antibody details are listed in Table 3.

TABLE 3

| Antibody | Manufacturer |
|---|---|
| Human PAX6-Alexa647 | BD Bioscience |
| Islet-1-PE | BD Bioscience |
| NKX6.1-Alexa647 | BD Bioscience |
| NKX6.1-PE | BD Bioscience |
| ChromograninA-PE | BD Bioscience |
| NeuroD1-Alexa647 | BD Bioscience |
| PDX1-PE | BD Bioscience |

Quantitative Real-Time PCR

Human islets and hPSC-derived clusters were harvested at indicated stages of differentiation by homogenization in TRIzol (Invitrogen) or Buffer RLT (Qiagen), and RNA was isolated and purified using RNeasy Mini/Micro kits (Qiagen). qPCR was performed using gene expression assays from Applied Biosystems. Thermo Fisher Scientific Taqman Assay identifications are given in Table 5 in Example 10. The comparative threshold ($\Delta\Delta CT$) method was used to quantify transcript abundance.

Dynamic Insulin Secretion Assay

An in-house built perifusion system was used for dynamic secretion assays. Twenty-thirty hPSC-derived clusters or human islets were placed on 10 µm TCTP filters (Isopore™ membrane) in plastic chambers that were immersed in a 37° C. water bath. Under temperature- and $CO_2$-controlled conditions, the clusters were perifused at 1 ml/minute with Krebs-Ringer buffer (KRB) using a peristaltic pump (Isomatec IPC). After an initial hour-long preincubation in 2.8 mM KRB, alternating low (2.8 mM) and high (20 mM) glucose and 30 mM KCL were perfused through the system. Flow-through was collected over the course of the experiment, and C-peptide levels were measured using the STELLUX® Chemi Human C-peptide ELISA kit (Alpco). After the experiment, clusters/islets were recovered from the membrane and their insulin and DNA content were measured by acid-ethanol extraction and Quant-iT PicoGreen dsDNA Assay Kit, respectively.

Islet Perifusion and Imaging for Calcium Flux and Mitochondrial Depolarization Analysis All imaging and perifusion experiments were conducted according to previously described methods (Adewala et al., Biomed. Microdevices 12:409-417, 2010; Shaikh et al., Lab on a Chip 9:97-106, 2009). In brief, hPSC-derived clusters and islets were incubated in 2 mL of Krebs buffer containing both 5 μM Fura-2/AM and 2.5 μM Rhodamine 123 fluorescent dyes (Molecular Probes, Calif.) for 30 minutes prior to loading the device. The islets were then loaded into the temperature-equilibrated microfluidic device mounted on an inverted epifluorescence microscope (Leica DMI 4000B, location). Dual-wavelength Fura-2/AM was excited at 340 and 380 nm and fluorescent emission was detected at 510 nm. Intracellular $Ca^{2+}$ was expressed as a ratio of fluorescent emission intensity F340/F380(%). Rh123 was excited at 490±10 nm, and emission was measured at 530±10 nm. Fura-2 and Rh123 fluorescence emission spectra were filtered using a Fura-2/FITC polychroic beamsplitter and double band emission filter (Chroma Technology. Part number: 73100bs). These images were collected with a CCD (Retiga-SRV, Fast 1394, QImaging). SimplePCI software (Hamamatsu Corp. location) was used for image acquisition and analysis. Both fluorescence signals were expressed as "change-in-percentage" after being normalized against basal intensity levels established before stimulation.

RNA-Sequencing Library Preparation and Data Analysis

Total RNA was isolated from d27 eBCs and Unsorted-Reagg clusters; GFP-high cells FACS sorted from d27 eBCs and Unsorted-Reagg clusters and d20 immature clusters; and β-cells FACS sorted from adult human islets using RNeasy Micro kits (Qiagen). RNA isolated from sorted cells was further concentrated employing RNA Clean & Concentrator (Zymo research). Only RNA samples with an RNA Integrity Number (RIN) >7 were used to generate libraries for deep sequencing. Ribosomal RNA (rRNA) was depleted by Ribo-Gone (Clontech), and 325-350 bp-sized strand-specific cDNA libraries were prepared using the SMARTer Stranded Total RNA Sample Prep Kit—Low Input Mammalian Kit (Clontech). The samples were further sequenced on an Illumina HiSeq 4000 instrument generating paired-end 100-base-pair reads. Read qualities were assessed by the FASTQC tool on Galaxy. Reads were then mapped to the human genome (hg38) using TopHat version 2.1.0 (Trapnell, et al., Bioinformatics 25:1105-1111, 2009) using the corresponding sample's mean inner distance between mate pairs, library-type fr-firststrand for strand determination leaving other parameters at default settings. The tuxedo suite tools were used for further analysis: rRNA and tRNA reads were masked during transcript assembly using Cufflinks and differential expression analysis was performed using Cuffdiff. Seeking an unbiased approach to pathway analysis, we used the Gene set enrichment analysis (GSEA) tool developed by Broad Institute (Mootha et al., Nat. Genet. 34:267-273, 2003; Subramanian et al., PNAS 102:15545-15550, 2005) that identifies groups of coordinately regulated genes present in gene sets annotated in the Molecular Signatures Database (MSigDB). The ranking metric used was 'tTest', number of permutations employed was 1000 and MSigDB collections used were hallmark gene sets, curated gene sets such as KEGG, and GO gene sets such as biological process, molecular function and cellular component. The program R was used to plot scatter plots and calculate correlation coefficients. The online tool Morpheus, from the Broad Institute, was used to generate heatmaps and perform hierarchical clustering.

Bisulfite Sequencing

DNA samples were bisulfite-converted and purified using the Epitect Plus kit (Qiagen). Bisulfite-treated DNA was used as template to amplify the regions of interest using the bisulfite-converted DNA primers described previously (Dhawan et al., J. Clin. Invest. 125:2851-2860, 2015). Annealing temperatures were 64° C. for HK1 and 61° C. for LDHA using KAPA HiFi Uracil+ DNA polymerase and ReadyMix. PCR products were gel purified and used for TOPO-TA cloning (Invitrogen), followed by Sanger sequencing. Bisulfite sequencing data were aligned and analyzed using the Sequencher software. In the resulting data, each line of the diagram represents one clone and 8-10 clones were analyzed per sample. Filled circles represent methylated CpGs and open (white) circles represent unmethylated ones.

Electron Microscopy

Clusters were spun down and excess media was removed, followed by addition of ice-cold fixative (0.1 M sodium cacodylate solution containing 2% paraformaldehyde and 2.5% gluteraldehyde, 3 mM $CaCl_2$, final pH 7.4) and incubation on ice for 20 minutes. The clusters were further processed using standard transmission electron microscopy procedures and analyzed by the Gladstone Electron Microscopy Core.

In Vitro Metabolic Flux Analysis

Mitochondrial oxygen consumption rate (OCR) and extracellular acidification rate (ECAR) were measured in real time using an XFe24 extracellular flux analyzer (Seahorse Bioscience). hPSC-derived clusters and human islets were first rinsed with pH-adjusted (7.4) XF base media (sodium bicarbonate-free) supplemented with 3 mM glucose. Twenty-thirty clusters/islets were placed per well of an islet plate and each experiment had two replicates per group. This was followed by insertion of a mesh to prevent movement of clusters during the assay and incubation in a non-$CO_2$ incubator at 37° C. for at least one hour. Three baseline measurements were taken, following which glucose (2.8 or 20 mM), Oligomycin (5 μM), carbonyl cyanide-4-(trifluoromethoxy) phenylhydrazone (FCCP, 1 μM), and rotenone and antimycin A (5 μM) were injected sequentially. OCR and ECAR were measured at 37° C. in real time throughout the assay period. OCR and ECAR were normalized to average baseline measurement and expressed as percent change during the course of the experiment. The insulin content of each well was also determined by STELLUX® Chemi Human C-peptide ELISA kit (Alpco).

Mitochondria Experiments

For estimation of mitochondrial mass, dissociated cell populations were incubated in warm media containing MitoID at a dilution of 1:10,000 for one hour at 37° C. with gentle shaking. Following washes with PBS, dissociated cells were fixed with 4% PFA, stained with anti-C peptide and anti-NKX6.1 antibodies and analyzed on LSRFortessa X20 Dual (BD Biosciences). For estimation of mitochondrial membrane potential, MitoTracker Red CM-H2XRos (Thermo Fisher Scientific), a mitotracker dye that fluoresces only on oxidation in live cells, was used. Dissociated cell populations were incubated with 500 nm MitoTracker Red CM-H2XRos in KRB containing either 2.8 or 20 mM glucose for one hour at 37° C. with gentle shaking. Cells were fixed and further stained with antibodies against C-peptide and NKX6.1 before FACS analysis. For measuring mitochondrial DNA copy number, DNA was isolated from indicated cell populations using QIAamp DNA Micro Kit (Qiagen). qPCR was used to determine the ratio of mitochondrial mtDNA 16S rRNA gene to nuclear ß-2-microglobulin (B2M) gene using SYBR Green (Roche) based detection. Human specific primers used for mtDNA 16S rRNA were: 5'-GCCTTCCCCCGTAAATGATA-3' (SEQ ID NO:1) and 5'-TTATGCGATTACCGGGCTCT-3' (SEQ ID NO:2), and for B2M were: 5'-TGCTGTCTCCATGTTTGATGTATCT-3' (SEQ ID NO:3) and 5'-TCTCTGCTCCCCACCTCTAAGT-3' (SEQ ID NO:4).

Mouse Studies

NOD.Cg-Prkdcscid Il2rgtm1Wjl/SzJ mice (NSG) were obtained from Jackson Laboratories and bred in the facility at the University of California, San Francisco. Male mice between the age group of 10-16 weeks were used in this study and were maintained according to protocols approved by the University of California, San Francisco, Institutional Animal Care and Use Committee. Mice were anaesthetized with isoflurane and transplanted with eBCs under the kidney capsule. Two cohorts of mice were transplanted with 700 eBCs (about 700,000 cells) and one cohort received 4000 eBCs (about $4 \times 10^6$ cells). For in vivo glucose challenge experiments, mice were fasted overnight, and serum was collected by sub-mandibular bleeding before, and 30 minutes following, an intraperitoneal injection of 2 g/kg D-glucose solution. Kidneys bearing grafts were removed at indicated time points for immunofluorescent and H&E staining. For determining the ability of the grafts to protect against diabetes, age-matched control and eBC-transplanted mice were injected with multiple low-doses of STZ (35 mg/kg/d for 5 days), and monitored for hyperglycemia. Control mice that were overtly diabetic either died or had to be euthanized. A survival nephrectomy was performed to remove the grafts 50 days after transplant, following which blood glucose levels of the mice were monitored.

Statistical Analyses

Statistical tests performed for specific data are described in the brief descriptions of the corresponding figures. In brief, under the assumption of normal distribution, two-tailed unpaired t-tests (Student's t-test) were used if standard deviation (SD) was equal or two-tailed unpaired t-tests with Welch's correction were used if SD was unequal to compare various groups in FIG. 21D, FIG. 22C-D, and FIG. 24E. All statistical tests were performed in GraphPad Prism Software v7. Statistical methods were not used to determine sample size. Investigators were blinded to the treatment groups in calcium signaling, mitochondrial depolarization and DNA methylation experiments.

Example 2

Pancreatic Differentiation of hESCs Using a Large-Scale Culture System Results in Two Distinct Subsets of Insulin-Producing Cells.

To generate pancreatic beta-like cells from human PSC, we established a scalable three-dimensional suspension culture system based on previously reported methods (Schulz et al, 2012; Rezania et al, 2012) (FIG. 1A). To monitor the generation of live insulin-producing cells and facilitate their isolation, we employed the recently published $INS^{GFP/W}$ reporter cell line (Micallef et al, 2012) in which green fluorescence protein (GFP) expression is under the control of the endogenous insulin promoter. Using this differentiation protocol, GFP reporter expression was readily observed at day 13 and increased thereafter, resulting in an average of 37±8% GFP positive cells between days 19-24 (FIG. 1B-D). The validity of GFP as an accurate substitute for insulin was verified by staining with an insulin-specific antibody, which revealed an even higher percentage of insulin-producing cells (up to 60%) likely due to delayed accumulation of the fluorescence marker (FIG. 1E). Similar results were obtained with an antibody specific to human C-peptide, excluding antibody reactivity due to insulin uptake from culture media (FIG. 1E). Co-staining for human C-peptide and glucagon (GCG), a hormone normally produced by alpha cells, showed that 4.3% and 13.2% of all cells exhibited a polyhormonal phenotype at day 13 and day 19, respectively (FIG. 1F). Co-staining for C-peptide and NKX6.1 at day 20 indicated the presence of some double positive beta-like cells (FIG. 1G). Quantitative flow cytometry analysis revealed that the proportion of INSULIN and NKX6.1 double-positive beta-like cells increased from less than 2.5% at day 13 to approximately 12% cells at day 19 of total cells (FIG. 1G). Ultrastructural analysis of differentiated cultures showed cells containing secretory vesicles with an electron dense core surrounded by an electron light halo (FIG. 1H), a morphology reminiscent of insulin vesicles that are found in human beta cells. The majority of cells, however, exhibited a mixture of secretory granules usually found in non-beta cells of human pancreas preparations (FIG. 1H). Thus, differentiation experiments employing published protocols (Schulz et al, 2012; Rezania et al, 2012) result in the efficient generation of two distinct insulin-producing cell populations: $INS^+$ cells that do not co-express the critical TF NKX6.1 and manifest as polyhormonal cells, and $INS^+/NKX6.1^+$ beta-like cells that more closely resemble human beta cells. Notably, $INS^+/NKX6.1^+$ beta-like cells are absent from cultures at earlier time points but appear and increase in number at later stages of differentiation, indicating that they are derived from a distinct progenitor cell type.

Example 3

Defining the Temporal Activities of Individual Signaling Factors to Efficiently Generate $PDX1^+$ and $PDX1^+/NKX6.1^+$ Pancreas Progenitor Populations while Preventing Precocious Induction of Endocrine Differentiation.

Figure 2:
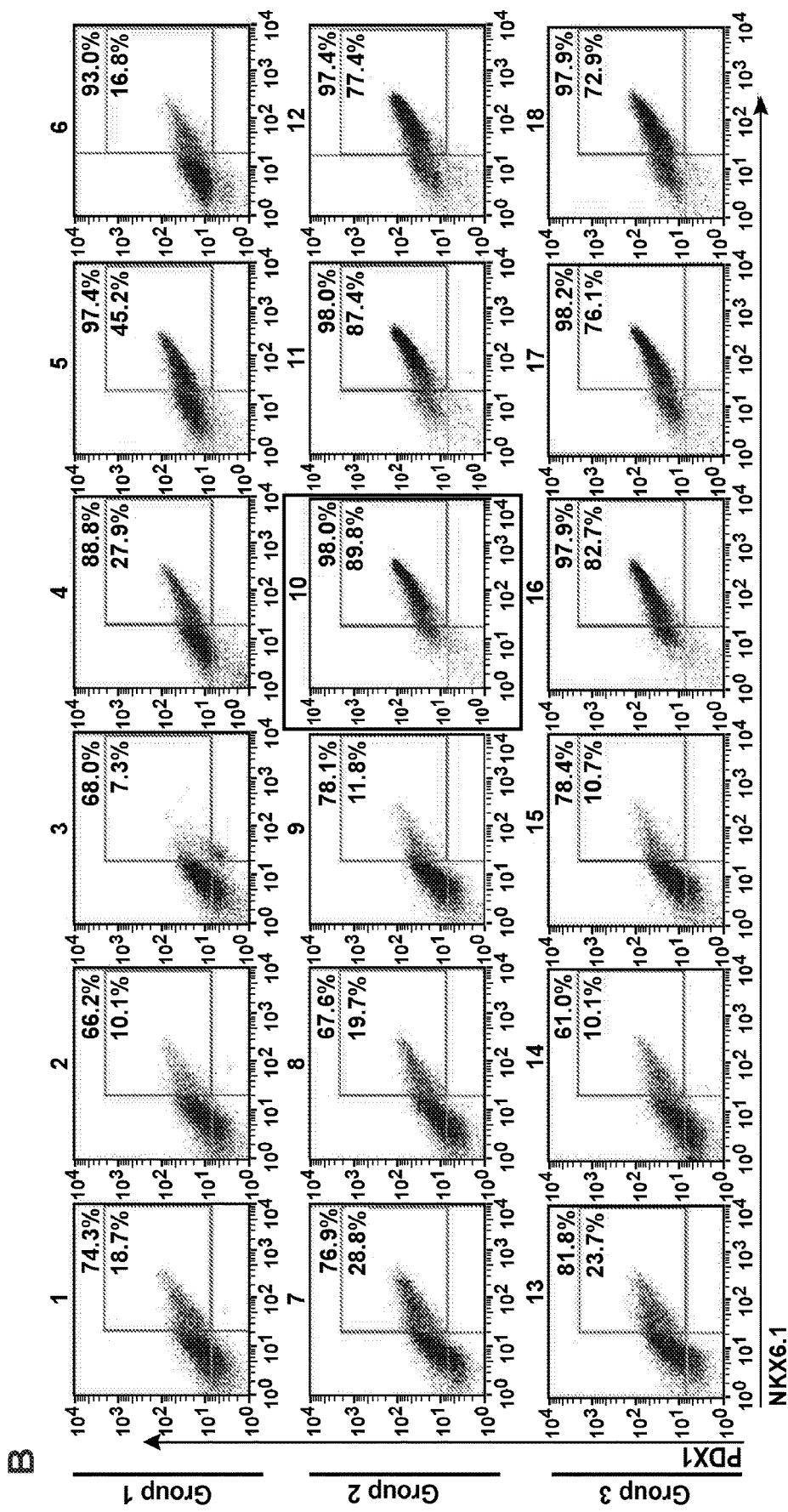
FIG. 2. Defining the temporal activities of individual signaling factors to efficiently generate PDX1$^+$ and PDX1$^+$/NKX6.1$^+$ pancreas progenitor populations while preventing precocious induction of endocrine differentiation. A-C: Pancreatic progenitor marker expression at day 9.5 after treatment with conventional differentiation factors alone or in different combinations. Treatments consisted of combinations of Cyclopamine (C), Noggin (N), and retinoic acid (R) during days 6-8, followed by subdivision of each condition into three treatment groups during day 9-9.5. Group 1) continuation of day 6-8 treatment; Group 2) treatment with EGF and KGF (EK); Group 3) treatment with EGF, KGF, and Noggin (EKN). The condition selected for further studies, '10', is marked with a green box. Data shown are representatives of results obtained in two independent experiments. A: Table detailing 18 different culture conditions that were evaluated. B: Quantification of PDX1 (orange gate) and NKX6.1 (blue gate) protein expressing cells in individual conditions after 9.5 days of differentiation. C: NKX6.1 and NEUROG3 protein expression assessed by whole mount staining of differentiated clusters at 9.5 days. Note robust NEUROG3 expression in all clusters exposed to N (conditions 3, 6, 9, and 12-18).
Figure 2:
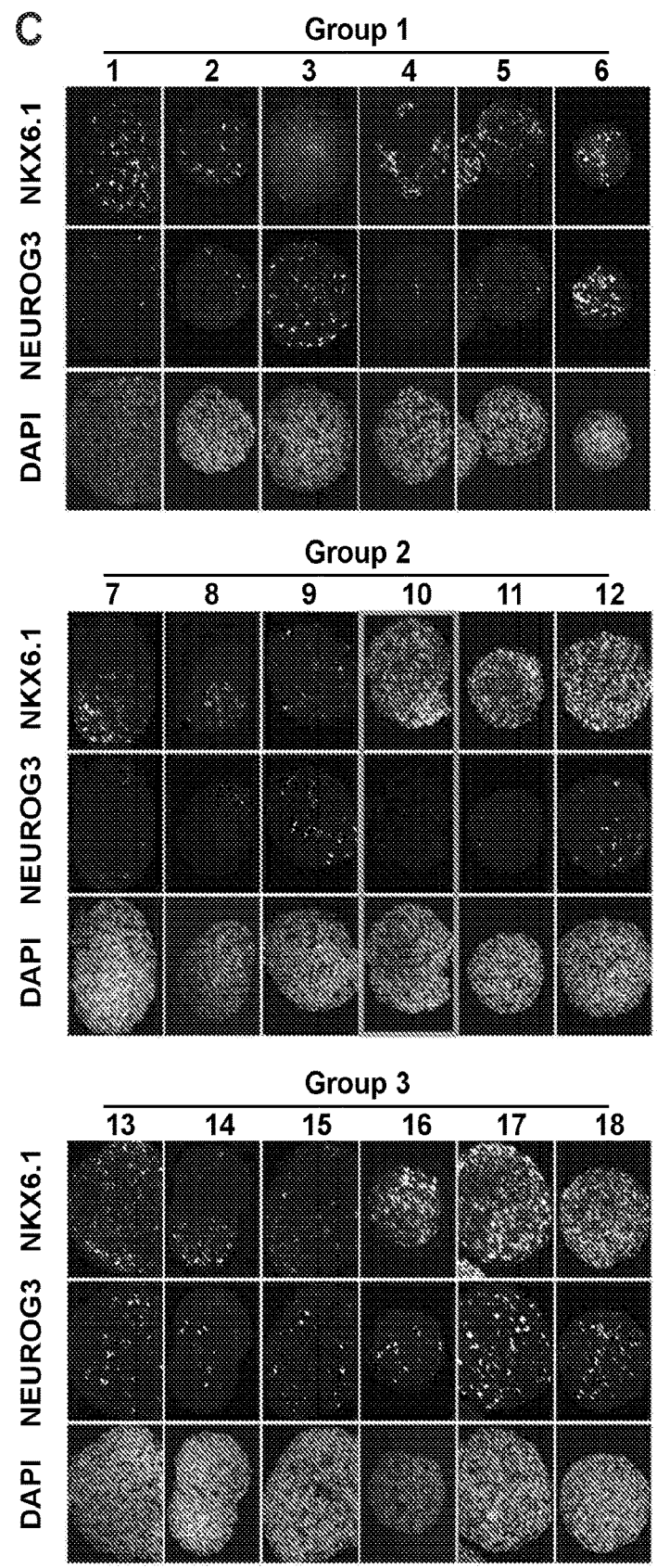
Figure 7:
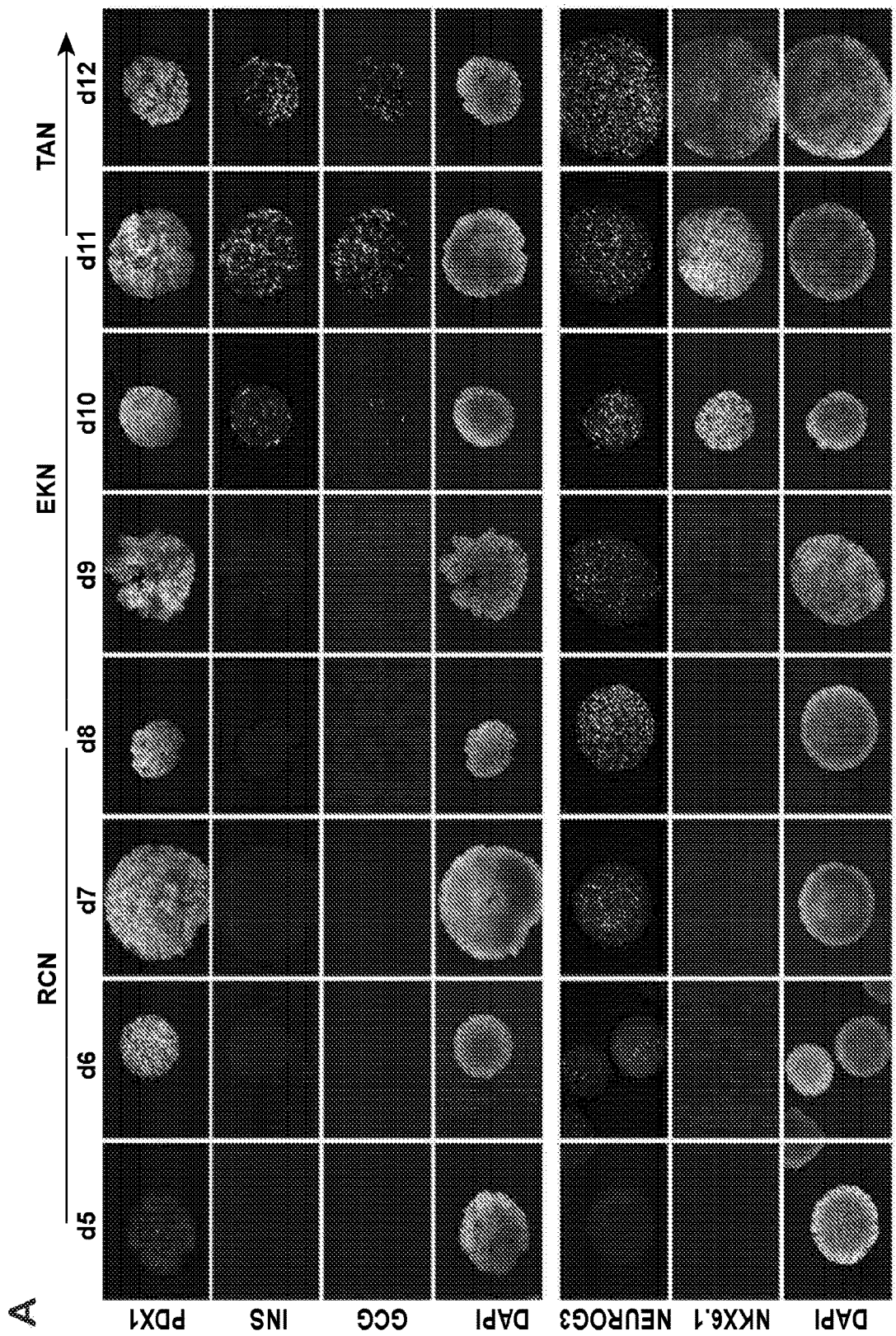
FIG. 7. Published protocols result in precocious endocrine differentiation by NEUROG3 activation. A-C: Analysis of key pancreatic progenitor markers in clusters differentiated as outlined in FIG. 1A. R=Retinoic acid, C=Cyclopamine, N=Noggin, E=Epidermal growth factor, K=Keratinocyte growth factor, T=TBP, and A=ALK inhibitor. Data shown are representative of two independent experiments. A: PDX1, INS, GCG, NEUROG3, and NKX6.1 protein expression was assessed by whole mount staining of differentiated clusters at indicated time points. Note precocious expression of the endocrine marker NEUROG3 in the absence of NKX6.1 protein at days 6-9. B and C: Flow cytometric quantification of PDX1$^+$ (orange gate), PDX1$^+$/NKX6.1$^+$ (blue gate), INS$^+$/NKX6.1$^+$ (green gate), and INS$^+$/NKX6.1$^-$ (red gate) cells at indicated time points. D: qPCR analysis of NGN3 and NKX2.2 transcripts at day 8 of differentiation employing RCN (Retinoic acid (R), Cyclopamine (C), and Noggin (N)) or R with two different concentrations of Vitamin C (Vit. C) treatment for 3 days or without treatment. Data are shown as the average±standard error, relative to RCN and normalized to GAPDH. (n=three independent experiments, technical duplicates).
Figure 7:
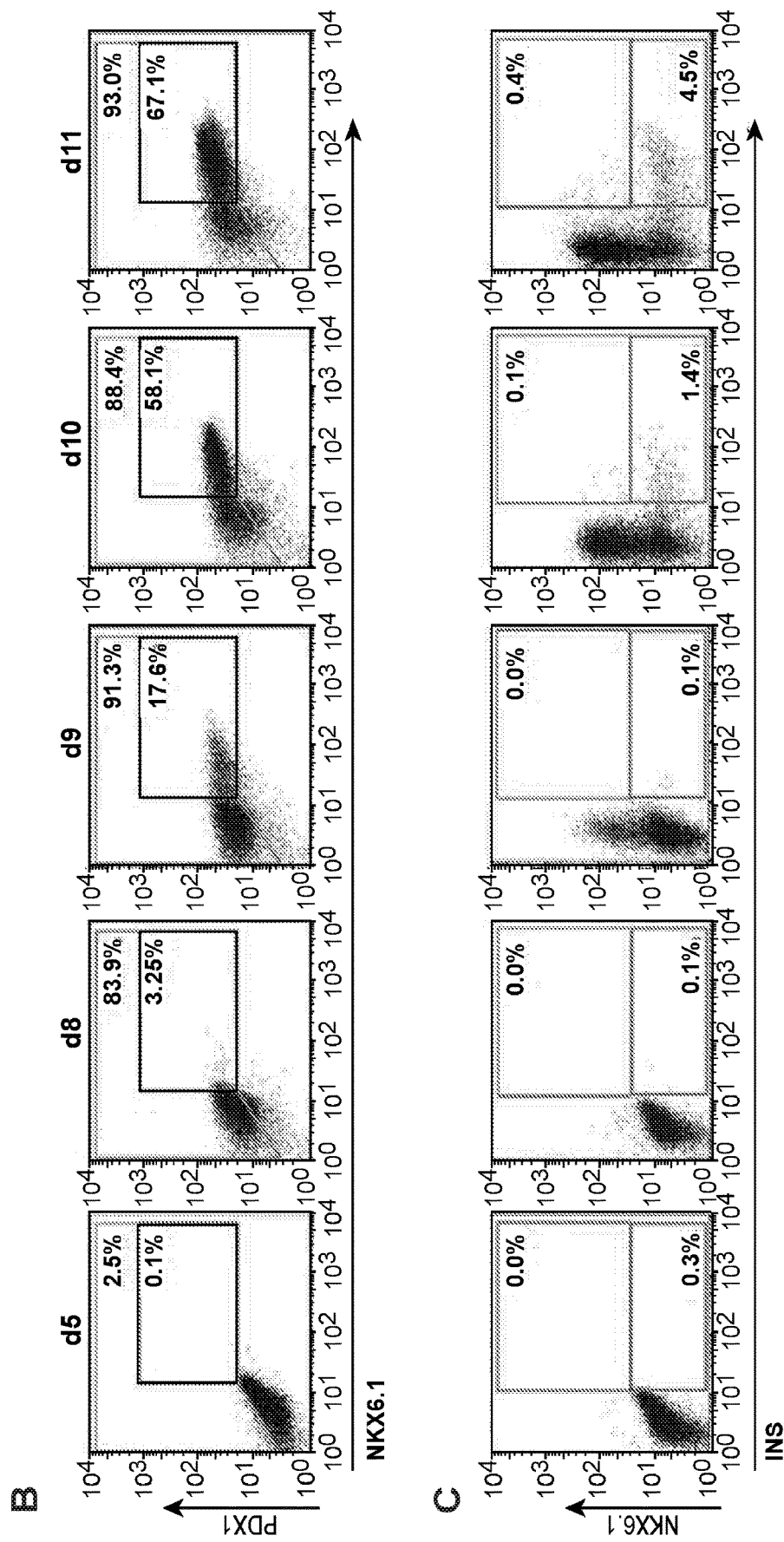
Figure 7:
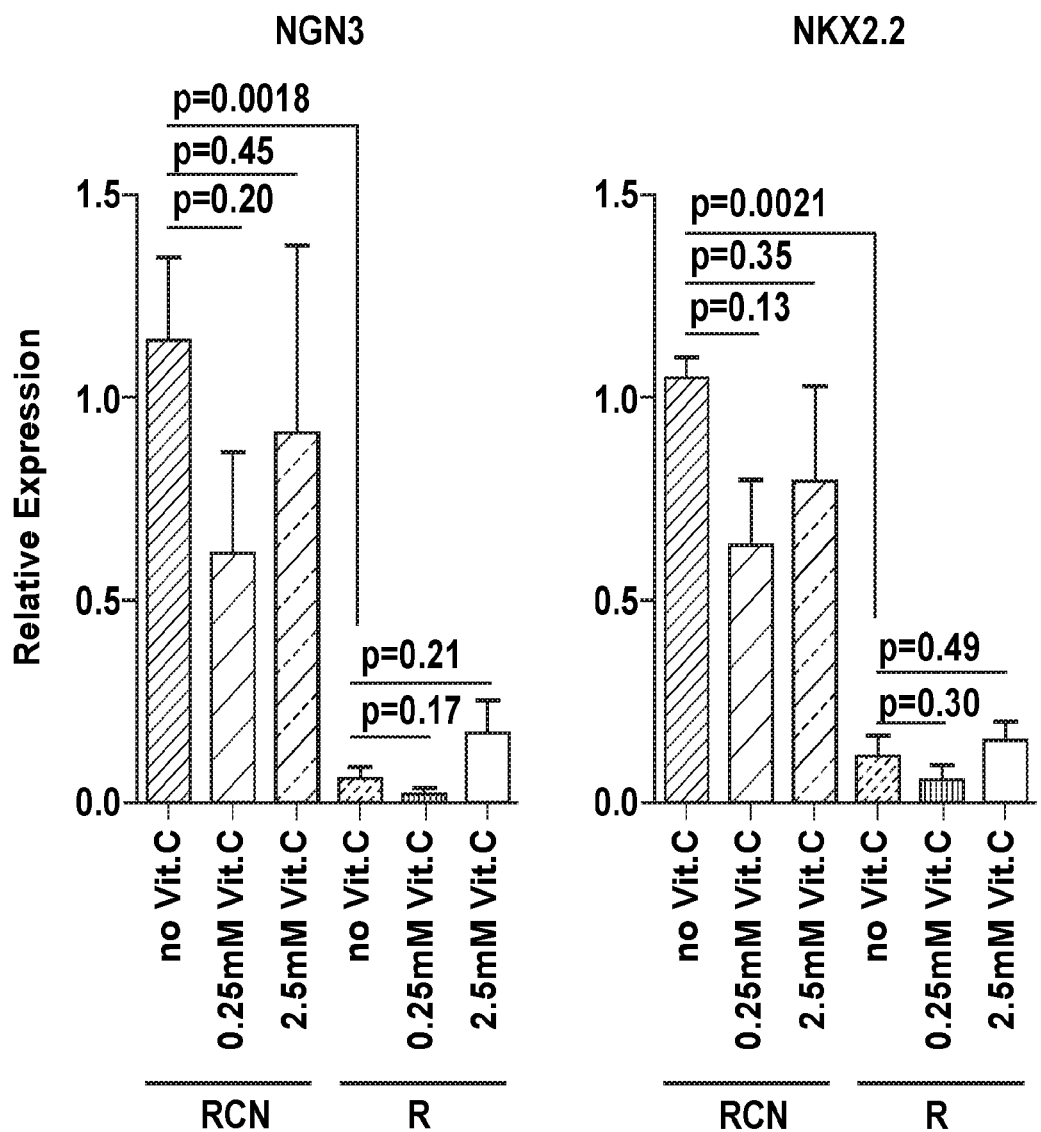

To characterize the type of progenitors present in differentiating cultures at the point of endocrine induction, we performed a detailed time course analysis for the expression of pancreatic markers PDX1, NKX6.1, NEUROG3, GCG and INS (FIG. 7). High expression of the progenitor marker PDX1 was efficiently induced and maintained starting one day after the combined addition of Retinoic Acid (R), the SHH inhibitor Cyclopamine (C), and the BMP inhibitor Noggin (N) to the culture media (referred to as RCN, Day 6, FIGS. 7A and B). Subsequent treatment with epidermal growth factor (EGF), KGF and N (EKN) resulted in the robust generation of $PDX1^+/NKX6.1^+$ double positive cells reaching 67% of the total population at day 11 (FIGS. 7A and B). Immunofluorescence analysis revealed that the RCN cocktail of factors widely used to generate pancreatic endoderm also induces precocious expression of NEUROG3 in $PDX1^+$ pancreatic progenitors. Indeed, the expression of NEUROG3 can be detected as early as day 6, when NKX6.1 protein is absent from all cells (FIGS. 7A and B). Consequentially, insulin-expressing cells that are first detected 4 days after NEUROG3 induction (starting at day 10), do not co-express NKX6.1 and are mostly polyhormonal (FIGS. 1F and G, and FIG. 7C). In contrast, INS/NKX6.1 double positive beta-like cells can be readily detected only at later time points (day 19, FIG. 1G), indicating that these cells differentiate from PDX1/NKX6.1 double positive progenitor cells. We thus expected that robust generation of $PDX1^+/NKX6.1^+$ progenitor cells prior to induction of NEUROG3 would allow efficient generation of beta-like cells in vitro. To determine which of the factors used between days 6-8 in the original protocol (R, C, and N) were responsible for the induction of PDX1, NKX6.1 and NEUROG3, we incubated spheres with each of the factors alone or in different combinations over days 6-8 (FIG. 2A). Basal media with B27 but lacking any additional factors served as the control condition. At the end of day 8, each of these six conditions was further subdivided into three different treatment groups: media composition remained the same as during days 6-8 (group 1), or were changed either to EK (group 2), or to EKN (group 3), resulting in 18 individual experimental conditions (FIG. 2A). Spheres cultured under each condition were analyzed at day 9.5 by flow cytometry to quantify the expression of PDX1 and NKX6.1, and by conventional immunofluorescence analysis for NKX6.1 and NEUROG3 expression. As shown in FIG. 2B, spheres within group 1 that had been exposed to retinoic acid during days 6-8, either alone or in combination with other factors (conditions 4, 5, and 6), exhibited highly efficient generation of PDX1 positive progenitors (>88%), while addition of C or N alone (conditions 2 and 3) did not result in enhanced generation of PDX1$^+$ cells over base media alone. NKX6.1 was induced only weakly in all group 1 conditions, with the exception of RC (condition 5), which produced 45% PDX1/NKX6.1 double positive cells. NKX6.1 expression was also strongly induced when cells were exposed to retinoic acid alone or in combination with other factors followed by treatment with EK (group 2) or EKN (group 3) (FIGS. 2B and C, conditions 10-12 and 16-18). Endocrine differentiation, marked by NEUROG3 expression, was noted only when spheres had been exposed to N, either between days 5-9.5 (FIG. 2C, conditions 3, 6, 9, and 12) or starting at the end of day 8 (FIG. 2C, group 3, conditions 13-18). Very few NEUROG3$^+$ cells were detected in all other conditions (FIG. 2C, conditions 1, 2, 4, 5, 7, 8, 10, and 11). qPCR analysis at day 8 of NEUROG3 and its downstream target NKX2.2 mRNA transcripts revealed significantly lower levels of these endocrine markers with R treatment when compared to the commonly employed RCN condition (FIG. 7D). Notably, addition of Vitamin C, recently shown to reduce endocrine differentiation in hESCs (Rezania et al, 2014), did not significantly lower NGN3 or NKX2.2 transcripts in our suspension culture system during RCN or R treatment (FIG. 7D). Taken together, these results indicate that R followed by EK treatment leads to highly efficient generation of PDX1$^+$/NKX6.1$^+$ progenitors (90%) and that the formation of bona fide NEUROG3 positive endocrine precursors is induced by treatment with N (FIG. 2 A-C, condition 10, green gates). Thus, by defining the temporal activities of individual signaling factors alone and in combination, we can induce transcription factor expression patterns characteristic of different human embryonic pancreatic progenitor cells types (PDX1$^+$ and PDX1$^+$/NKX6.1$^+$ progenitors) without precocious induction of endocrine differentiation.

Example 4

Recapitulating Human Pancreas Organogenesis to Generate Endocrine Progenitors

Figure 3:
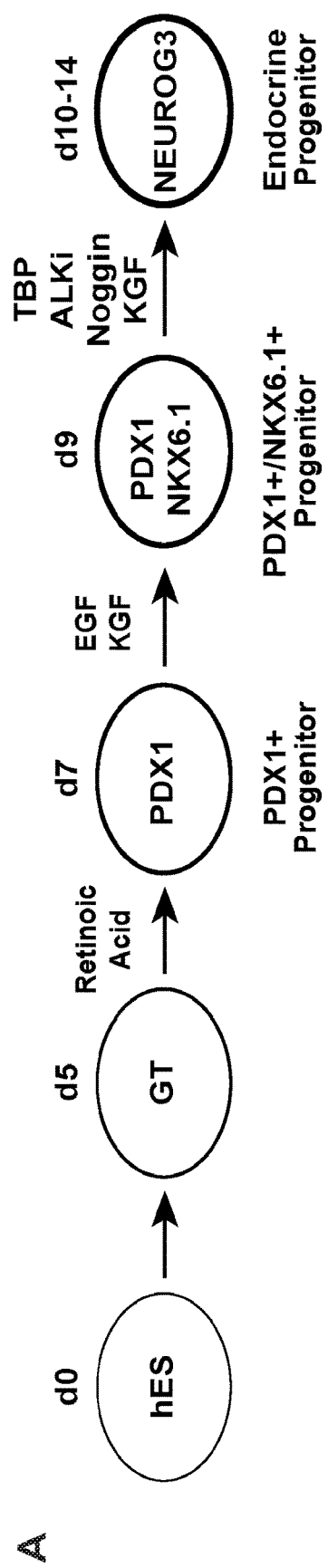
FIG. 3. Recapitulating human pancreas organogenesis to generate endocrine progenitors. A: Schematic outlining a simplified differentiation strategy for the controlled, step-wise generation of pancreatic progenitor cell types. B: Time-course flow cytometric analysis illustrates the efficient generation of PDX1$^+$ progenitor (orange gate) and PDX1$^+$/NKX6.1$^+$ progenitor (blue gate) populations. Data from one of three independent experiments with similar results are shown. C: Immunofluorescence analysis of sections from differentiated clusters at indicated time points stained for human NKX2.2 (green) and NEUROG3 (red). Insets show NEUOG3/NKX2.2 double positive cells. Data from one of three independent experiments with similar results is shown.
Figure 3:
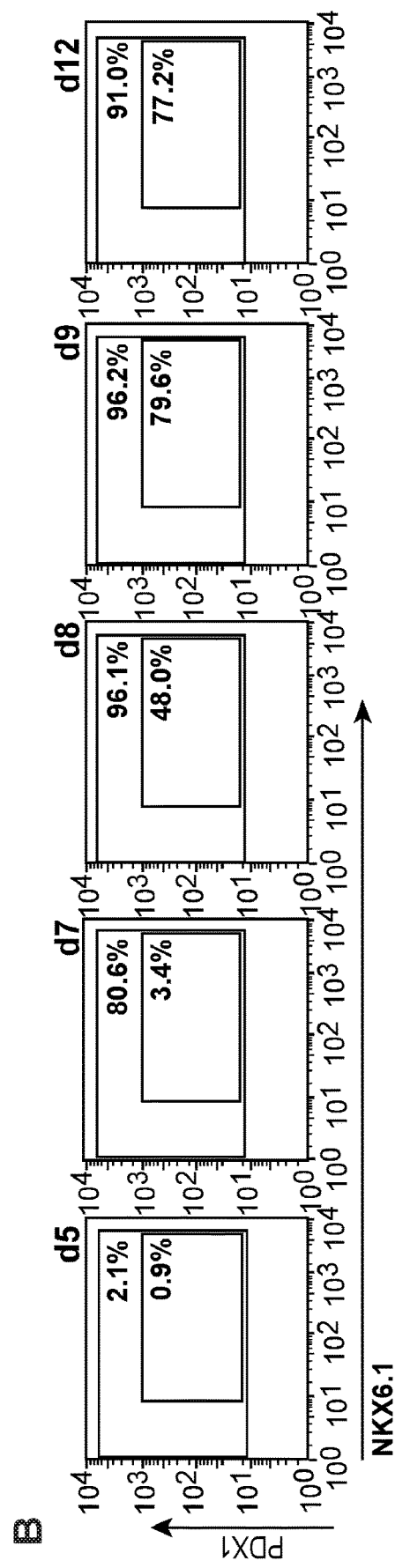
Figure 3:
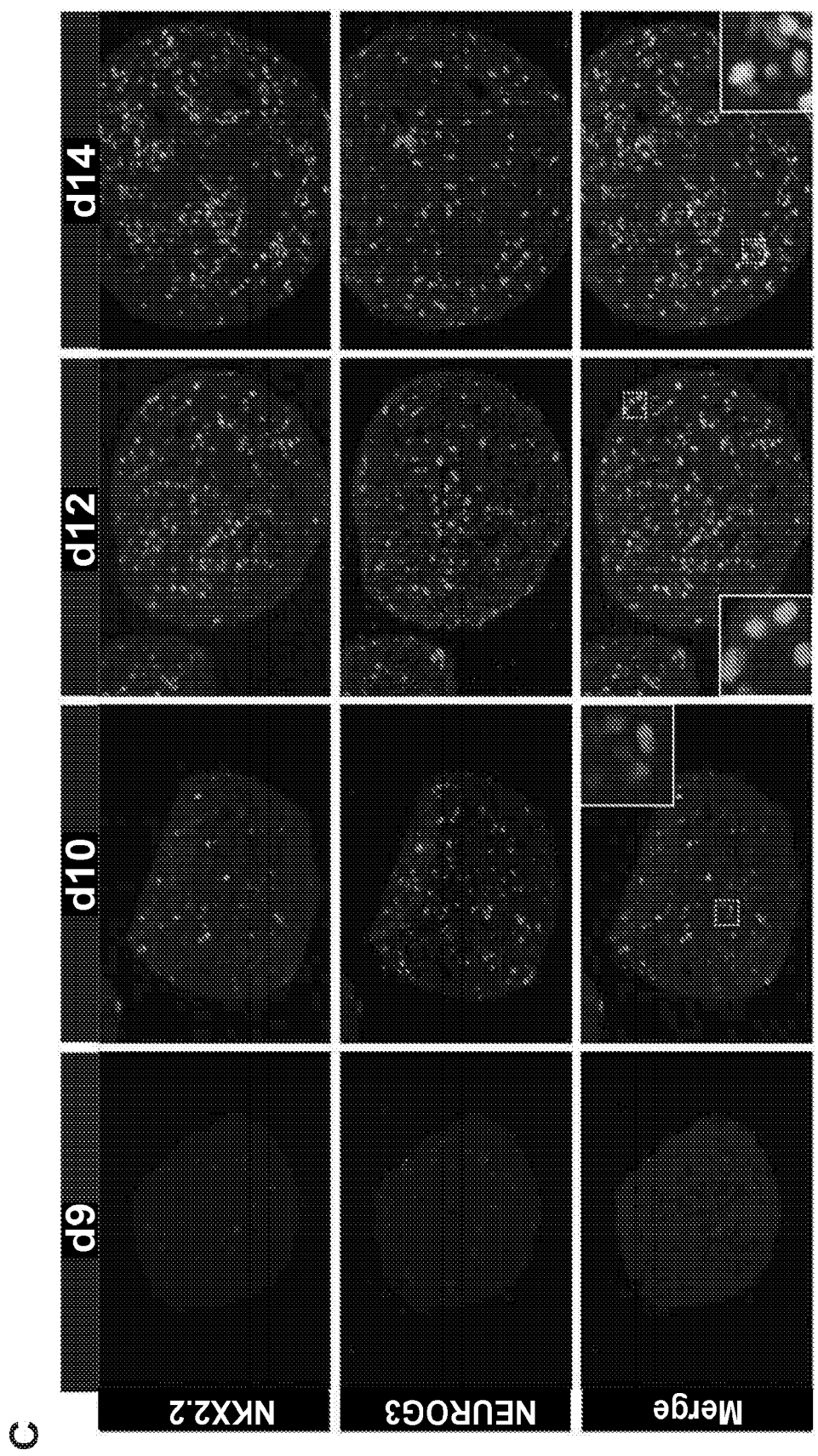

This improved and simplified differentiation protocol provides the basis for subsequent efficient formation of insulin-producing cells in suspension (FIG. 3A). Endocrine differentiation in PDX1/NKX6.1 double positive cells was induced by exposure to a cocktail of factors consisting of TBP (T), ALK inhibitor (A), N, and K, (TANK) which have previously been shown to activate NEUROG3 expression while maintaining high expression of PDX1 and NKX6.1 (Rezania et al, 2012; Nostro et al, 2011) (FIGS. 3A and B). While NEUROG3 protein was undetectable before TANK treatment (FIG. 3C, day 9), cells exhibiting nuclear accumulation of NEUROG3 protein appeared as early as one day following TANK treatment (FIG. 3C, day 10). Thus, expression of the pro-endocrine factor NEUROG3 is rapidly induced through TANK treatment once PDX1$^+$/NKX6.1$^+$ progenitors are specified (FIG. 3B, day 9). In contrast to the near-uniform generation of PDX1$^+$ and PDX1$^+$/NKX6.1$^+$ progenitor populations following appropriate stimulation, endocrine differentiation appears to be confined to a smaller population of cells. This observation can be explained by the very short half-life of the NEUROG3 protein (Roark et al, 2012), which allows only transient detection of this marker in cells undergoing endocrine differentiation. NEUROG3$^+$ cells, however, continued to be present when clusters were exposed to the endocrine differentiation cocktail for 5 days (FIG. 3C, day 14), indicating that endocrine cells were being generated throughout this period. To further characterize the progenitors present in our cultures at the initiation of endocrine differentiation, we analyzed the expression of NKX2.2, a downstream target of NEUROG3. NKX2.2 has recently been reported to have distinct expression patterns during pancreatic organogenesis in mouse and human (Jennings et al, 2013). While NKX2.2 is readily detectable in mouse pancreatic progenitor cells before NEUROG3 expression, NKX2.2 protein is only observed after endocrine commitment during human pancreas development. Similarly, we detected NKX2.2 protein expression only after endocrine differentiation is initiated at day 10, but not before in either PDX1$^+$ or PDX1$^+$/NKX6.1$^+$ progenitors (FIG. 3C). Of note, some NKX2.2$^+$ cells at day 10 co-express NEUROG3, and increasing numbers of NKX2.2$^+$/NEUROG3$^-$ cells are found at later time points (FIG. 3C). These data indicate that NKX2.2 could serve as a lineage tracer for human cells that have undergone endocrine differentiation induced by transient NEUROG3 expression. In summary, we have established a novel differentiation strategy that faithfully recapitulates human pancreas organogenesis and allows for the precise control over the generation of PDX1$^+$ and PDX1$^+$/NKX6.1$^+$ progenitors.

Example 5

Efficient Generation of PDX1$^+$/NKX6.1$^+$ Pancreatic Progenitor Cells Prior to Endocrine Induction Results in Glucose Responsive Beta-Like Cells.

Figure 4:
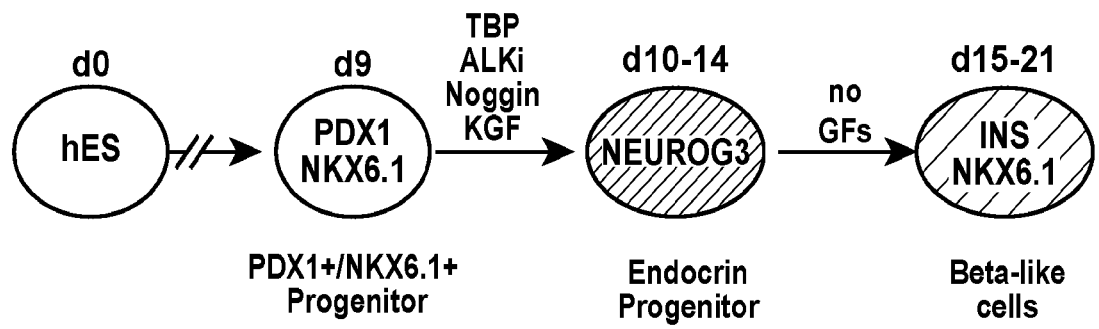
FIG. 4. Efficient generation of PDX1$^+$/NKX6.1$^+$ pancreatic progenitor cells prior to endocrine induction results in beta-like cells. A: Schematic outlining a simplified differentiation strategy for the controlled, step-wise generation of pancreatic progenitor and subsequent endocrine cell types. GFs=growth factors. B: Micrographs of differentiated clusters at day 19 under light microscopy (left picture) or fluorescent microscopy showing prominent GFP expression (right picture; GFP expression shown in white). C: Quantification of the percentage of human C-peptide positive cells at day 19-21. Values are average±SD. n=7 independent experiments. D: Immunofluorescence stainings of differentiated clusters at day 20 for insulin (INS), PDX1, NKX6.1, NKX2.2 and glucagon (GCG). One of four experiments with similar outcome is shown. E: Representative flow cytometry plots depicting co-expression of pancreatic markers PDX1, NKX6.1, NKX2.2, ISL1, NEUROD1, PAX6, ChromograninA (CHGA), and GCG with human C-peptide at indicated time points. Black gates mark percentage of total cells positive for indicated marker on 'Y' axis. Green gates mark percentage of double positive beta-like cells. The red gate marks percentage of INS$^+$/GCG$^+$ bihormonal cells. F: Flow cytometric quantification of C-peptide positive beta-like cells co-expressing markers in 'D'. A high percentage of beta-like cells co-express all genes usually found in beta cells, but not the hormone GCG. Values are average±SD. n=4 for PDX1, n=19 for NKX6.1, n=4 for NKX2.2, n=9 for ISL1, n=9 for NEUROD1, n=5 for PAX6, n=6 for CHGA, and n=5 for GCG. Analysis was performed at days 15-21 of differentiation.
Figure 4:
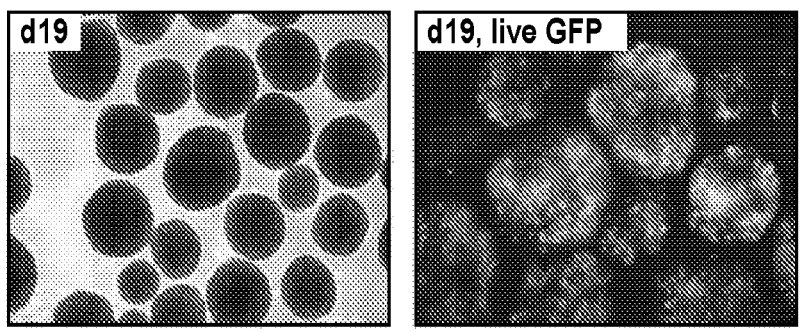
Figure 4:
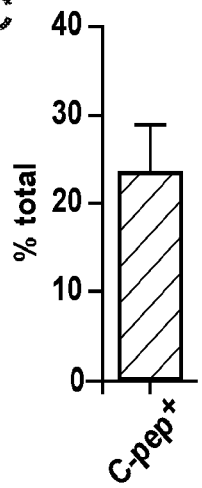
Figure 4:
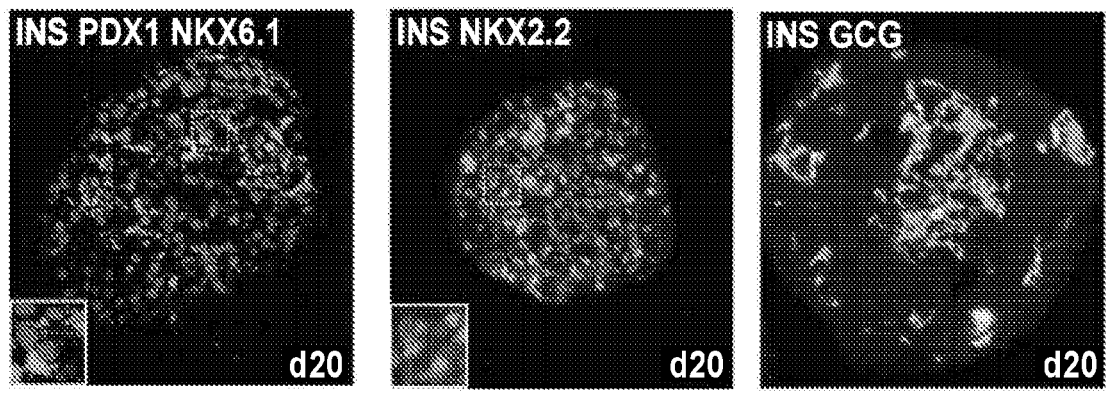
Figure 4:
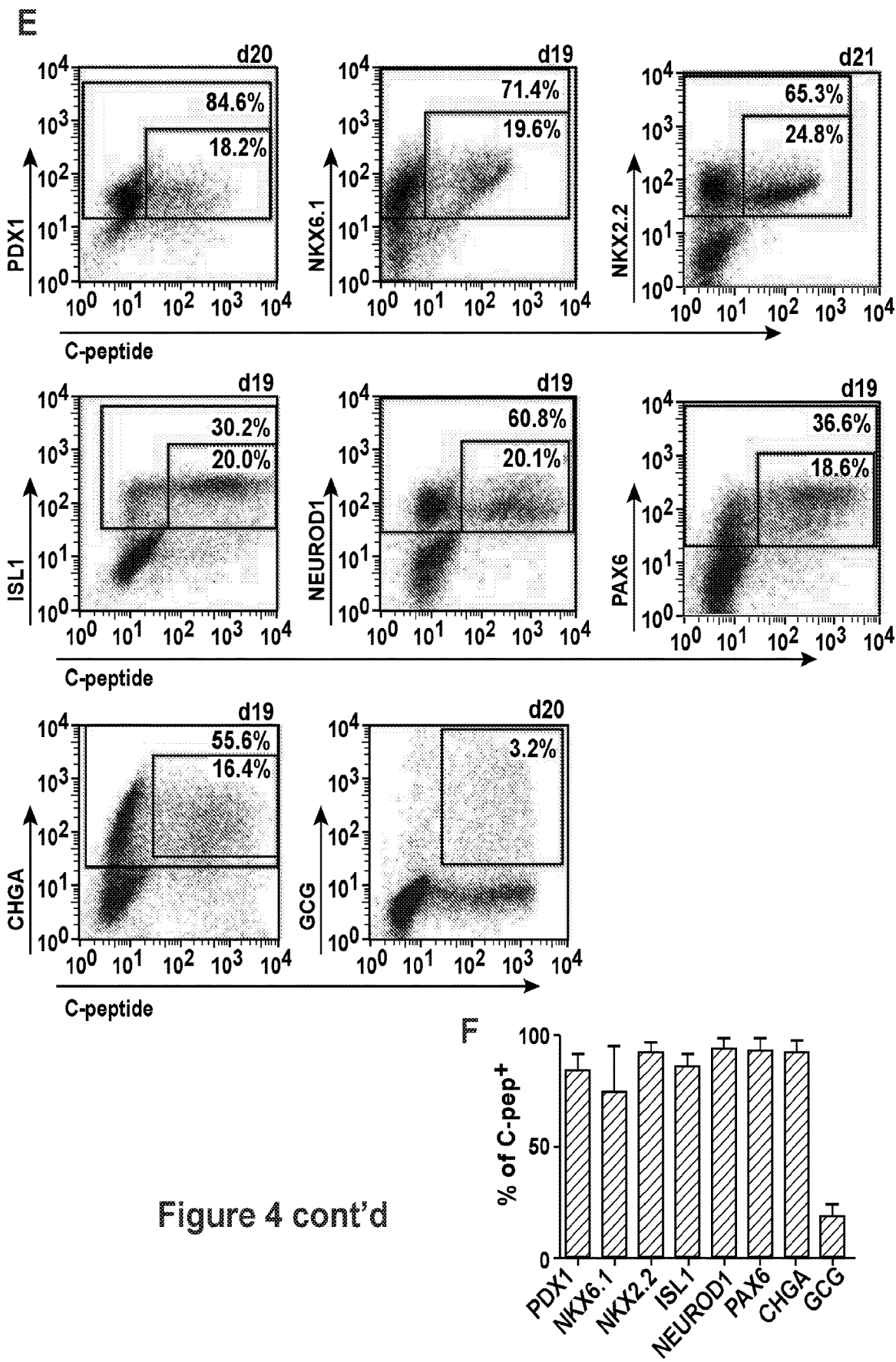
Figure 8:
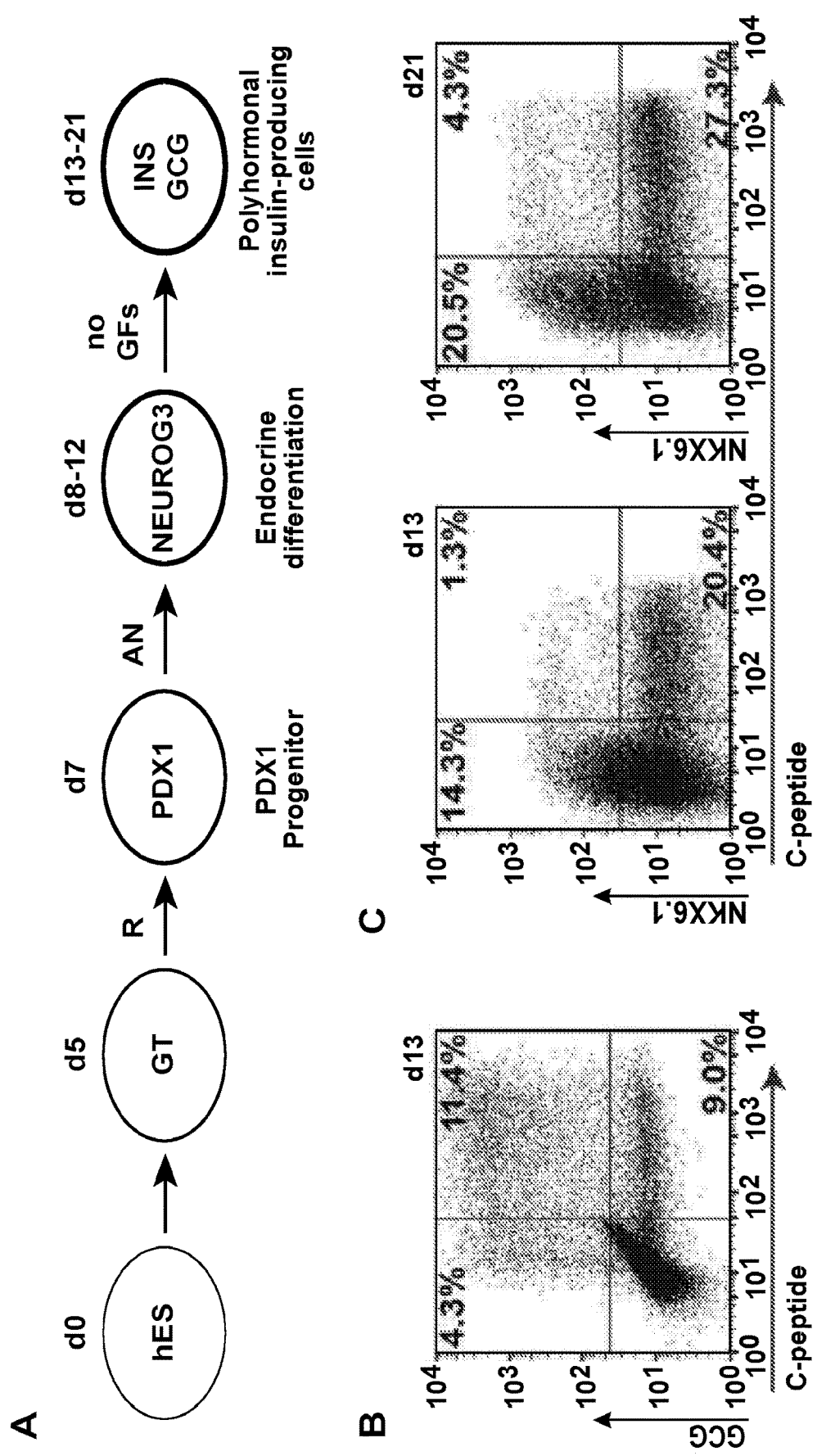
FIG. 8. Induction of NEUROG3 expression in PDX1$^+$ pancreatic progenitors results in insulin-producing cells that lack NKX6.1 expression. A: Schematic outlining the differentiation strategy employed. R=Retinoic Acid, N=Noggin, and A=ALK inhibitor. B and C: Flow cytometric analysis of human c-peptide (C-PEP), glucagon (GCG), and NKX6.1 expression at the indicated differentiation time points. Data representative of 3 to 4 independent experiments with similar results are shown. B: Endocrine differentiation of PDX1$^+$ pancreatic progenitors results in the predominant generation of polyhormonal insulin- and glucagon-producing cells at day 13. C: Insulin-producing cells lack expression of the critical beta cell transcription factor NKX6.1 at day 13 and 21. A small population of NKX6.1$^+$/INS$^-$ progenitor cells is generated by NEUROG3-inducing treatment with AN.
Figure 9:
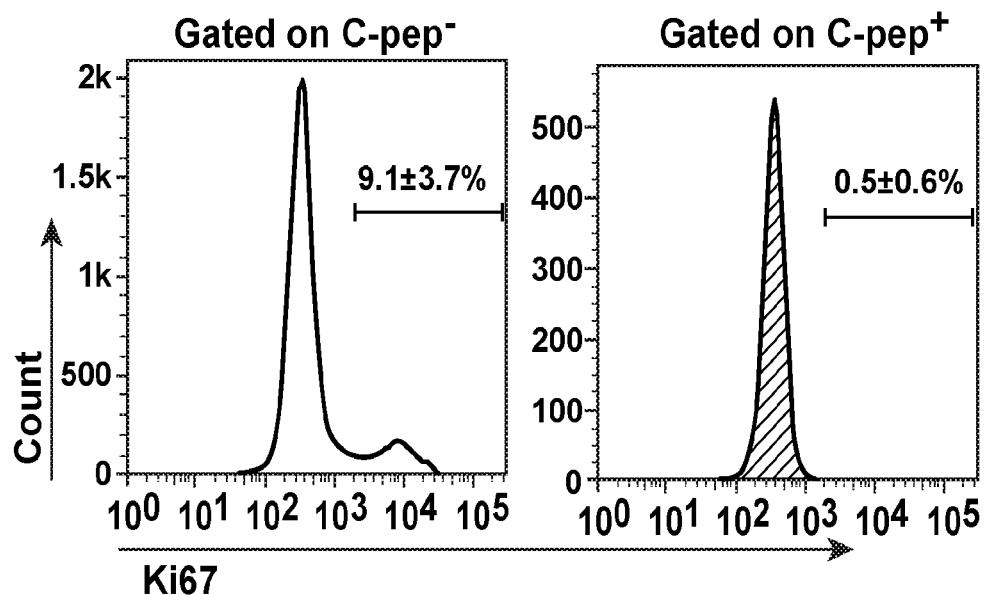
FIG. 9. hESC derived beta-like cells are post-mitotic. A: Proliferation of C-peptide$^+$ beta-like cells and C-peptide negative cell populations at days 18-20 was determined by co-staining with the proliferation marker Ki67. B: Immunofluorescence staining of differentiated clusters at day 20 for the proliferation marker Ki67 and human insulin (INS). Representative data from one of three experiments with similar results are shown.
Figure 9:
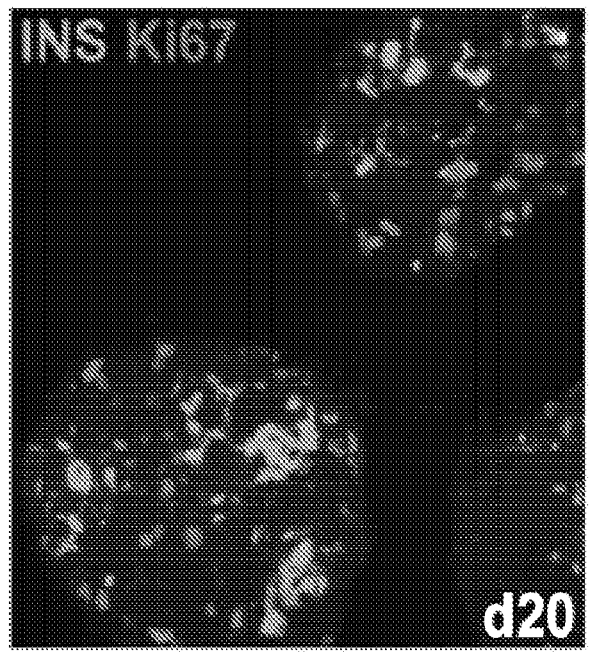

To test the expectation that precocious activation of NEUROG3 expression results in immature polyhormonal cells and not INS/NKX6.1 double positive beta-like cells, we initiated endocrine differentiation at day 7 in PDX1$^+$ pancreatic progenitors by exposing the cells to NEUROG3 inducers ALKi and Noggin (FIG. 8A). While some single-hormone-positive cells were present at day 13, many endocrine cells were double-positive for C-peptide and glucagon (FIG. 8B). In further support of our expectation, virtually all C-peptide-positive cells lacked expression of NKX6.1 (FIG. 8C). To test whether correctly specified PDX1$^+$/NKX6.1$^+$ progenitor cells undergo differentiation towards INS/NKX6.1 double positive beta-like cells, we transferred spheres differentiated using our new method into a basal media without additional growth factors and monitored the establishment of beta-like cells (FIG. 4A). The percentage of GFP$^+$ cells increased from day 13 to day 19, reaching an average of 23±6% human C-peptide-positive cells at days 19-21, likely reflecting continuous generation of insulin-producing cells for about 4 days after removal of NEUROG3-inducing factors (FIG. 4B, C). Immunofluorescence analysis of insulin-producing cells revealed co-expression and nuclear localization of TFs critical for beta cell function (PDX1, NKX6.1 and NKX2.2), but very few polyhormonal cells (FIG. 4D). Flow cytometry analysis of differentiated clusters showed a high percentage of total cells (black gates) and C-peptide positive beta-like cells (green gates) co-staining for PDX1, NKX6.1, NXK2.2, ISL1, PAX6, NeuroD1, and ChromograninA (CHGA) (FIG. 4E). These markers are normally found in both pancreatic progenitors and mature beta cells. Quantification of C-peptide[+] beta-like cells co-staining for PDX1, NKX6.1, NKX2.2, ISL1, NEUROD1, PAX6 and Chromogranin A showed 84±7%, 75±20%, 92±5%, 86±5%, 95±4%, 93±5%, and 93±4% double positive cells, respectively (FIG. 4F). Notably, only 3.2% of all differentiated cells co-expressed C-peptide and the hormone glucagon (FIG. 4E, red gate). An important hallmark of mature human beta cells is their restricted proliferative capacity. While 9.1±3.7% of C-peptide-negative cells were actively proliferating, only 0.5±0.6% of C-peptide-positive beta-like cells co-stain for the proliferation marker Ki67, indicating their terminal differentiation state (FIGS. 9A and B). Thus, our optimized differentiation strategy results in the predominant generation of post-mitotic, insulin-producing beta-like cells that co-express critical beta cell markers.

Figure 10:
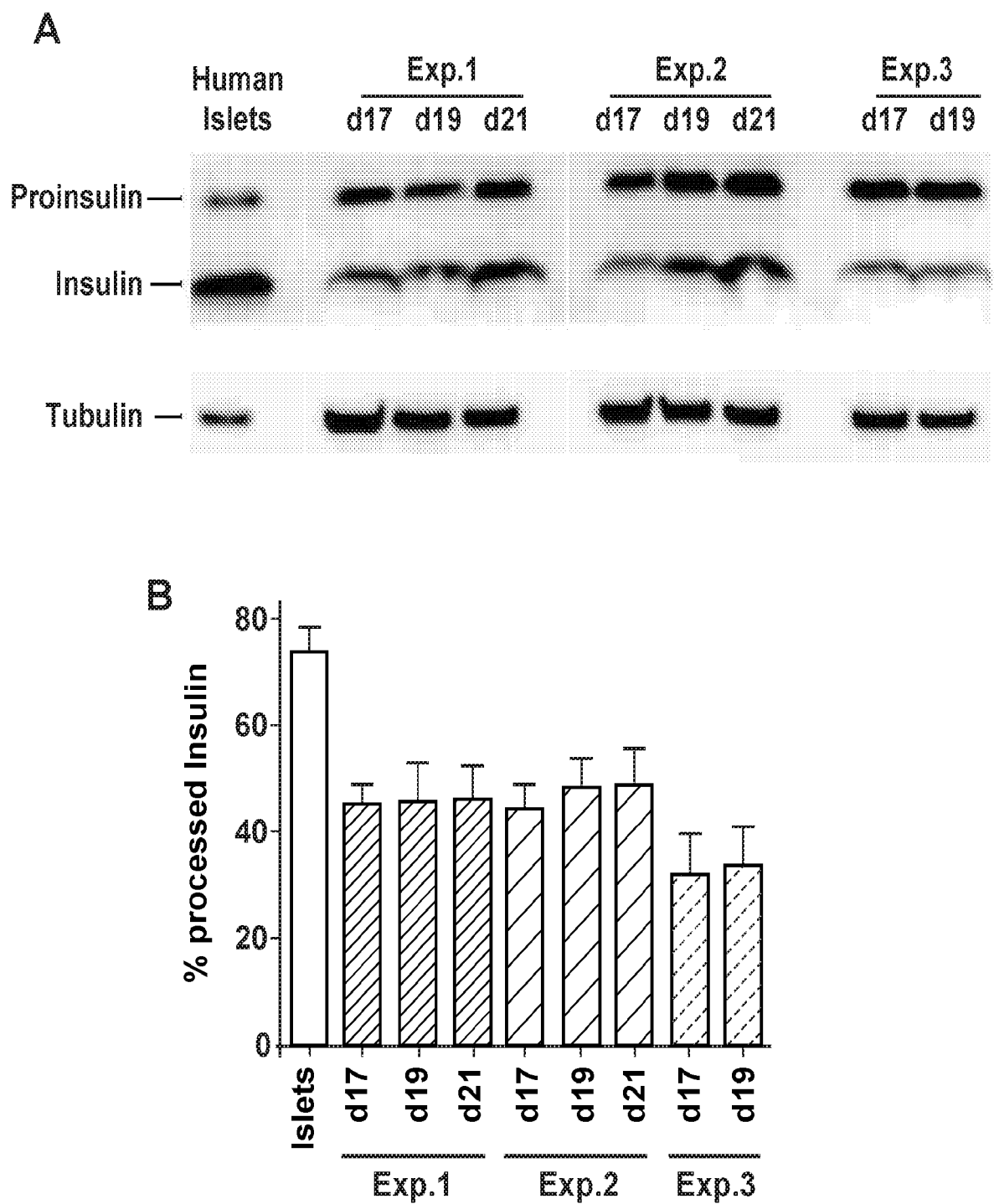
FIG. 10. Efficient processing of insulin in hESC derived beta-like cells. A: Western blot analysis of proinsulin processing to insulin in beta-like cells at indicated time points. A human islet preparation is shown for comparison. Proceeding from left to right, Western blot panels of the following are provided: i) two human islet preparations, ii) hES9.3 cells sampled at days 17, 19 and 21, iii) hES9.6 cells sampled at days 17, 19 and 21, and iv) hES9.10 cells sampled at days 17 and 19, are shown The Western blot was cropped to conserve space, enabling tubulin levels to be shown (as a higher molecular weight protein, tubulin ran above proinsulin and insulin in the gel subjected to Western blot). B: Quantification of proinsulin processing in FIG. 5E and panel A. n=3 for each time point of beta-like cells and n=4 for human islets.

To further characterize gene expression in beta-like cells at days 19-20, we took advantage of the GFP live marker to compare sorted GFP[+] beta-like cells and GFP– populations to purified human islets. hESC-derived beta-like cells showed high levels of insulin gene transcripts, comparable to cadaveric islet preparations, while GFP-negative populations exhibit only insignificant levels of the hormone (FIG. 5A). We also detected transcript levels for two other hormones (GCG and SST) in GFP[+] cells, likely due to contamination by the small number of polyhormonal cells also expressing the GFP reporter (FIGS. 5A and 4D and E). Consistent with the immunofluorescence analysis (FIG. 4D), transcripts for the TFs PDX1, NKX6.1 and NKX2.2 normally found in both progenitor and mature beta cells were expressed at comparable levels in GFP-negative, GFP-positive, and islet cells (FIG. 5B). Transcripts for the mature human beta cell transcription factors MAFA and MAFB were robustly expressed in human islets and enriched in beta-like cells compared to GFP– populations. MAFB transcript levels in beta-like cells were similar to human islets; MAFA expression levels were slightly lower (FIG. 5B). Other genes important for human beta cell functionality, including the KATP channel components Potassium Inwardly-Rectifying Channel, Subfamily J, Member 11 (KIR6.2 also known as KCJN11) and ATP-Binding Cassette, Sub-Family C, Member 8 (SUR1 also known as ABCC8), the glucose metabolism enzyme Glucokinase (GCK, also known as HK4), and the Prohormone Convertase 1/3 (PC1/3) necessary for insulin biosynthesis, were enriched in GFP–positive beta-like cells at levels similar to or exceeding those found in human islets (FIG. 5C). In contrast, mRNA levels for the progenitor marker SOX9 were reduced in beta-like cells compared to GFP– progenitors (FIG. 5D). The somewhat higher SOX9 expression in human islets is likely the result of contamination with Sox9-positive duct cells. Thus, our gene expression analysis indicated that hESC-derived beta-like cells possess the molecular machinery necessary for beta cell function, including insulin biosynthesis and glucose metabolism. Further investigations revealed that day 19 beta-like cells contain 2.5±1.2 ug, 0.32±0.12 ug, and 310±143 ng insulin, human c-peptide, and proinsulin per μg DNA, respectively (FIG. 5E). These values are comparable to about 2.8 ug insulin, about 0.55 ug c-peptide, and about 150 ng proinsulin per μg DNA for human islets, as recently published (Rezania et al, 2014). Western blot analysis for proinsulin and mature insulin further confirmed efficient insulin protein processing in hESC-derived beta-like cells, reaching 59±2% of the extent of processing observed in purified human islets (FIGS. 10A and B). Ultrastructural analysis of differentiated cell clusters by transmission electron microscopy revealed that many cells contained secretory vesicles exhibiting electron dense cores or rod-like structures, akin to what is observed in human beta cells (FIG. 5F). To further investigate the functional properties of in vitro differentiated beta-like cells, we performed glucose stimulated insulin secretion assays, in which we measured the release of human C-peptide, a by-product of endogenous insulin biosynthesis secreted in an equimolar ratio to insulin. hESC-derived beta-like cells analyzed at days 19-21 responded to an increase in glucose concentration from 2.8 mM to 16.7 mM by secreting 1.8±0.9-fold more C-peptide, a response similar to the 1.9±0.6-fold increase detected with human islets (FIG. 5G). Thus, beta-like cells generated by our optimized differentiation strategy express critical beta cell genes, synthesize high levels of mature insulin, exhibit ultrastructural features of bona fide beta cells and secrete endogenous insulin in response to changes in physiological concentrations of glucose.

Example 6 hESC-Derived Beta-Like Cells Remain Glucose Responsive after Short Term Transplantation.

To determine whether hESC-derived beta-like cells can maintain their glucose responsiveness in vivo, we transplanted approximately 5 million cells under the kidney capsule of immunodeficient mice (days 19-21 spheres consisting of progenitors and beta-like cells). Mice transplanted with 4000 human islets served as controls. Seven to 10 days post-surgery, human C-peptide levels were measured in overnight-fasted mice, before and after the administration of a glucose bolus. As expected, mice that received human islet grafts exhibited low levels of insulin secretion upon fasting, followed by a marked increase in circulating insulin after glucose challenge (average of 221±116 pM, FIG. 6A). Similar to mice carrying human islets, fasted mice transplanted with hESC-derived beta-like cells had low levels of circulating C-peptide. Upon glucose administration, C-peptide concentrations in sera of these mice also increased, albeit at lower levels than in mice transplanted with human islets (average of 40±28 pM, FIG. 6A). This lower number might be explained in part by the different numbers of cells transplanted in the human islet and beta-like cell groups. Indeed, each human islet contains on average 1000 cells, of which 50% are beta cells (Cabrera et al, 2006). Thus, 4000 human islets contain approximately $2.0 \times 10^6$ bonafide beta cells. Because hESC differentiated spheres contain on average 23% beta-like cells, only about $1.15 \times 10^6$ beta-like cells were transplanted per mouse. Normalization based on beta cell number indicates that hESC derived beta-like cells secreted 70±48 pM human c-peptide per $2.0 \times 10^6$ cells, representing approximately ⅓ of the insulin secreted from each human cadaveric beta cell (FIG. 6A). Hematoxylin and Eosin staining, together with immunofluorescence analysis of the hESC grafts at 2 weeks post-transplantation demonstrated prominent islet-like structures positive for human C-peptide (FIGS. 6B and C). Beta-like cells also maintained co-expression of the key beta cell TFs PDX1, NKX6.1 and NKX2.2, and only a few cells co-expressed other hormones, such as glucagon and somatostatin (FIG. 6C). To further investigate the functional properties of hES derived beta-like cells in vivo, we transplanted clusters under the kidney capsule of mice rendered diabetic through treatment with the beta cell toxin streptozotocin. Mice that received grafts exhibit significantly reduced blood glucose (BG) levels at all time points analyzed when compared to control animals (FIG. 6D). While BG levels were significantly reduced in graft-bearing mice, they continued to exhibit hyperglycemic BG values over time. This is likely due to the limited number of beta-like cells that can be transplanted under the kidney capsule in one mouse. It has previously been shown that 4,000 human islets are required to establish long-term euglycemia in diabetic mice. Transplantation of a smaller number of human islets (1,500 islets) reduces blood glucose levels only for 7 days post-transplantation, after which hyperglycemia returned (Fiaschi-Taesch et al, 2010). Our surgical procedure permits the transplantation of about $1.15 \times 10^6$ beta-like cells, substantially less than the approximately $2.0 \times 10^6$ beta cells present in the 4,000 human islets previously found to be required for the long-term reversal of diabetes. Hence, the observed reduction in BG levels, but lack of complete diabetes reversal in mice bearing hES-derived transplants, is not unexpected given this technical constraint. Taken together, the in vivo data demonstrate that hESC derived beta-like cells maintain their differentiated phenotype and remain glucose responsive after a short engraftment period in vivo and highlights their potential therapeutic value.

REFERENCES

Barton F B, Rickels M R, Alejandro R, Hering B J, Wease S, Naziruddin B, Oberholzer J, Odorico J S, Garfinkel M R, Levy M, Pattou F, Berney T, Secchi A, Messinger S, Senior P A, Maffi P, Posselt A, Stock P G, Kaufman D B, Luo X, et al (2012) Improvement in outcomes of clinical islet transplantation: 1999-2010. Diabetes Care 35: 1436-1445.

Bouwens L, Houbracken I & Mfopou J K (2013) The use of stem cells for pancreatic regeneration in diabetes mellitus. Nat Rev Endocrinol 9: 598-606.

Cabrera O, Berman D M, Kenyon N S, Ricordi C, Berggren P-O & Caicedo A (2006) The unique cytoarchitecture of human pancreatic islets has implications for islet cell function. Proc. Natl. Acad. Sci. U.S.A. 103: 2334-2339.

Chen S, Borowiak M, Fox J L, Maehr R, Osafune K, Davidow L, Lam K, Peng L F, Schreiber S L, Rubin L L & Melton D (2009) A small molecule that directs differentiation of human ESCs into the pancreatic lineage. Nat. Chem. Biol. 5:258-265.

D'Amour K A, Agulnick A D, Eliazer S, Kelly O G, Kroon E & Baetge E E (2005) Efficient differentiation of human embryonic stem cells to definitive endoderm. Nat. Biotechnol. 23: 1534-1541.

D'Amour K A, Bang A G, Eliazer S, Kelly O G, Agulnick A D, Smart N G, Moorman M A, Kroon E, Carpenter M K & Baetge E E (2006) Production of pancreatic hormone-expressing endocrine cells from human embryonic stem cells. Nat. Biotechnol. 24: 1392-1401.

De Krijger R R, Aanstoot H J, Kranenburg G, Reinhard M, Visser W J & Bruining G J (1992) The midgestational human fetal pancreas contains cells coexpressing islet hormones. Developmental Biology 153: 368-375.

Efrat S & Russ H A (2012) Making ß cells from adult tissues. Trends in Endocrinology & Metabolism 23: 278-285.

Fiaschi-Taesch N M, Salim F, Kleinberger J, Troxell R, Cozar-Castellano I, Selk K, Cherok E, Takane K K, Scott D K & Stewart A F (2010) Induction of Human-Cell Proliferation and Engraftment Using a Single G1/S Regulatory Molecule, cdk6. Diabetes 59: 1926-1936.

Gu G, Dubauskaite J & Melton D A (2002) Direct evidence for the pancreatic lineage: NGN3+ cells are islet progenitors and are distinct from duct progenitors. Development 129: 2447-2457.

Guo S, Dai C, Guo M, Taylor B, Harmon J S, Sander M, Robertson R P, Powers A C & Stein R (2013a) Inactivation of specific ß cell transcription factors in type 2 diabetes. J. Clin. Invest. 123: 3305-3316.

Guo T, Landsman L, Li N & Hebrok M (2013b) Factors Expressed by Murine Embryonic Pancreatic Mesenchyme Enhance Generation of Insulin-Producing Cells From hESCs. Diabetes.

Haataja L, Snapp E, Wright J, Liu M, Hardy A B, Wheeler M B, Markwardt M L, Rizzo M & Arvan P (2013) Proinsulin intermolecular interactions during secretory trafficking in pancreatic ß cells. Journal of Biological Chemistry 288:1896-1906.

Hebrok M (2003) Hedgehog signaling in pancreas development. Mech. Dev. 120:45-57.

Hebrok M (2012) Generating ß cells from stem cells—the story so far. Cold Spring Harb Perspect Med 2: a007674.

Herrera P L, Népote V & Delacour A (2002) Pancreatic cell lineage analyses in mice. Endocrine 19: 267-278.

Hua H, Shang L, Martinez H, Freeby M, Gallagher M P, Ludwig T, Deng L, Greenberg E, Leduc C, Chung W K, Goland R, Leibel R L & Egli D (2013) iPSC-derived ß cells model diabetes due to glucokinase deficiency. J. Clin. Invest.

Jennings R E, Berry A A, Kirkwood-Wilson R, Roberts N A, Hearn T, Salisbury R J, Blaylock J, Piper Hanley K & Hanley N A (2013) Development of the human pancreas from foregut to endocrine commitment. Diabetes 62: 3514-3522.

Johansson K A, Dursun U, Jordan N, Gu G, Beermann F, Gradwohl G & Grapin-Botton A (2007) Temporal control of neurogenin3 activity in pancreas progenitors reveals competence windows for the generation of different endocrine cell types. Developmental Cell 12: 457-465.

Kelly O G, Chan M Y, Martinson L A, Kadoya K, Ostertag T M, Ross K G, Richardson M, Carpenter M K, D'Amour K A, Kroon E, Moorman M, Baetge E E & Bang A G (2011) Cell-surface markers for the isolation of pancreatic cell types derived from human embryonic stem cells. Nat. Biotechnol. 29: 750-756.

Kroon E, Martinson L A, Kadoya K, Bang A G, Kelly O G, Eliazer S, Young H, Richardson M, Smart N G, Cunningham J, Agulnick A D, D'Amour K A, Carpenter M K & Baetge E E (2008) Pancreatic endoderm derived from human embryonic stem cells generates glucose-responsive insulin-secreting cells in vivo. Nat. Biotechnol. 26: 443-452.

Liu H, Yang H, Zhu D, Sui X, Li J, Liang Z, Xu L, Chen Z, Yao A, Zhang L, Zhang X, Yi X, Liu M, Xu S, Zhang W, Lin H, Xie L, Lou J, Zhang Y, Xi J, et al (2014) Systematically labeling developmental stage-specific genes for the study of pancreatic. Cell Res.: 1-20.

Maehr R, Chen S, Snitow M, Ludwig T, Yagasaki L, Goland R, Leibel R L & Melton D A (2009) Generation of pluripotent stem cells from patients with type 1 diabetes. Proc. Natl. Acad. Sci. U.S.A. 106: 15768-15773.

Mfopou J K, Chen B, Mateizel I, Sermon K & Bouwens L (2010) Noggin, retinoids, and fibroblast growth factor regulate hepatic or pancreatic fate of human embryonic stem cells. Gastroenterology 138: 2233-45, 2245.e1-14.

Micallef S J, Li X, Schiesser J V, Hirst C E, Yu Q C, Lim S M, Nostro M C, Elliott D A, Sarangi F, Harrison L C, Keller G, Elefanty A G & Stanley E G (2012) INS(GFP/ w) human embryonic stem cells facilitate isolation of in vitro derived insulin-producing cells. Diabetologia 55: 694-706.

Murtaugh L C & Melton D A (2003) Genes, signals, and lineages in pancreas development. Annu. Rev. Cell Dev. Biol. 19: 71-89.

Nostro M-C & Keller G (2012) Generation of beta cells from human pluripotent stem cells: Potential for regenerative medicine. Seminars in Cell and Developmental Biology 23: 701-710.

Nostro M C, Sarangi F, Ogawa S, Holtzinger A, Corneo B, Li X, Micallef S J, Park I-H, Basford C, Wheeler M B, Daley G Q, Elefanty A G, Stanley E G & Keller G (2011) Stage-specific signaling through TGFß family members and WNT regulates patterning and pancreatic specification of human pluripotent stem cells. Development 138: 861-871.

Pagliuca F W & Melton D A (2013) How to make a functional B-cell. Development 140: 2472-2483.

Pagliuca F W, Millman J R, Giirtler M, Segel M, Van Dervort A, Ryu J H, Peterson Q P, Greiner D & Melton D A (2014) Generation of Functional Human Pancreatic b Cells In Vitro. Cell 159: 428-439.

Pan F C & Wright C (2011) Pancreas organogenesis: from bud to plexus to gland. Dev. Dyn. 240: 530-565.

Posselt A M, Szot G L, Frassetto L A, Masharani U, Tavakol M, Amin R, McElroy J, Ramos M D, Kerlan R K, Fong L, Vincenti F, Bluestone J A & Stock P G (2010) Islet Transplantation in Type 1 Diabetic Patients Using Calcineurin Inhibitor-Free Immunosuppressive Protocols Based on T-Cell Adhesion or Costimulation Blockade. Transplantation 90: 1595-1601.

Rezania A, Bruin J E, Arora P, Rubin A, Batushansky I, Asadi A, O'Dwyer S, Quiskamp N, Mojibian M, Albrecht T, Yang Y H C, Johnson J D & Kieffer T J (2014) Reversal of diabetes with insulin-producing cells derived in vitro from human pluripotent stem cells. Nat. Biotechnol.

Rezania A, Bruin J E, Riedel M J, Mojibian M, Asadi A, Xu J, Gauvin R, Narayan K, Karanu F, O'Neil J J, Ao Z, Warnock G L & Kieffer T J (2012) Maturation of Human Embryonic Stem Cell-Derived Pancreatic Progenitors Into Functional Islets Capable of Treating Pre-existing Diabetes in Mice. Diabetes 61: 2016-2029.

Rezania A, Riedel M J, Wideman R D, Karanu F, Ao Z, Warnock G L & Kieffer T J (2011) Production of functional glucagon-secreting a-cells from human embryonic stem cells. Diabetes 60: 239-247.

Riedel M J, Asadi A, Wang R, Ao Z, Warnock G L & Kieffer T J (2011) Immunohistochemical characterisation of cells co-producing insulin and glucagon in the developing human pancreas. Diabetologia 55: 372-381.

Roark R, Itzhaki L & Philpott A (2012) Complex regulation controls Neurogenin3 proteolysis. Biol Open 1: 1264-1272.

Russ H A & Efrat S (2011) In-Vivo Functional Assessment of Engineered Human Insulin-Producing Cells (Artech House).

Schaffer A E, Freude K K, Nelson S B & Sander M (2010) Nkx6 Transcription Factors and Ptf1a Function as Antagonistic Lineage Determinants in Multipotent Pancreatic Progenitors. Developmental Cell 18: 1022-1029.

Schulz T C, Young H Y, Agulnick A D, Babin M J, Baetge E E, Bang A G, Bhoumik A, Cepa I, Cesario R M, Haakmeester C, Kadoya K, Kelly J R, Kerr J, Martinson L A, McLean A B, Moorman M A, Payne J K, Richardson M, Ross K G, Sherrer E S, et al (2012) A scalable system for production of functional pancreatic progenitors from human embryonic stem cells. PLoS ONE 7: e37004.

Seymour P A & Sander M (2011) Historical Perspective: Beginnings of the—Cell: Current Perspectives in—Cell Development. Diabetes 60: 364-376.

Shang L, Hua H, Foo K, Martinez H, Watanabe K, Zimmer M, Kahler D J, Freeby M, Chung W, Leduc C, Goland R, Leibel R L & Egli D (2014) B-cell dysfunction due to increased ER stress in a stem cell model of Wolfram syndrome. Diabetes 63: 923-933.

Shapiro A M, Lakey J R, Ryan E A, Korbutt G S, Toth E, Warnock G L, Kneteman N M & Rajotte R V (2000) Islet transplantation in seven patients with type 1 diabetes mellitus using a glucocorticoid-free immunosuppressive regimen. N. Engl. J. Med. 343: 230-238.

Shih H P, Kopp J L, Sandhu M, Dubois C L, Seymour P A, Grapin-Botton A & Sander M (2012) A Notch-dependent molecular circuitry initiates pancreatic endocrine and ductal cell differentiation. Development 139: 2488-2499.

Shim J-H, Kim J, Han J, An S Y, Jang Y J, Son J, Woo D-H, Kim S-K & Kim J-H (2014) Pancreatic islet-like three dimensional aggregates derived from human embryonic stem cells ameliorate hyperglycemia in streptozotocin induced diabetic mice. cell transplant.

Szot G L, Koudria P & Bluestone J A (2007) Transplantation of Pancreatic Islets Into the Kidney Capsule of Diabetic Mice. J Vis Exp.

Szot G L, Yadav M, Lang J, Kroon E, Kerr J, Kadoya K, Brandon E P, Baetge E E, Bour-Jordan H & Bluestone J A (2014) Tolerance Induction and Reversal of Diabetes in Mice Transplanted with Human Embryonic-Stem-Cell-Derived Pancreatic Endoderm. Cell Stem Cell.

Tudurí E & Kieffer T J (2011) Reprogramming gut and pancreas endocrine cells to treat diabetes. Diabetes, Obesity and Metabolism 13 Suppl 1: 53-59.

Van Hoof D, Mendelsohn A D, Seerke R, Desai T A & German M S (2011) Differentiation of human embryonic stem cells into pancreatic endoderm in patterned size-controlled clusters. Stem Cell Res 6: 276-285.

Xu X, Browning V & Odorico J S (2011) Activin, BMP and FGF pathways cooperate to promote endoderm and pancreatic lineage cell differentiation from human embryonic stem cells. Mech. Dev.

Zhou Q & Melton D A (2008) Extreme makeover: converting one cell into another. Cell Stem Cell 3: 382-388.

Example 7

Re-Aggregation of Induced Beta-Like Cells Improves Yield and Functionality

Human pluripotent stem cells (hPSCs) have been successfully coaxed down the pancreatic lineage into functional insulin-producing cells in vitro, using 3D and planar cell culture systems. However, these protocols generate a mixed population of pancreatic progenitors that are yet uncommitted to the endocrine lineage and insulin-producing cells that are potentially in the process of maturation. It has become apparent that this heterogeneous population is significantly distinct from adult islets, which are mainly composed of fully matured endocrine cells. Developmental studies in mice have shown that early endocrine-committed precursors delaminate from the pancreatic epithelium, cluster together, and then undergo their final maturation secluded from the epithelial niche.

Figure 12:
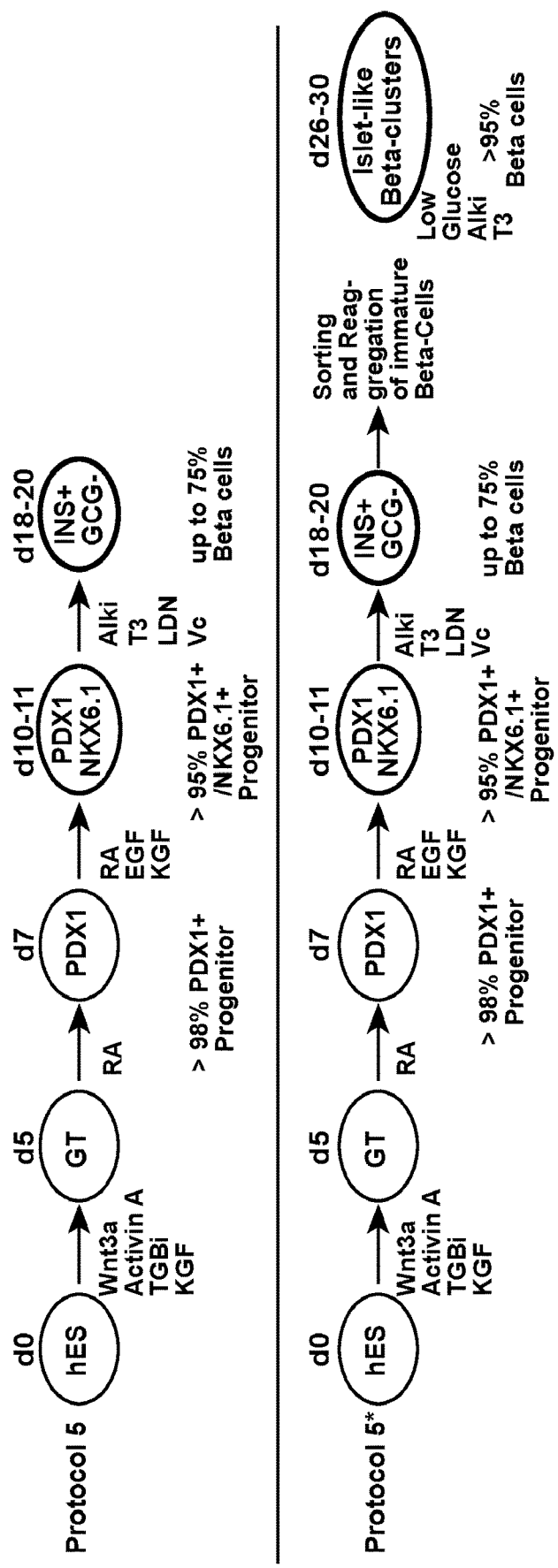
FIG. 12. Schematic illustrations of beta cell induction protocols. A linear flowchart is presented for two exemplary beta cell induction protocols, one of which involves induction of insulin-producing cells at levels up to 75% of cells in the culture (Protocol 5) and a variant on that protocol (Protocol 5*) that further provides for sorting immature beta cells and re-aggregation of immature beta cells to produce mature beta cells at levels greater than 95% of cells in the culture.

FIG. 12 presents a couple of exemplary beta-like cell induction protocols. Protocol 5 incubates human embryonic stem cells in media comprising Wnt3a, Activin A, TGF-β inhibitor and KGF for five days, following which the cells are exposed to media comprising retinoic acid for two days to yield greater than 98% PDX-1+ progenitor cells. These cells are then exposed to media comprising retinoic acid, epidermal growth factor and keratinocyte growth factor for 3-4 days to yield greater than 95% PDX-1+/NKX6.1+ progenitor cells. The PDX-1+/NKX6.1+ cells are then exposed to media comprising anaplastic lymphoma kinase inhibitor, T3 thyroid hormone, LDN and vitamin C for 7-10 days to yield up to 75% beta cells that are insulin+ and glucagon−. To overcome the heterogeneity in the differentiation protocols and to provide a more suitable endocrine-rich niche, an effort was made to re-aggregate the newly generated insulin-producing cells. FIG. 12 presents a schematic of an exemplary mature beta cell induction protocol involving re-aggregation as Protocol 5*. Extending beyond Protocol 5, there is a step for sorting beta cells by developmental age and a re-aggregation step for immature beta cells. Beta-like cells are re-aggregated into about 100-150 μm islet-sized clusters with about 500-2000 cells/cluster in Aggrewells, the GravityPLUS Hanging Drop System, or Perfecta3D Hanging Drop Plates in media comprising low glucose, anaplastic lymphoma kinase inhibitor and T3 thyroid hormone, and further cultured for 6-12 days to yield enhanced beta clusters (eBCs). These eBCs consist of up to 90% monohormonal C-peptide+ glucagon− beta cells. More particularly, using a human embryonic stem cell (hESC) line that has GFP knocked into the insulin gene locus, insulin-producing beta-like cells were sorted by FACS and the beta-like cells were re-aggregated into clusters that are comparable in size to human islets. The re-aggregated clusters demonstrate significantly greater functional properties than a non-enriched ES-derived beta cell population, both in vitro and in vivo. In vitro, these clusters showed improved insulin secretion during dynamic glucose perifusion. In vivo, these clusters secrete human C-peptide in response to a glucose challenge as early as three days following transplantation. This instantaneous ability to function has not been reported so far with human ES-derived beta cell populations, and it further establishes that these re-aggregated beta-clusters are very similar to their islet counterparts. In summary, a new strategy was devised to isolate and generate homogeneous and highly pure islet-like endocrine clusters that yields cell clusters having enhanced functional capacity in vitro and in vivo. It is expected that these clusters will function as glucose-responsive beta cells useful in treating disease and would be useful in transplantation approaches to disease treatment.

INTRODUCTION

Recently, we and others have demonstrated the generation of insulin-producing cells in vitro from human pluripotent stem cells[1,2,3]; however, a heterogeneous population of uncommitted pancreatic progenitors (about 60-70%) and immature insulin-producing cells (about 30-40%) are produced in these studies.

These insulin-producing cells do not exhibit robust response to glucose in dynamic perifusion assays, indicating that they are not mature or equivalent to islet beta cells.

During development, endocrine commitment is followed by delamination from the pancreatic epithelium, migration and clustering of newly born endocrine cells. It is in these clusters that islet cells, including beta cells, mature into functional cells. Re-aggregation of newly generated beta cells into clusters resembling islets leads to maturation and improved functional properties.

Generation of Insulin-Producing Beta-Like Cells from hESCs.

Figure 13:
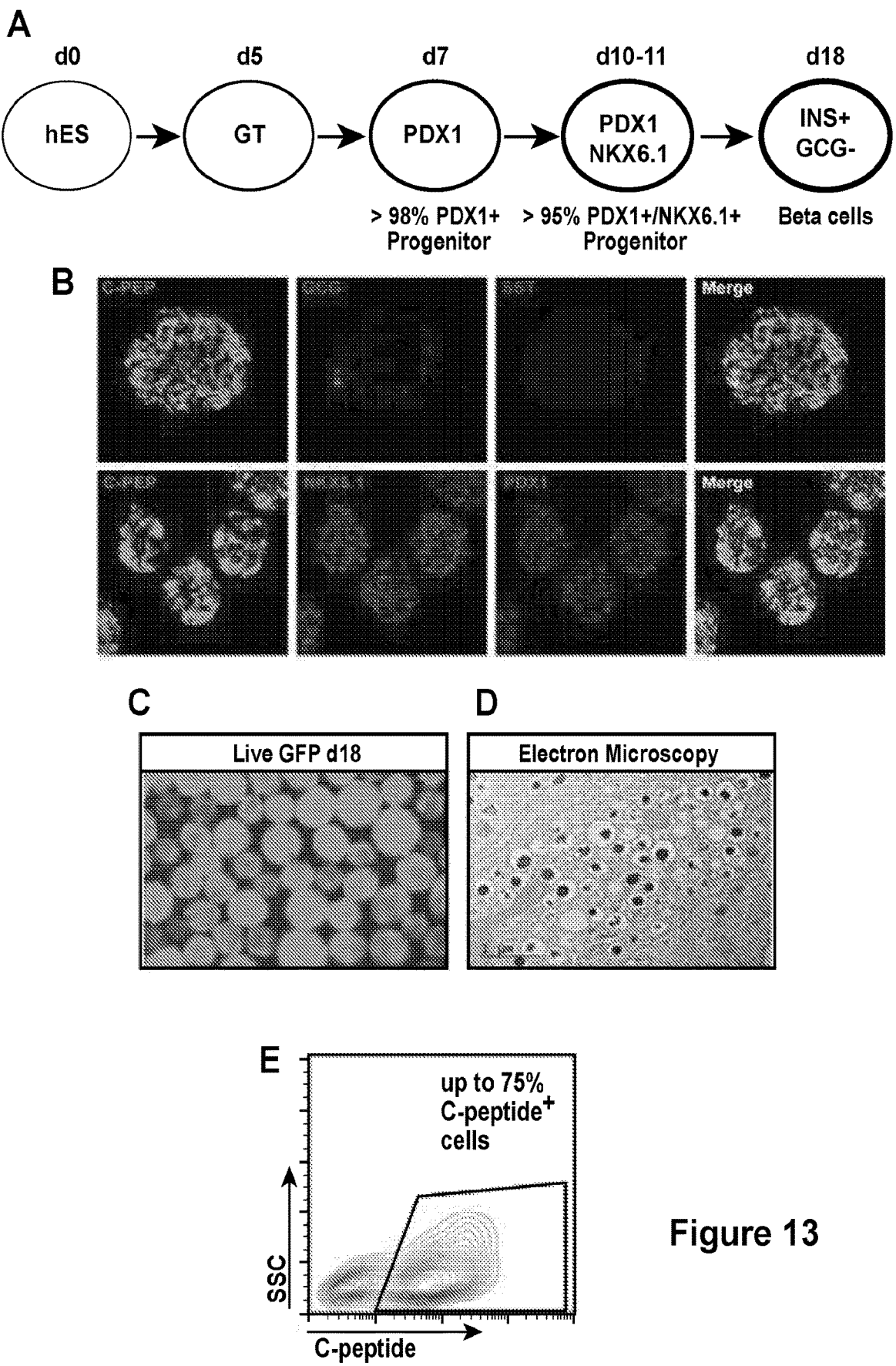
FIG. 13. Generation of insulin-producing beta-like cells from hESCs. (A) Schematic of a differentiation protocol to generate β-like cells. (B, C) Micrographs of differentiated clusters at day 19 (D19) and intra-cellular PDX1, NKX6.1, C-peptide, Glucagon and Somatostatin staining of differentiated cells. (D) Transmission electron microscopy image shows secretory vesicles. (E) Flow cytometric quantification of C-peptide expression.

In FIG. 13, (A) Schematic of a differentiation protocol to generate β-cells. (B, C) Micrograph of differentiated clusters at day 19 (D19) and intra-cellular PDX1, NKX6.1, C-peptide, Glucagon and Somatostatin staining of differentiated cells. (D) Transmission electron microscopy image shows secretory vesicles. (E) Flow cytometric quantification of C-peptide expression.

The strategy for re-aggregation of beta cells involved generating immature beta-like cells as described herein and subjecting such cells at day 19-20 of culture to a sorting procedure to enrich for beta-like cells, followed by at least two days of incubation to allow the beta-like cells to self-organize into enhanced beta clusters (eBCs).

Beta-Clusters are Highly Enriched in Bona Fide Beta Cell Markers.

Figure 14:
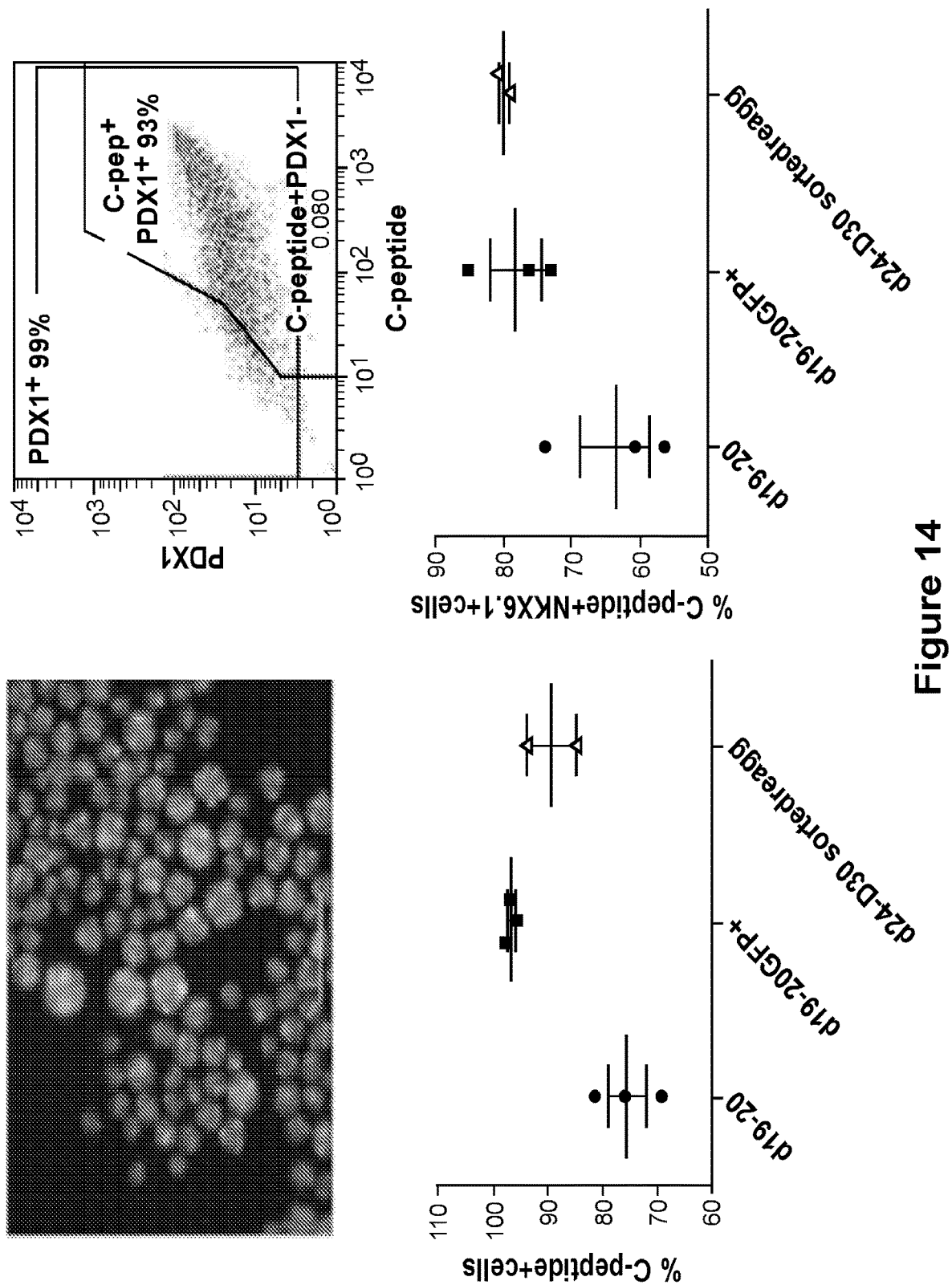
FIG. 14. Enhanced Beta-clusters (eBCs) are highly enriched in bonafide beta cell markers. (A) eBCs are mostly GFP$^+$. (B) FACS plot of D26 eBCs showing about 93% of cells are C-peptide and PDX1 co-positive. (C, D) Quantitative FACS analysis indicates enrichment and maintenance of C-peptide$^+$ cells, and C-peptide and NKX6.1 co-expressing cells.

In FIG. 14, (A) Day26 (D26) re-aggregated Beta-clusters are mostly GFP+. (B) FACS plot of D26 beta-clusters showing about 93% of cells are C-peptide and PDX1 co-positive. (C, D) Quantitative FACS analysis indicates enrichment and maintenance of C-peptide+ cells, and C-peptide and NKX6.1 co-expressing cells.

Figure 15:
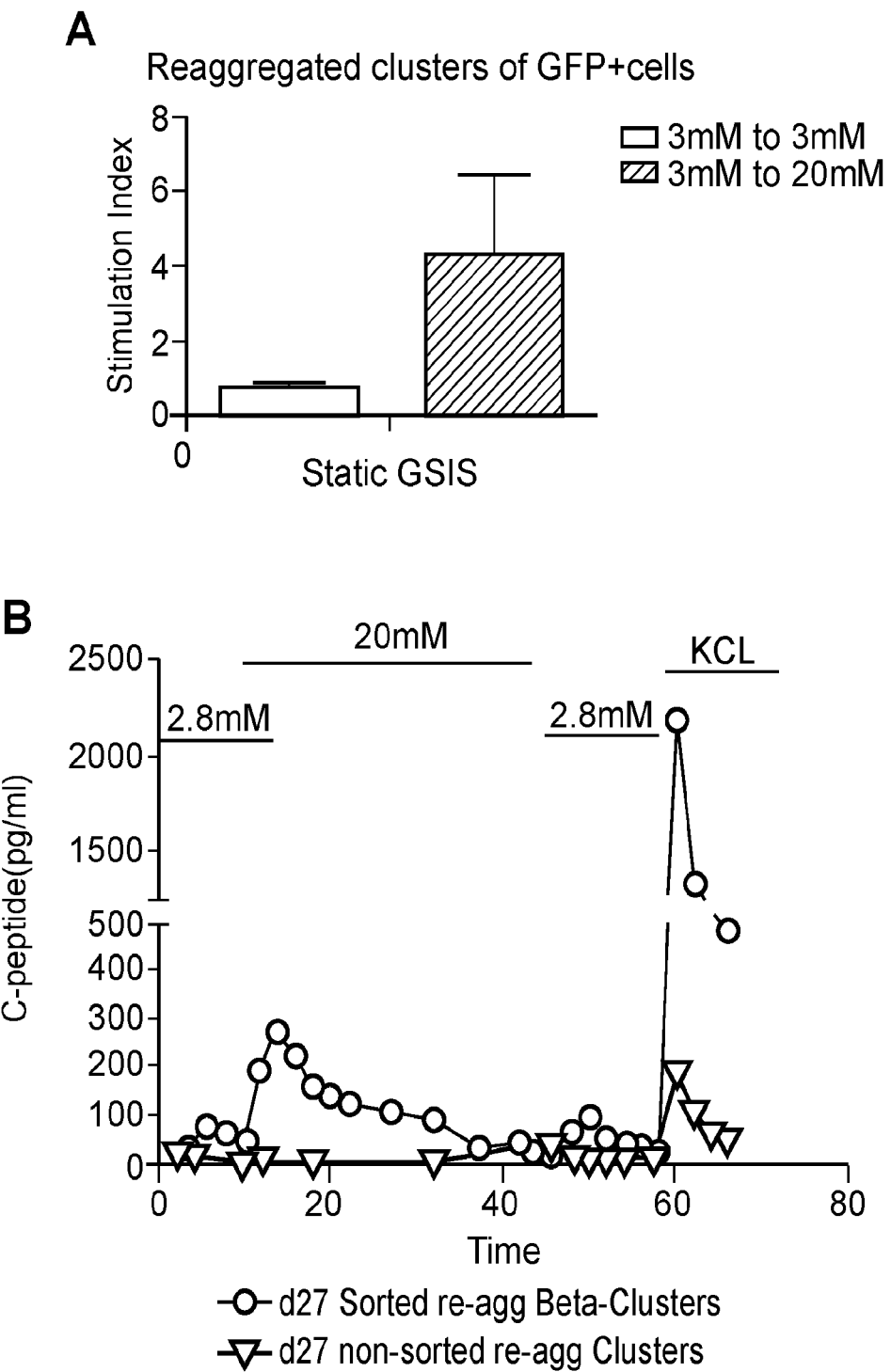
FIG. 15. Beta-clusters demonstrate greater functional properties than a non-enriched hESC-derived beta cell population, in vitro. (A) Beta-clusters exhibit a high stimulation index in static glucose-stimulated insulin secretion experiments. (B) In dynamic perifusion experiments, sorted, re-aggregated Beta-clusters display a glucose response profile similar to human islets, whereas non-enriched, re-aggregated, hESC-derived populations do not show a biphasic response.

Beta-clusters demonstrate significantly greater functional properties than non-enriched hESC-derived beta cell population, in vitro. In FIG. 15, (A) Beta-clusters exhibit a high stimulation index in static glucose stimulated insulin secretion experiments. (B) In dynamic perifusion experiments, sorted re-aggregated Beta-clusters display similar glucose response profile like human islets whereas non-enriched, re-aggregated hESC-derived populations do not show a biphasic response.

Beta-Clusters Possess Highly Coupled Mitochondria.

Figure 16:
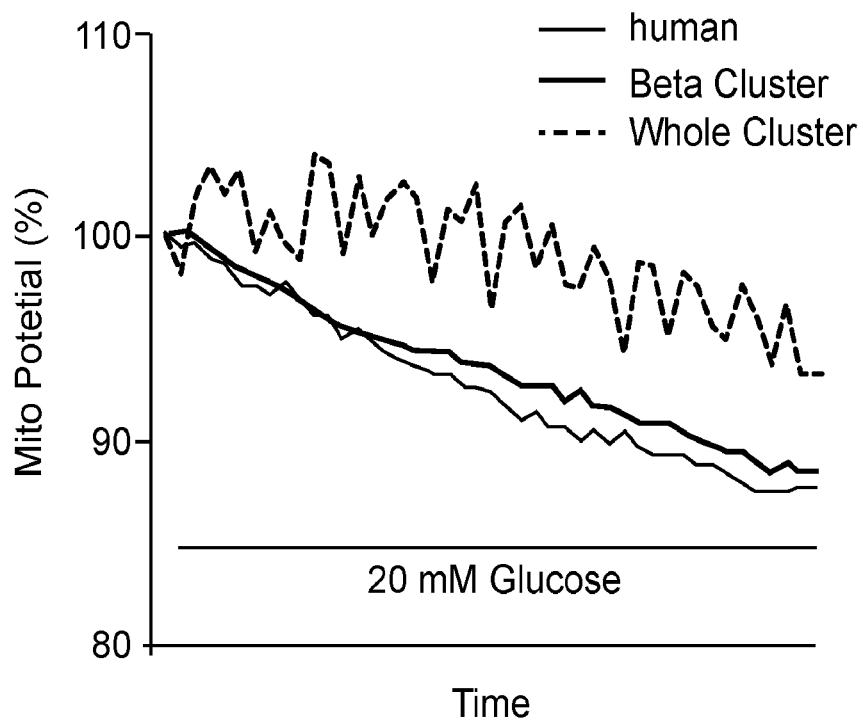
FIG. 16. Beta-clusters possess highly coupled mitochondria. On exposure to high glucose, the mitochondrial membrane potential in Beta-clusters decreases in a manner similar to human islets.

On exposure to high glucose, the mitochondrial membrane potential in Beta-clusters decreases in a similar fashion to human islets, as shown in FIG. 16.

Beta-Clusters Show Biphasic Calcium Response to Glucose.

Figure 17:
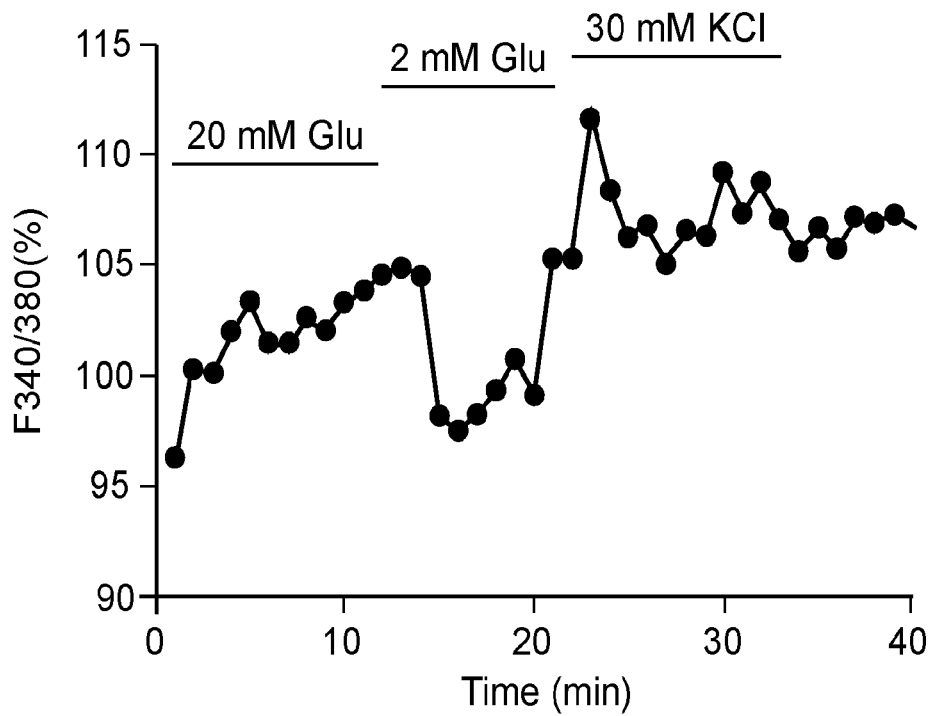
FIG. 17. Beta-clusters show biphasic calcium response to glucose. Single clusters were perifused with KRB containing varying amounts of glucose and KCL in microfluidic chambers, and the percent F340/380 was plotted as a function of time. The fluorescence ratio of emissions at 505 nm of Fura-2AM dye excited at 340 nm and 380 nm was converted to a percentage and plotted against time to show the level of free intracellular $Ca^{2+}$.

Single clusters were perifused with KRB containing varying amounts of glucose and KCL in microfluidic chambers, with the results shown in FIG. 17.

Beta-Clusters Function In Vivo.

Figure 18:
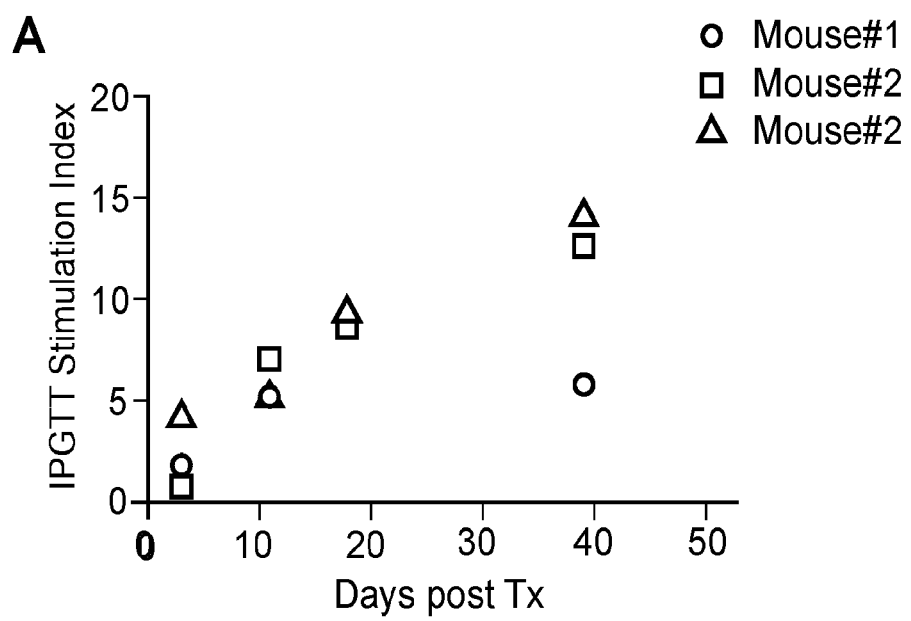
FIG. 18. Beta-clusters function in vivo. (A) Beta-clusters were transplanted into NSG mice, and their functionality was evaluated over 45 days. Intra-peritoneal glucose challenge indicated that they secrete c-peptide as early as three days post-transplant, and maintain robust functionality up until at least 45 days. (B) Grafts show islet-like regions with C-peptide+ beta cells and alpha cells organized together in clusters.
Figure 18:
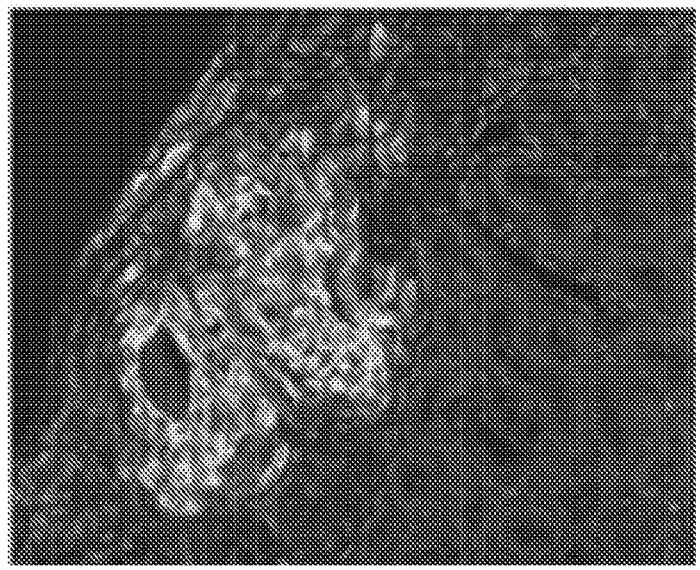

In FIG. 18, (A) Beta-clusters were transplanted into NSG mice, and their functionality was evaluated over 45 days. Intra-peritoneal glucose challenge indicated that they secrete c-peptide as early as three days post-transplant, and maintain robust functionality up until at least 45 days. (B) Grafts show islet-like regions with C-peptide+ beta cells and alpha cells organized together in clusters.

Conclusions

Current beta cell differentiation protocols from hPSCs do not generate homogeneous populations of mature beta cells. In the work disclosed herein, protocols were developed that recapitulated endocrine cell clustering that occurs during the maturation process in embryonic development by sorting and re-aggregating beta cells formed from an Ins-GFP hES cell line. Re-aggregated Beta-clusters are highly enriched for beta cell markers, including c-peptide, PDX1, and NKX6.1, compared to the heterogeneous populations generated during differentiation. The Beta-clusters maintain high levels of expression of these critical genes on prolonged cell culture. Moreover, these Beta-clusters demonstrate significantly better functional properties. In vitro, these clusters showed an improved stimulation in static glucose-stimulated insulin secretion assays and dynamically secrete human C-peptide in perifusion systems in a similar fashion to human islets. They show a decrease in their mitochondrial potential upon stimulation and exhibit a biphasic calcium response to glucose akin to human islets. In vivo, these clusters secrete human C-peptide in response to glucose challenge as early as three days following transplantation and are functional at least until 45 days post transplant. In summary, a new technique to isolate and generate homogeneous and highly pure islet-like endocrine clusters that have enhanced functional capacity has been developed, as disclosed herein.

REFERENCES FOR EXAMPLE 7 ONLY

1. Rezania, et al. *Nature Biotech* 32, 1121-1133, 2014.
2. Pagliuca, et al. *Cell* 159(2), 428-439, 2014.
3. Russ, et al. *EMBO J* 34(13), 1759-1772, 2015.
4. Nair, et al. *Curr. Op in Genetics & Dev.* 32, 171-180, 2015.

Example 8

Figure 19:
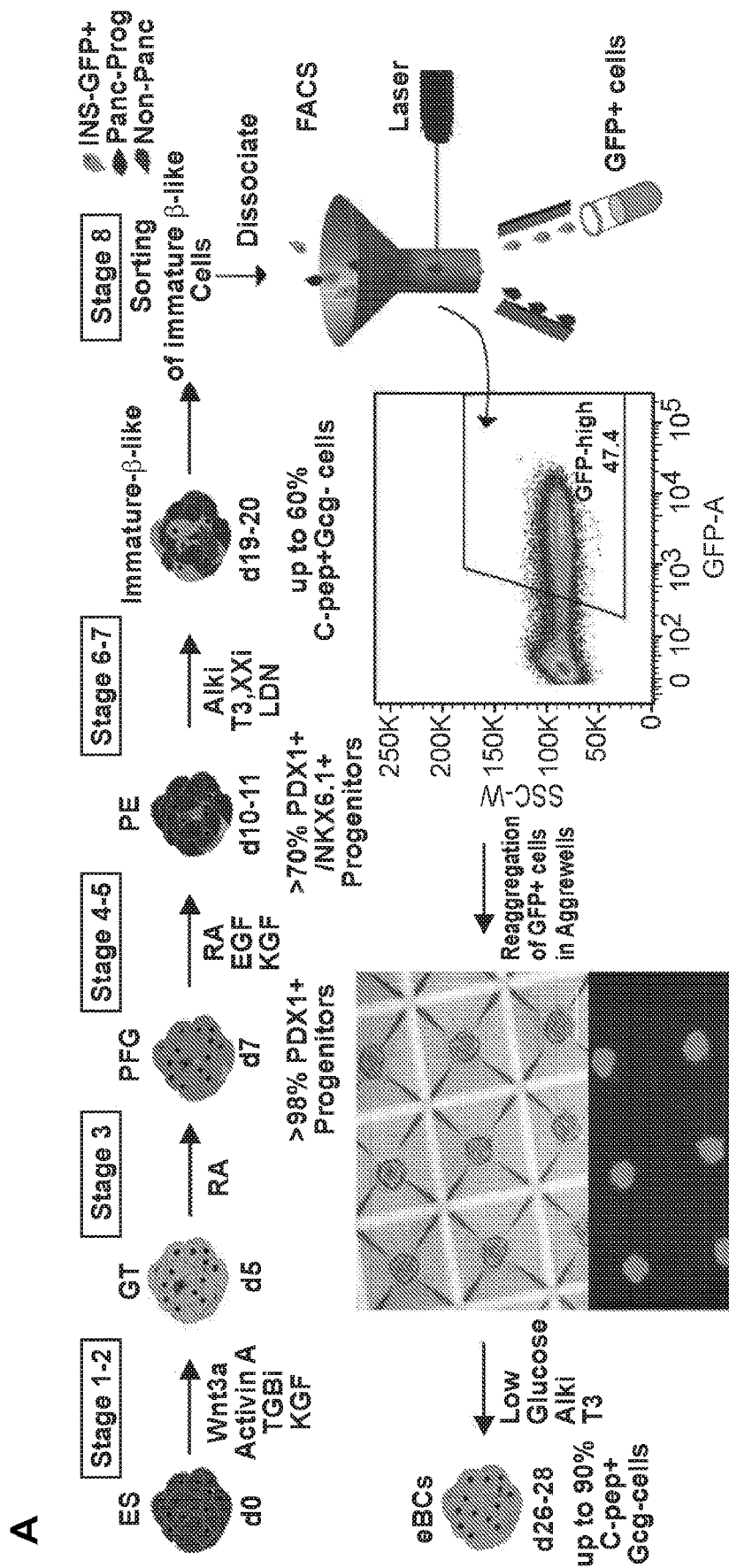
FIG. 19. Generation of Islet-like enhanced Beta-clusters (eBCs). (A) Schematic representation of directed differentiation of hESCs to pancreatic β-cells through 26-28 days that recapitulates embryonic development and includes a new strategy of re-aggregation of immature β-like cells to mimic β-cell coalescence into islets. Immature $INS^{GFP}$+β-like cells were isolated by FACS from d19-20 (day 19-20) spheres, and subsequently re-aggregated into 100 μm-sized eBCs in Aggrewell™-400 microwells. Scale bar, 200 μm. (B) Immunofluorescent staining of d26-27 eBCs for C-peptide (C-PEP), glucagon (GCG), somatostatin (SST), and nuclei (DAPI), indicating that the majority of cells are C-peptide+ and monohormonal. Arrows indicate C-peptide+/glucagon+ or C-peptide+/somatostatin+ cells. Scale bar, 100 μm. (C) Quantitative analysis of d26-27 eBCs by flow cytometry, confirming that the majority of the cells are C-peptide+/NKX6.1+/glucagon−. (D) Flow cytometry quantification of co-expression of C-peptide and various key β-cell markers such as NKX6.1, PDX1, CHGA, NEUROD1, PAX6, ISL1, and NKX2.2, and C-peptide+/glucagon− cells before (d19-20, blue circles) and after, sorting and re-aggregation (d26-27, green squares). n=3-10 biological replicates. Error bars indicate SEM. *P<0.01, P<0.001, *P<0.0001 determined using the Holm-Sidak method with alpha=0.05.
Figure 19:
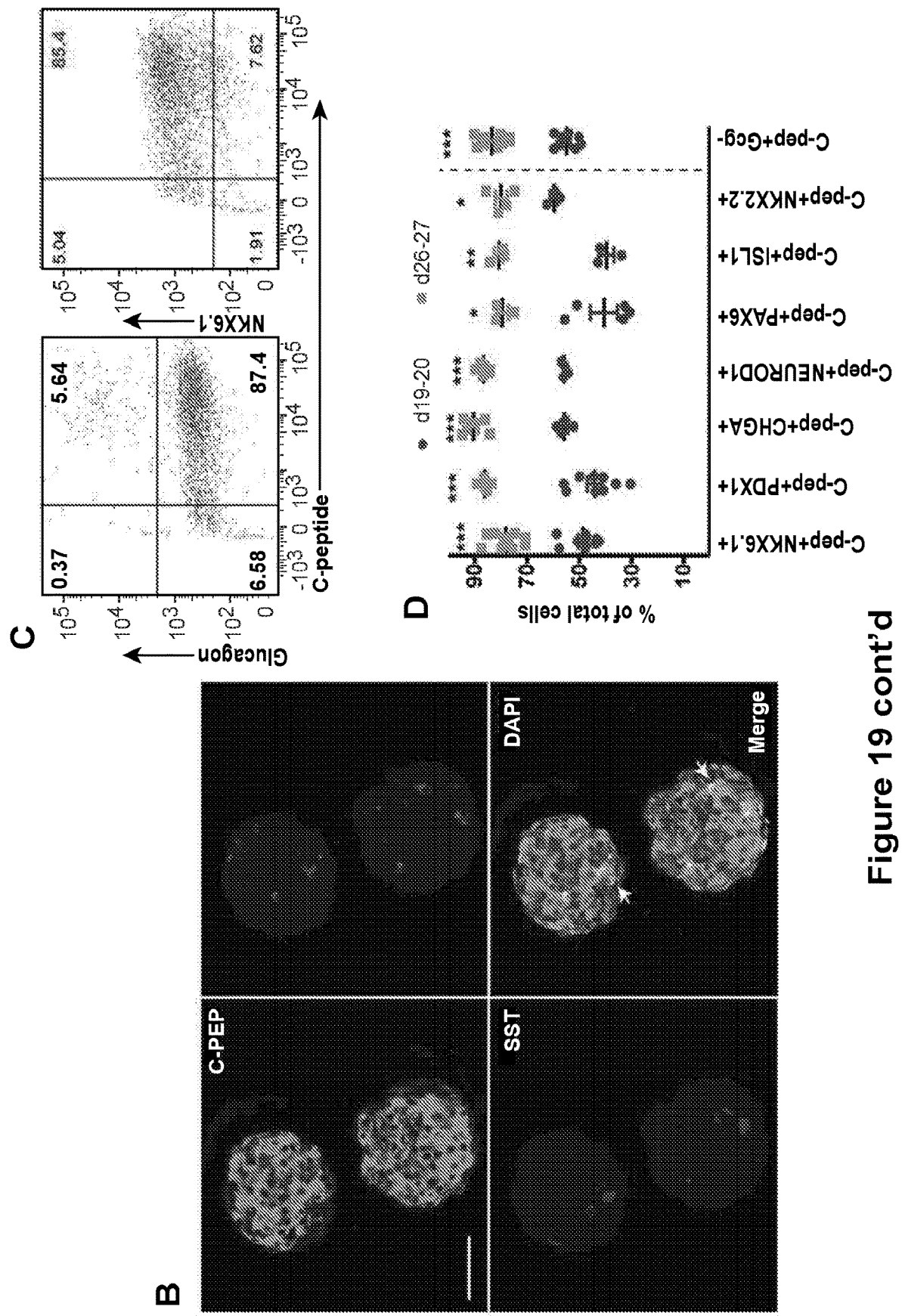
Figure 29:
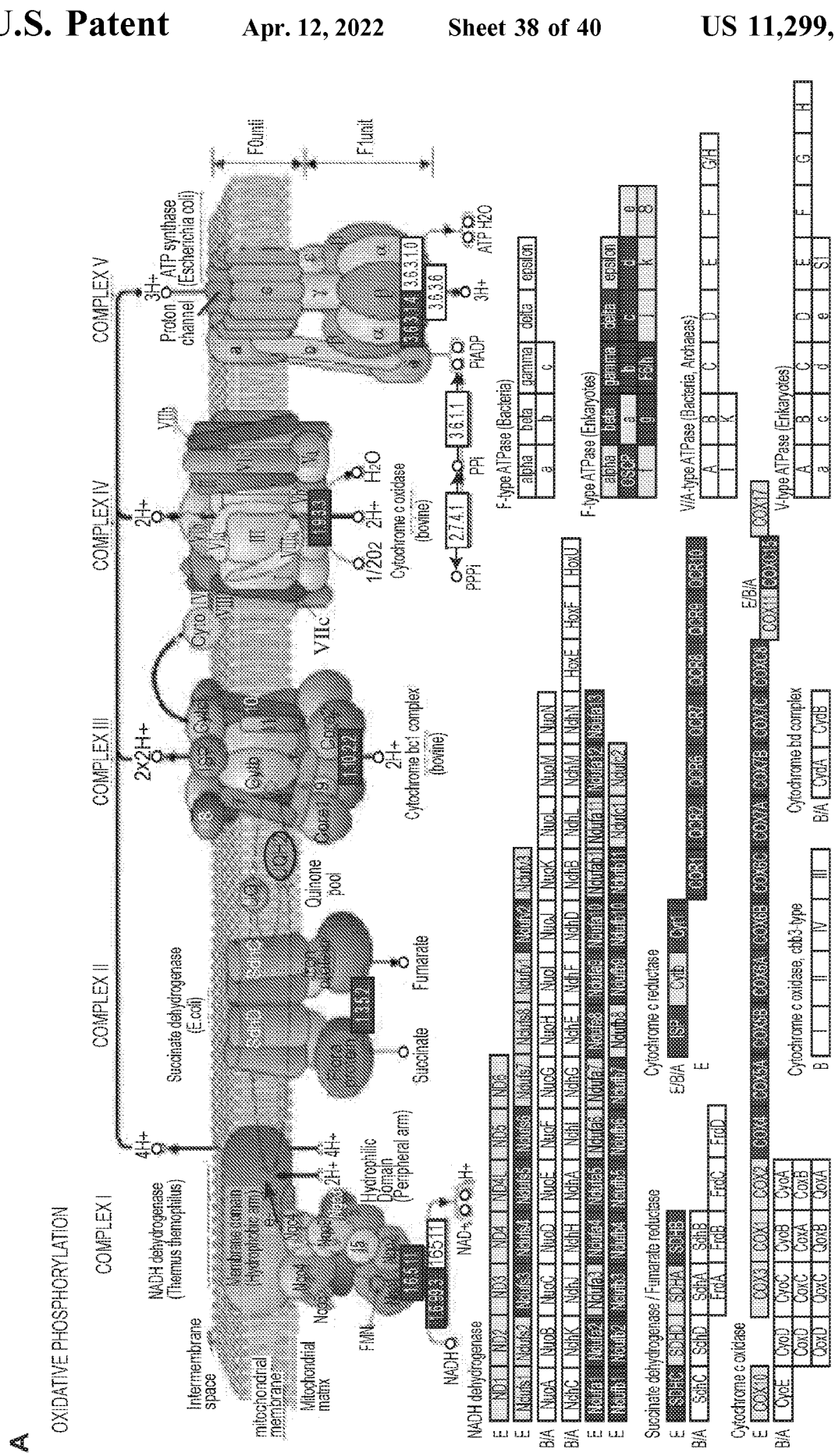
FIG. 29. Electron transport chain genes are upregulated in β-cells of eBCs. Schematic depicting top responsive genes upregulated in β-cells of eBCs compared to β-cells of d20 immature clusters using the gene ontology terms: electron transport chain, mitochondrial respiratory chain complex 1 biogenesis and mitochondrial ATP synthesis-coupled proton transport. Responsive genes are marked in red against a green background for human-specific isoforms, mapped on the OXPHOS pathway using KEGG mapper.

Recapitulating Endocrine Cell Clustering Promotes Coalescence into Islet-Like Structures In Vitro The end product of current β-cell differentiation protocols consists of a mixed population of PDX1$^+$ NKX6.1$^+$ pancreatic progenitors and differentiated endocrine cells that have not yet reached full maturity, in addition to less defined lineages and potentially rare undifferentiated stem cells. Importantly, these protocols do not recapitulate the critical process of endocrine cell clustering that occurs during islet formation in vivo, which is a prerequisite for functional maturation[21, 22, 24]. To address this problem and mimic endocrine cell coalescence into islets, we sought to remove progenitor cells and re-aggregate hPSC-derived-β-like-cells into clusters. Using the INS$^{GFP/W}$ reporter cell line, we first optimized the differentiation protocol to efficiently generate up to 60% C-peptide$^+$ Glucagon$^-$ monohormonal cells in 19-20 days (mean±SEM=54.8±1.5%)(FIG. 19A) in 3D suspension cultures. A large proportion of the cells were co-positive for C-peptide and key β-cell markers (Table 4, FIGS. 22F and 29). Routinely, cell markers were identified by immunostaining using conventional staining protocols and commercially available antibodies, as indicated in Tables 1 and 2. Next, we incorporated a re-aggregation step by dissociating day-20 (d20) spheres and sorting live INS$^{GFP+}$ β-like-cells by flow cytometry. In a typical experiment, about 45-50% GFP-high cells were collected and re-aggregated into clusters in pre-patterned chambers of Aggrewell™-400 plates at a density of 1000 cells/cluster (FIG. 19B). Sorted cells self-organize into about 100 am-sized islet-like clusters after two days (FIG. 19C). This cluster size was carefully chosen to mimic the average size and number of β-cells in one-human islet equivalent[26]. The GFP- sorted and re-aggregated clusters were cultured in low-glucose CMRL-based media with T3 and ALK5 inhibitor (Alki) for additional 5 days, and henceforth were referred to as enriched Beta-clusters (eBCs).

Figure 25:
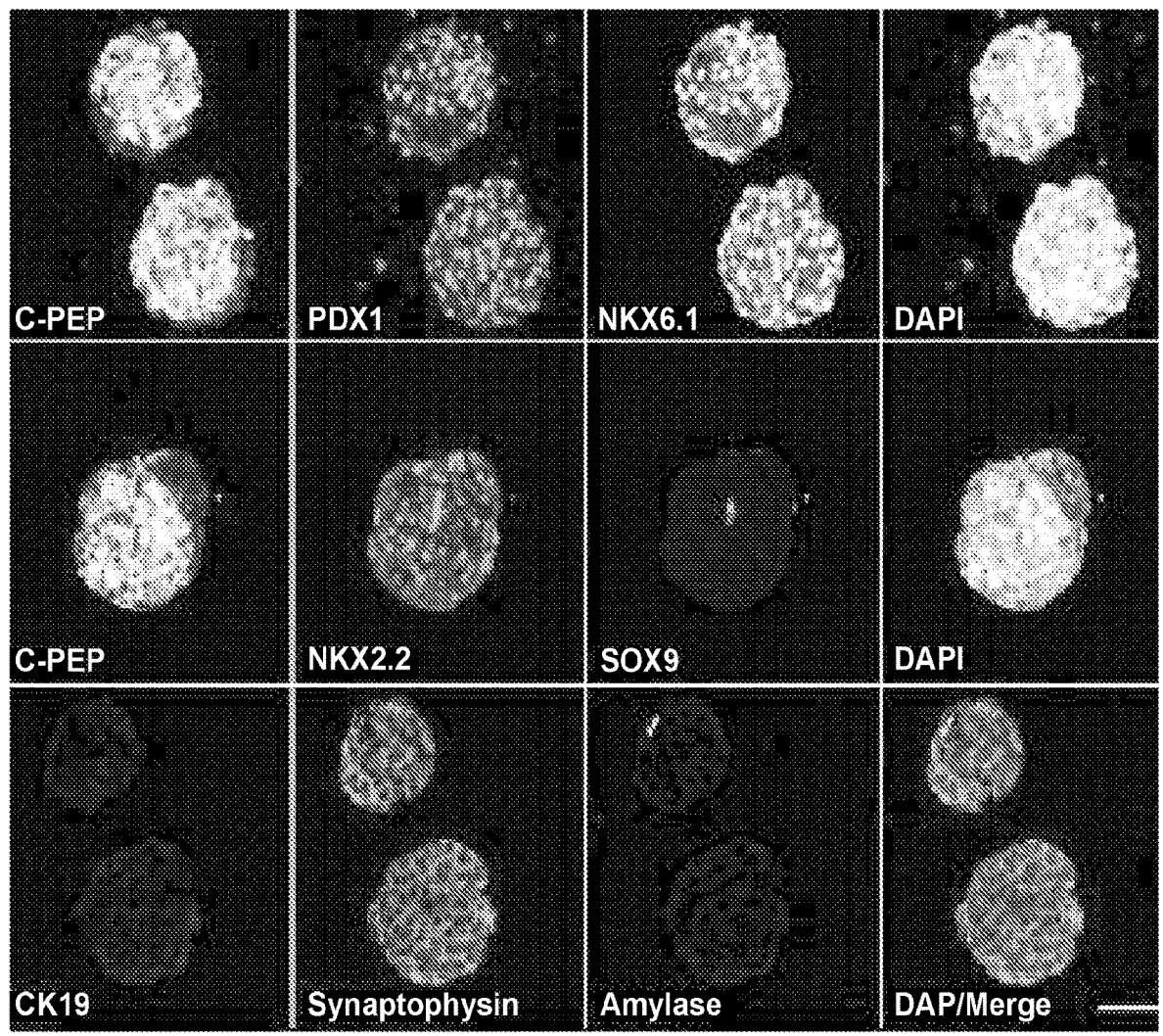
FIG. 25. Immunofluorescence staining characterization of d26-27 eBCs. Confocal images of eBCs stained for C-peptide (C-PEP) and the hallmark β-cell transcription factors, PDX1 and NKX6.1 (Upper panel). Co-staining for C-peptide, NKX2.2 and SOX9 (marker for progenitors and duct cells) (middle panel). Co-staining for synaptophysin (endocrine), amylase (acinar) and CK19 (ducts) (lower panel). Scale bar, 100 μm.
Figure 26:
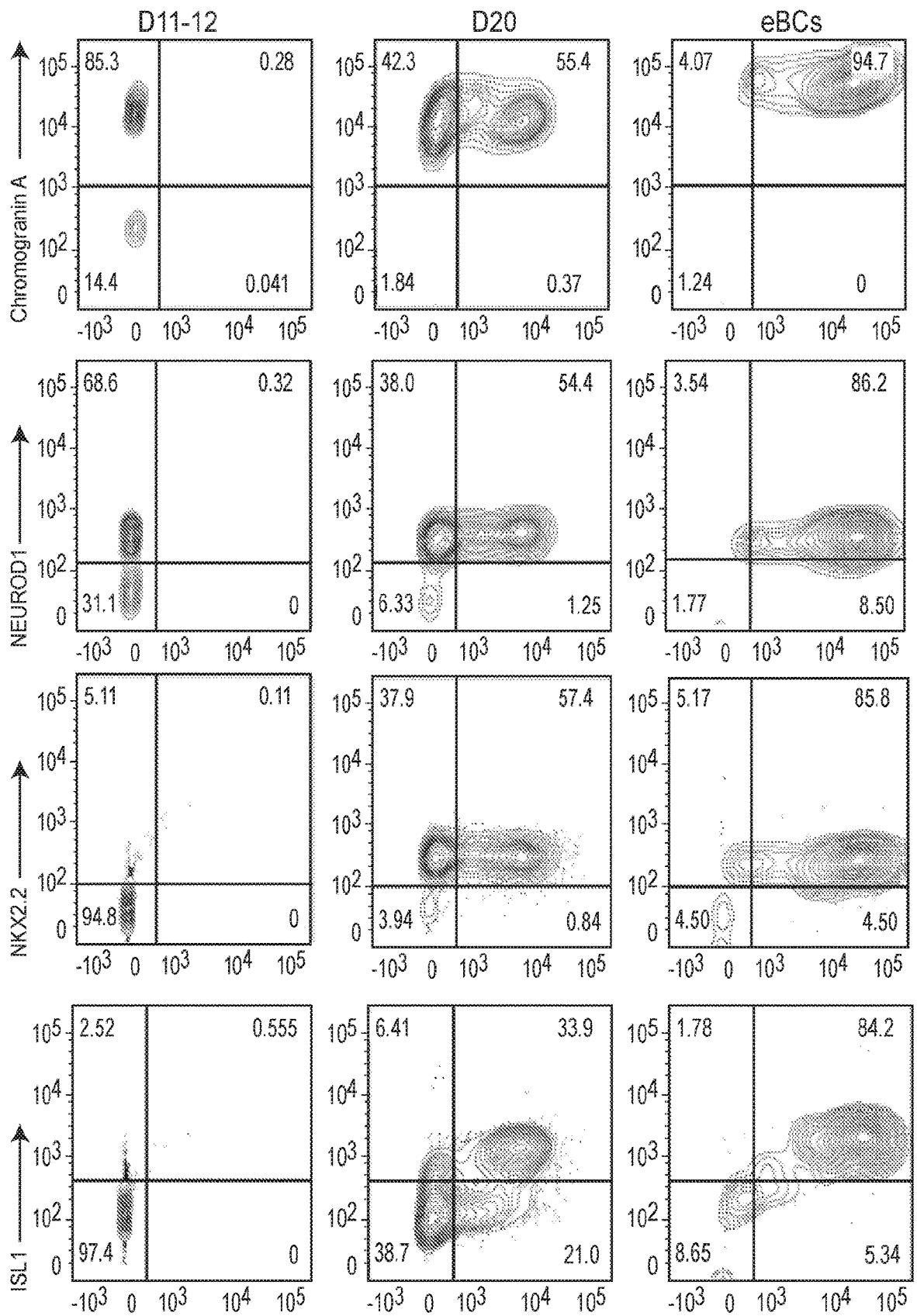
FIG. 26. Quantitative and temporal analysis of the appearance of key β-cell and endocrine markers over the course of endocrine differentiation (d11-d27). Representative flow cytometry plots of cell populations co-stained with C-peptide and markers for the endocrine lineage, such as Chromogranin A, NEUROD1, NKX2.2, ISL1, and PAX6, as well as β-cell-enriched markers including PDX1 and NKX6.1. Note the low level of c cells, marked by expression of Glucagon, throughout the differentiation process.
Figure 26:
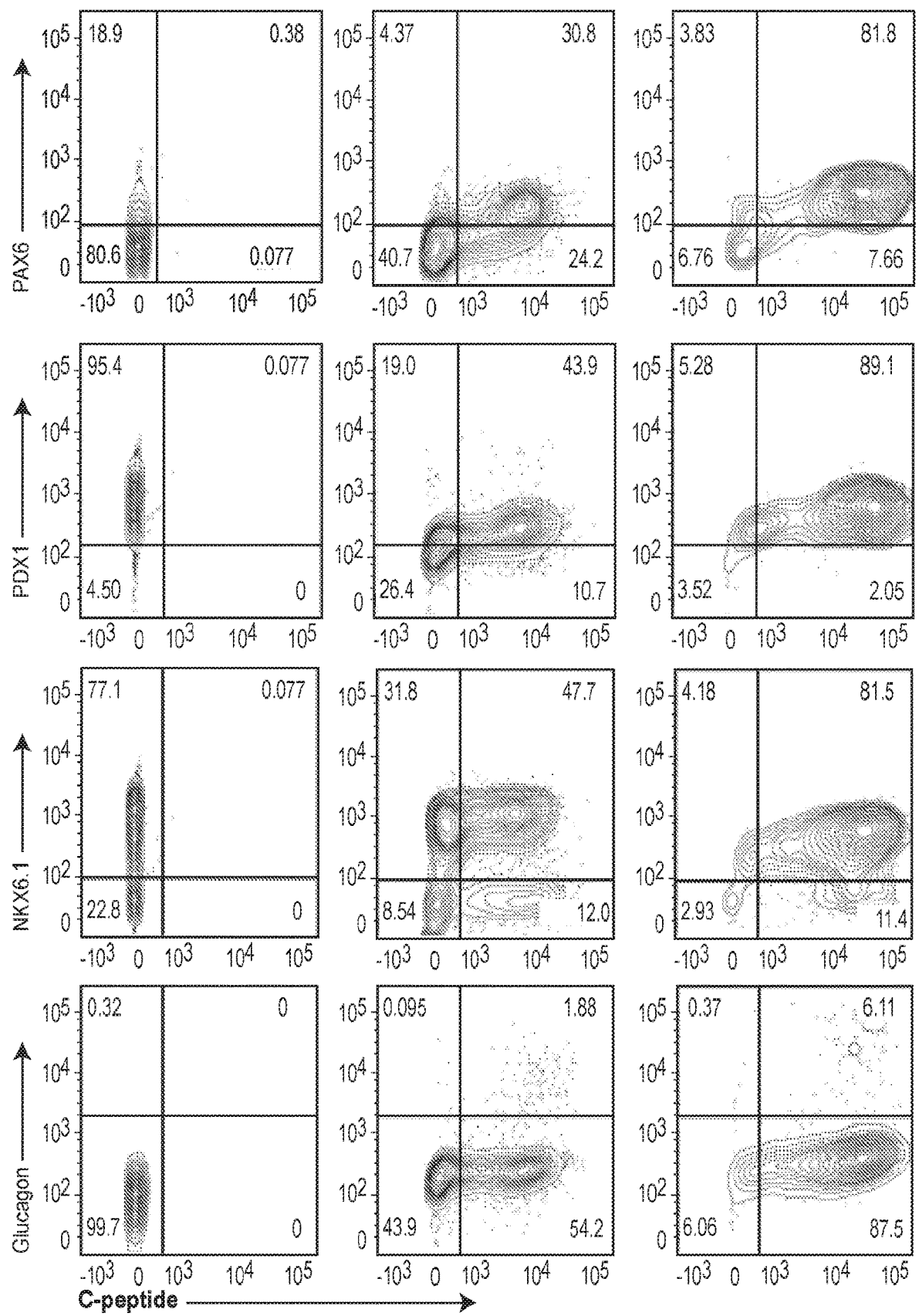

At day 26-27 (d26-27), eBCs are exclusively endocrine with about 95% of cells expressing chromogranin A (FIG. 26) and all cells staining positive for synaptophysin (FIG. 25, lower-panel). Cell types of the exocrine pancreatic lineages, namely duct and acinar cells marked by staining for SOX9 (FIG. 25, middle-panel), CK19 or amylase (FIG. 25, lower-panel), respectively, are almost completely absent. Within the endocrine cell subtypes, eBCs mainly consist of monohormonal C-peptide$^+$ cells and rare cells co-expressing C-peptide and Glucagon/Somatostatin (FIG. 19D). Quantitatively, up to about 90% (mean±SEM=83.5±1.7%) of the cells are C-peptide$^+$ Glucagon$^-$, and only about 4-12% (mean±SEM=8.6±0.9%) are C-peptide and Glucagon co-positive (FIG. 19E). Up to 87% (mean±SEM=78.1±1.8%) of eBC-cells co-express C-peptide and NKX6.1, a transcription factor essential for maintaining the functional state of 0-cells [27] (FIG. 19E). Specifically, nuclear staining of NKX6.1 and PDX1 were observed in C-peptide$^+$ cells (FIG. 25, upper-panel). Furthermore, when compared with d19-20 clusters, re-aggregation followed by one week of extended culture resulted in significant enrichment of cells co-positive for C-peptide and many other key β-cell markers in eBCs (Table 4, FIG. 19F). Of note, re-aggregation also depletes undifferentiated pancreatic epithelial progenitors (PDX1$^+$/NKX6.1$^+$/C-peptide-) (Table 4, FIG. 26). A time course analysis of endocrine differentiation from d11 to d27 by flow cytometry demonstrates progressive appearance, enrichment, and maturation of C-peptide$^+$ cells through increasing expression of endocrine/β-cell specific markers. Importantly, we observed a marked increase in the intensity of C-peptide expression in eBCs compared with β-like-cells at d20. Similar patterns were also observed in intensities of transcription factors such as PDX1, ISL11 and PAX6, and dense core granule component chromograninA (FIG. 26). Summarily, our data indicate that re-aggregation of immature β-like-cells followed by extended culture for another week results in phenotypic maturation of hPSC-derived-β-cells.

TABLE 4

| Population | Percentage of total cells | |
|---|---|---|
|  | d19-20 | d26-27 eBCs |
| C-peptide+Glucagon− | 54.8 ± 1.5 | 83.5 ± 1.7 |
| C-peptide+PDX1+ | 44.2 ± 2.8 | 86.1 ± 1.2 |
| C-peptide+NKX6.1+ | 48.7 ± 1.8 | 78.1 ± 1.8 |
| C-peptide+NKX2.2+ | 59.7 ± 1.5 | 79.9 ± 2.4 |
| C-peptide+PAX6+ | 40.7 ± 5.2 | 79.3 ± 2.2 |
| C-peptide+ISL1+ | 39.7 ± 2.9 | 80.8 ± 1.7 |
| C-peptide+NEUROD1+ | 55.7 ± 0.5 | 86.5 ± 0.9 |
| C-peptide+Chga+ | 55.8.7 ± 1.4 | 90.4 ± 1.8 |
| C-peptide−PDX1+ | 24.5 ± 2.4 | 3.2 ± 0.7 |
| C-peptide−NKX6.1+ | 36.9 ± 1.7 | 5.5 ± 0.3 |
| PDX1+NKX6.1+C-peptide− | 33.5 ± 2.5 | 4.0 ± 0.7 |

Example 9 eBCs Display Physiological Properties Similar to Human Islets In Vitro

Figure 20:
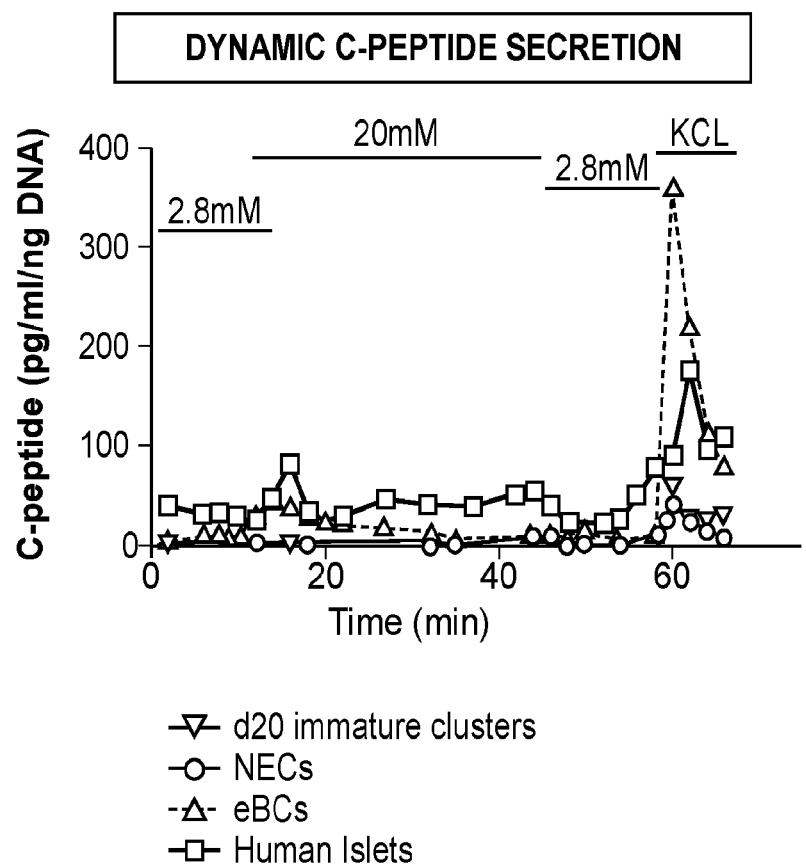
FIG. 20. eBCs exhibit functional characteristics similar to human islets in vitro. (A) Dynamic secretion of C-peptide in response to stimulation with 20 mM glucose and 30 mM KCl in an in vitro perifusion assay with a starting basal glucose concentration of 2.8 mM. eBCs (d26-27, green triangles), human islets (red squares), d20 immature clusters (black upside-down triangles) or Non-enriched clusters (NECs) (brown circles). (B) Cytosolic calcium signaling in response to alternating high (20 mM) and low (2.8 mM) glucose followed by KCl (30 mM) stimulation, as measured by Fura-2/AM fluorescence emission intensity. Plots are population measurements from individual whole clusters (not pre-selected single cells). From left to right, immature d20 clusters (black), eBCs (green) and human islets (red). (C) Calcium signaling and insulin secretion response of eBCs to tolbutamide, a sulfonylurea drug that blocks ATP-sensitive $K^+$ channels. (D) Dynamic mitochondrial energization as monitored by quenching of Rhodamine-123 fluorescence. The rate of fluorescence decay/quenching of Rhodamine-123 fluorescence is directly proportional to mitochondrial membrane potential. Representative experiments are shown throughout the figure. Dynamic secretion assay was repeated with five distinct hES-β-cell experiments and three human islet preparations. Calcium signaling and mitochondrial depolarization analyses were performed with three separate hES-β-cell differentiations.
Figure 20:
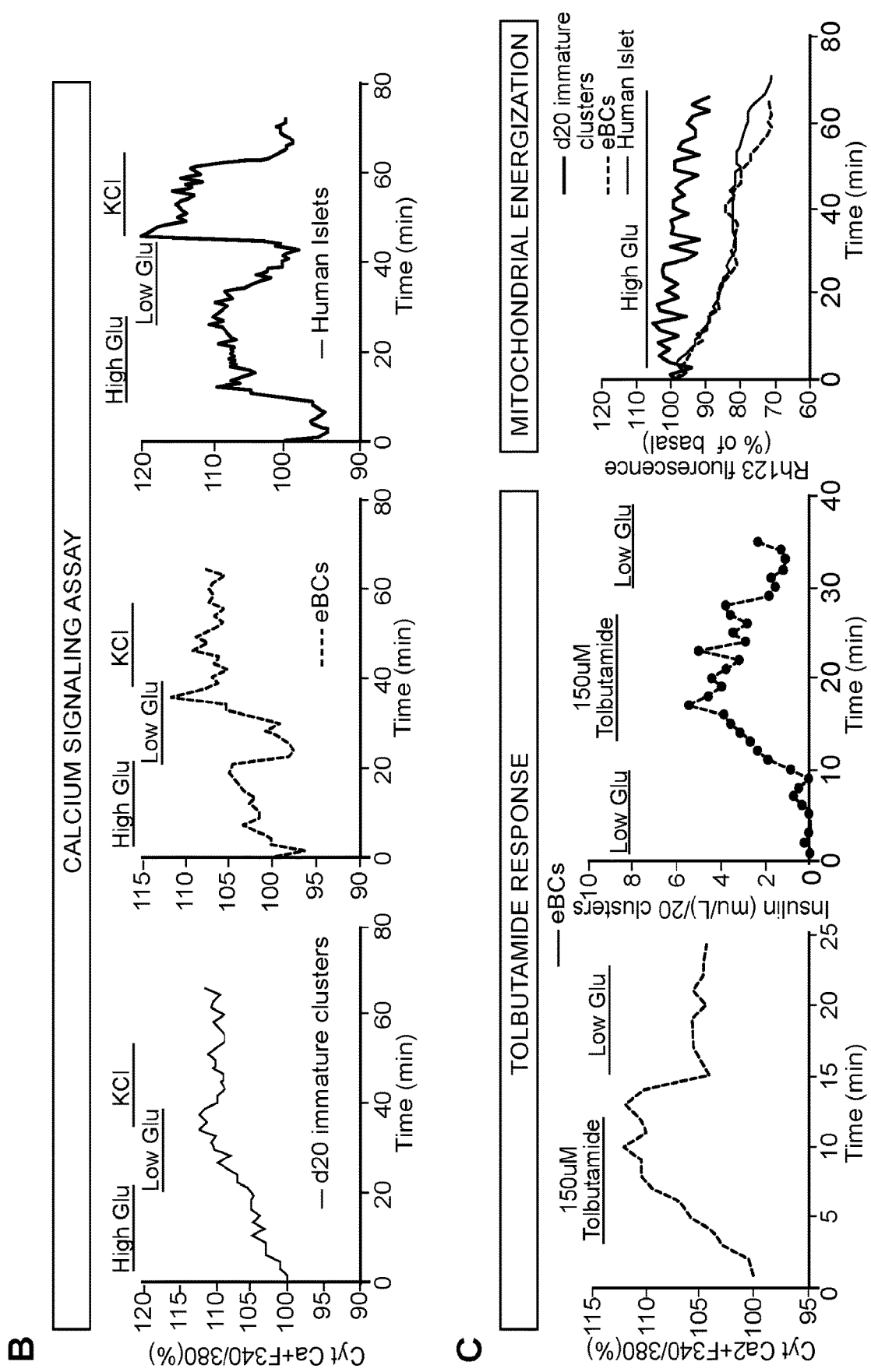

Current hPSC-derived-β-cells[2, 3, 25] are characterized by limited insulin secretion in response to glucose; especially they do not dynamically respond to glucose challenges in vitro, a trait indicative of an immature phenotype. To determine whether the observed increases in β-cell markers upon re-aggregation convey mature functional β-cell properties, we tested the dynamic response of d27 eBCs to alternating low and high glucose and KCL in a perifusion system. A rapid and marked first phase response was observed similar to human islets, albeit at slightly lower levels (FIG. 20A). To test whether this improved functional property is specific to eBCs, two types of un-enriched hPSC-derived-β-cell populations were also used: d20 clusters and d27 non-enriched clusters (NECs), which were re-aggregated in the same manner as eBCs but without GFP$^+$ sorting. As shown in FIG. 20A, both non-enriched hPSC-derived-β-cell populations responded to KCL but not to high glucose stimulation, demonstrating their immature nature.

Notably, the observed differences in function could not be ascribed to β-cell mass; d20 clusters are significantly larger in size (5000 to 8000 cells/cluster of which about 55% C-peptide$^+$), and hence contain 3.2-5.2 fold greater numbers of β-cells compared to eBCs (1000 cells/cluster of which about 85% are C-peptide$^+$).

Figure 27:
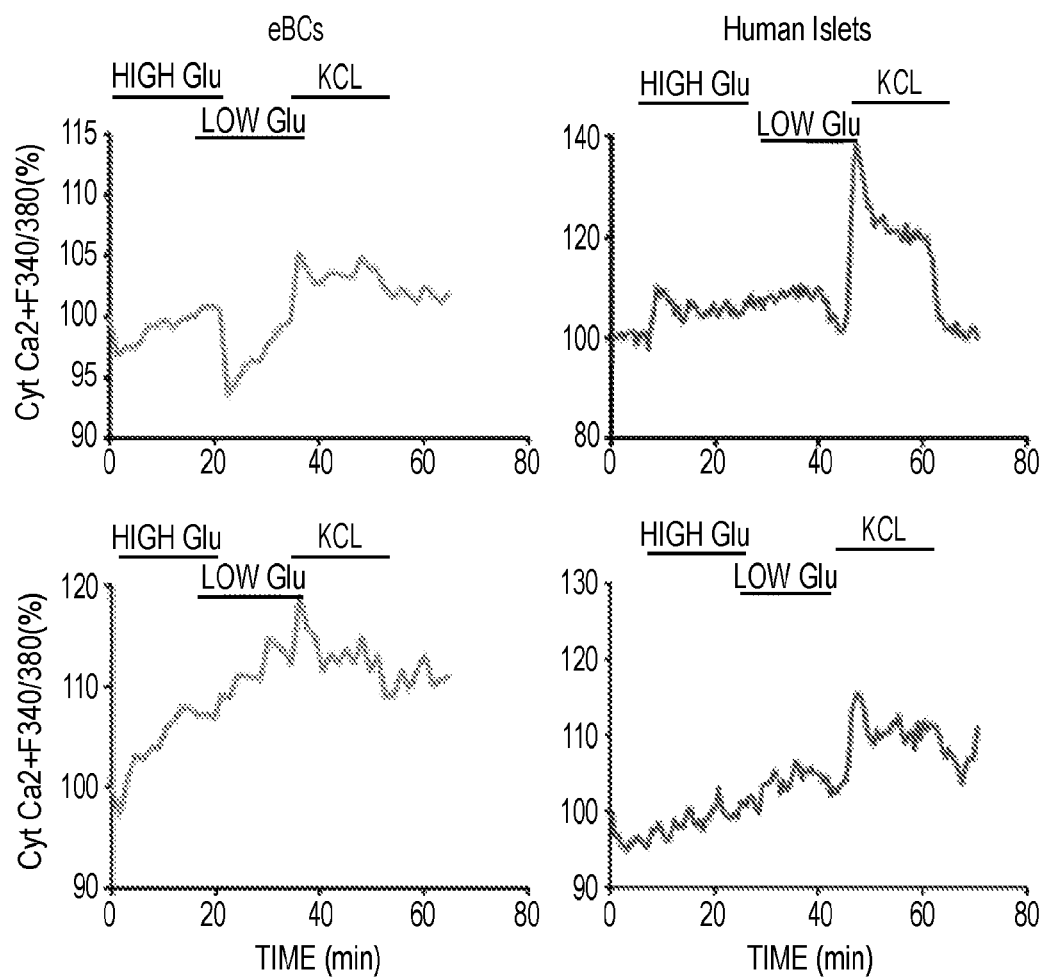
FIG. 27. Traces of calcium flux analysis in various batches of eBC and human islet preparations in response to glucose and KCl challenge. eBCs rapidly increased their cytosolic calcium ion concentrations in response to glucose. Bottom-right trace is representative of an islet preparation with mediocre function.

To further probe the functional properties of eBCs, we sought to investigate the cascade of events preceding insulin-secretion in a mature β-cell. Summarily, oxidation of glucose drives mitochondrial charging and ATP production, thus increasing the cellular phosphate potential (ATP/ADP ratio), which in turn causes closure of ATP-sensitive potassium (K-ATP) channels leading to depolarization of plasma membrane, and finally culminating in calcium influx and insulin secretion. First, we examined cytosolic calcium flux upon stimulation with glucose and KCL using Fura-2/AM in microfluidic chambers. d20 clusters, which contain progenitors and endocrine cells, displayed a slow rise in calcium flux upon stimulation with high glucose that did not terminate on reduction of glucose concentration to baseline (FIG. 20B, black-graph). This observation is consistent with that previously reported in β-like-cells by Rezania et al.[3]. In contrast, virtually all eBCs showed a significant and rapid increase in calcium influx upon stimulation with high glucose and depolarization with KCL. 20% of eBCs also returned to baseline calcium flux when glucose concentration was lowered and their profile looked identical to good preparations of human islets (FIG. 20B), indicating optimal activity of the voltage-dependent calcium channels. Notably, less optimal responses in calcium flux observed in some eBCs are also commonly observed in human islets (FIG. 27, lower-panel). Next, we assessed the robustness of the K-ATP channels; eBCs rapidly increased calcium flux and secreted insulin upon tolbutamide treatment, a sulfonylurea agent known to close K-ATP channels, and these processes returned to baseline upon termination of the stimulus (FIG. 20C). Finally, we interrogated mitochondrial energization, an upstream event that directly corresponds to ATP production, by measuring the quenching of Rhodamine$^{123}$ fluorescence on glucose and KCL stimulation in different populations. The rate of fluorescence decay is proportional to the membrane potential of mitochondria. Mitochondria of human islets and eBCs underwent quenching in an identical fashion, whereas mitochondria present in d20 clusters displayed mild quenching in an oscillatory pattern (FIG. 20D). This result suggests that the change in mitochondrial activity on glucose stimulation is higher in eBCs than d20 clusters, confirming their maturity. In summary, eBCs share many physiological properties, including dynamic insulin secretion, calcium signaling, sulfonylurea response, and mitochondrial energization with human islets, indicating their mature phenotype.

Example 10

Figure 21:
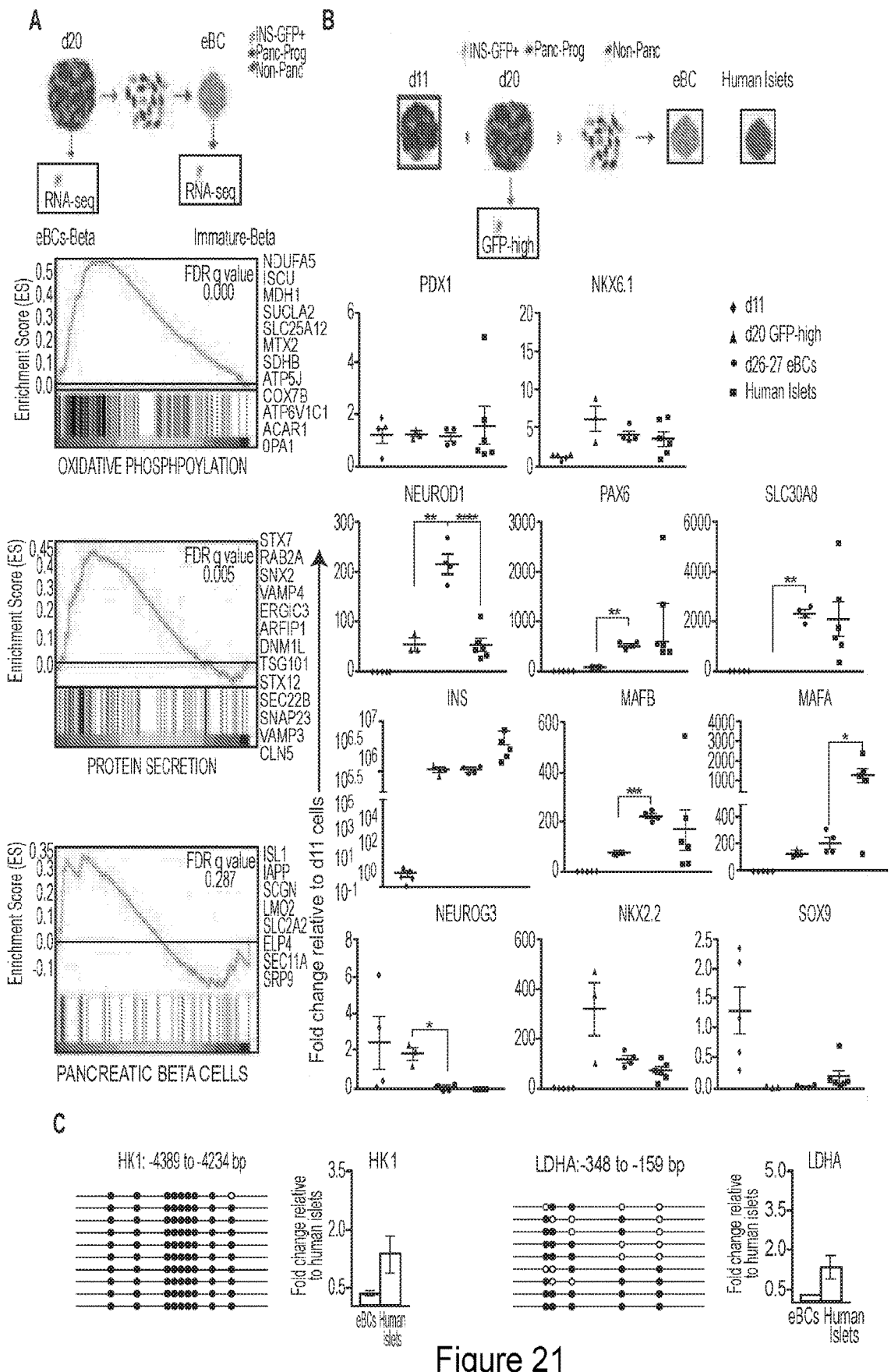
FIG. 21. β-cell function-related genes are expressed while disallowed genes are repressed in eBCs. (A) Schematic depicting isolation of $INS^{GFP-high+}$ cells from d20 clusters and eBCs for RNA-seq. Top relevant pathways enriched in eBCs by GSEA performed with Hallmark gene sets from MSigDB. Genes that are among the top hits in each pathway and enriched in the eBC β-cells are indicated on the right side of the respective trace. (B) Schematic depicting populations at different stages of differentiation used for qPCR analysis of key β-cell markers. d11: pancreatic progenitors (pre-endocrine induction) (blue diamond), d20 GFP-high: presort (black triangle), d26-27 eBCs (green circle) and human islets (red square). Data are expressed as fold-change relative to d11 cells, and error bars indicate SEM. n=3-6 biological replicates. *P<0.05, P<0.01, *P<0.001, ****P<0.0001 determined by two-tailed unpaired t-tests without Welch's correction, or with Welch's correction if SD was unequal. (C) Bisulfite sequencing analysis for the disallowed genes HK1 and LDHA at the indicated loci in eBCs. Each parallel line is an independent clone. Filled circles represent fully methylated and open circles represent hypomethylated CpGs. These regions are mostly methylated at both loci in eBCs. Gene expression of HK1 and LDHA in eBCs relative to human islets are shown on the right. n=4-6 biological replicates and error bars indicate SEM. P-values were not significant. Legend: INS–GFP+(GFP positive insulin-producing cells, green), Panc-Prog (Pancreatic progenitors, blue cells) and Non-Panc (Non-pancreatic cells, purple cells).
Figure 28:
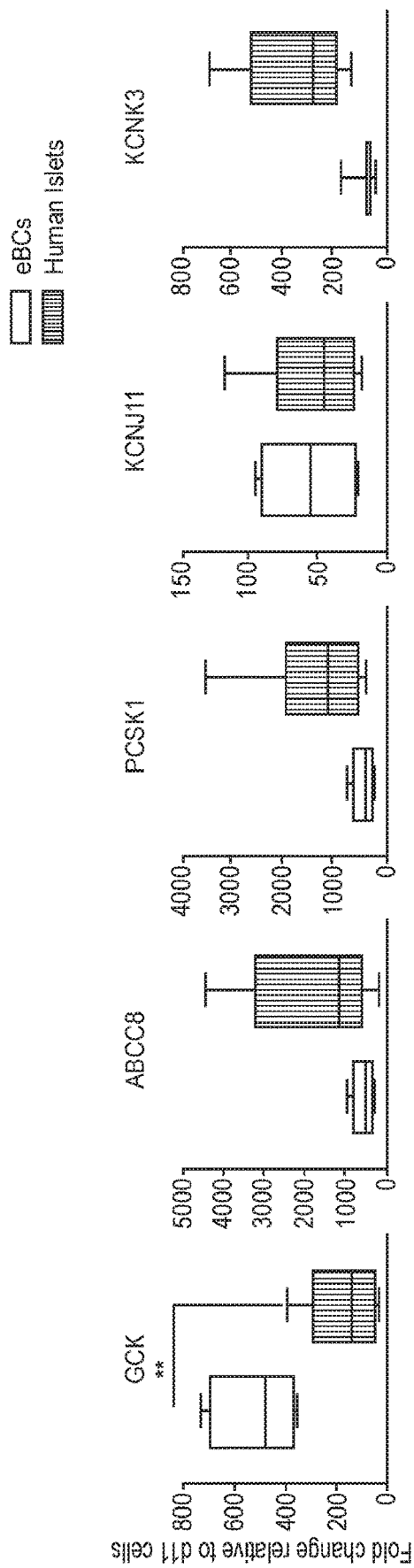
FIG. 28. eBCs and human islets express similar levels of genes encoding glucose-sensing and secretion-machinery factors. Data are expressed as fold-change relative to d11 cells. n=4-6 biological replicates. **P<0.01 determined by two-tailed unpaired t-tests without Welch's correction, or with Welch's correction if SD was unequal.

Transcriptome-Wide Analysis of eBCs Reveals Hallmarks of Function and Maturation The in vitro physiological analyses implied that clustering of β-cells confers exceptional functional properties. To further understand why eBCs display significantly better functional properties than d20 clusters that consist of a mix of progenitors and endocrine cells, a genome-wide transcriptome analysis was completed. INS$^{GFP\text{-}high+}$ cells were sorted from eBCs and d20 clusters by FACS, and total RNA sequencing (RNA-seq) was performed (FIG. 21A). Gene expression levels in immature d20 cells, d27NEC cells, eBC cells and beta cells from human pancreatic islets were determined using RNA-seq data and the expression levels of exemplary genes are presented in Table 6. Gene set enrichment analysis (GSEA) revealed that pathways significantly upregulated in eBCs include 'oxidative phosphorylation', 'pancreatic beta cells', and 'protein secretion' (FIG. 21A), all of which have been implicated in maturation in mice[6, 28,29]. The expression levels of key β-cell markers were further evaluated by qPCR (FIG. 21B). Expression of NEUROD1, PAX6, MAFB and SLC30A8, implicated in maturation and maintenance of β-cell identity and function[13, 14,16,30], were significantly higher in eBCs than INS$^{GFP\text{-}high+}$ cells of d20 clusters. In addition, expression of the endocrine progenitor marker NGN3 was lower in eBCs than in d20 INS$^{GFP\text{-}high+}$ cells, confirming the immature nature of d20 clusters. Importantly, compared to human islets, eBCs expressed similar levels of β-cell regulators (PDX1, NKX6.1, NKX2.2, PAX6 and MAFB), progenitor markers (NEUROG3 and SOX9), and insulin synthesis and secretion machinery (INS, SLC30A8, GCK, ABCC8, PCSK1, KCNJ11, and KCNK3) (FIG. 21B, FIG. 28). Of note, given the recent account that MAFA does not appear in human islets until puberty, it is not surprising that MAFA levels were lower in eBCs than adult human islets [11].

TABLE 5

| Genes | Taqman assay ids |
| --- | --- |
| PDX1 | Hs00426216_m1 |
| LDHA | Hs00855332_g1 |
| SLC30A8 | Hs00545183_m1 |
| MAFB | Hs00271378_s1 |
| KCNK1 | Hs00158428_m1 |
| KCNK3 | Hs00605529_m1 |
| PCSK1 | Hs01026107_m1 |
| KCNJ11 | Hs00265026_s1 |

TABLE 6

| | FPKM values | | | | |
| --- | --- | --- | --- | --- | --- |
| Gene name | D20 immature-Beta | D27 NEC-beta | D27 eBC-Beta | Human Adult Islet-Beta | |
| ATP6V0D2 | 0 | 0.0124323 | 0.0513565 | 0.536991 | Genes involved in OXPHOS |
| ATP5J | 32.3957 | 15.3792 | 75.0129 | 177.73 | |
| ATP5L | 89.6481 | 60.5105 | 199.082 | 366.38 | |
| ATP6V1D | 34.1963 | 24.4457 | 83.0309 | 139.125 | |
| ATP5O | 66.5281 | 51.8313 | 152.828 | 221.862 | |
| ATP5C1 | 103.5 | 90.7585 | 267.492 | 277.976 | |
| NDUFA5 | 16.6862 | 17.115 | 66.9206 | 84.4922 | |
| COX6C | 153.492 | 106.578 | 402.644 | 322.381 | |

TABLE 6-continued

| | FPKM values | | | | |
|---|---|---|---|---|---|
| Gene name | D20 immature-Beta | D27 NEC-beta | D27 eBC-Beta | Human Adult Islet-Beta | |
| SNAP23 | 3.80459 | 3.23178 | 10.4768 | 14.4522 | Genes involved in vesicular transport |
| VAMP4 | 5.12791 | 5.91566 | 23.3995 | 21.8029 | |
| SEC22B | 34.8315 | 43.5547 | 84.9389 | 163.532 | |
| STX7 | 7.54882 | 9.17629 | 20.4759 | 19.4536 | |
| NQO1 | 1.93235 | 6.05353 | 11.0637 | 21.3156 | Regulation of cellular amino acid metabolic process |
| CALM2 | 279.292 | 219.769 | 664.21 | 1085.96 | Positive regulation of DNA binding |
| TXN | 55.9843 | 37.6364 | 168.024 | 258.546 | |
| HMGB1 | 80.8789 | 67.5733 | 181.76 | 220.723 | |
| SLC8A2 | 2.51685 | 11.3662 | 7.75431 | 9.03834 | Calcium:Sodium antiporter activity |
| SLC8A3 | 0.316007 | 0.793365 | 1.58513 | 3.22293 | |
| MRPL13 | 21.2227 | 11.3279 | 48.6998 | 80.2054 | Mitochondrial translational elongation |
| GOLT1B | 13.1734 | 8.82642 | 39.4514 | 40.6625 | Golgi mediated transport |

Emerging evidence indicates that β-cell maturation not only requires the cellular machinery enabling insulin synthesis and stimulus-secretion coupling, but also the reduction of disallowed genes that interfere with glucose sensing. DNA methylation has been recently implicated in repression [9], and hence we analyzed CpG-rich regions within loci of critical glucose-secretion decoupling genes: HK1 and LDHA. Bisulfite sequencing of differentially methylated regions of HK1 and LDHA in eBCs showed hypermethylation akin to the pattern observed in human islets[9] (FIG. 21C). To confirm repression, we analyzed the transcript levels of these genes by qPCR; as expected, their expression was lower in eBCs compared with human islets that contain a higher proportion of non-beta cell types. These findings indicate that the metabolic switch from anaerobic to aerobic glycolysis reported during β-cell maturation is complete in eBCs.

Figure 22:
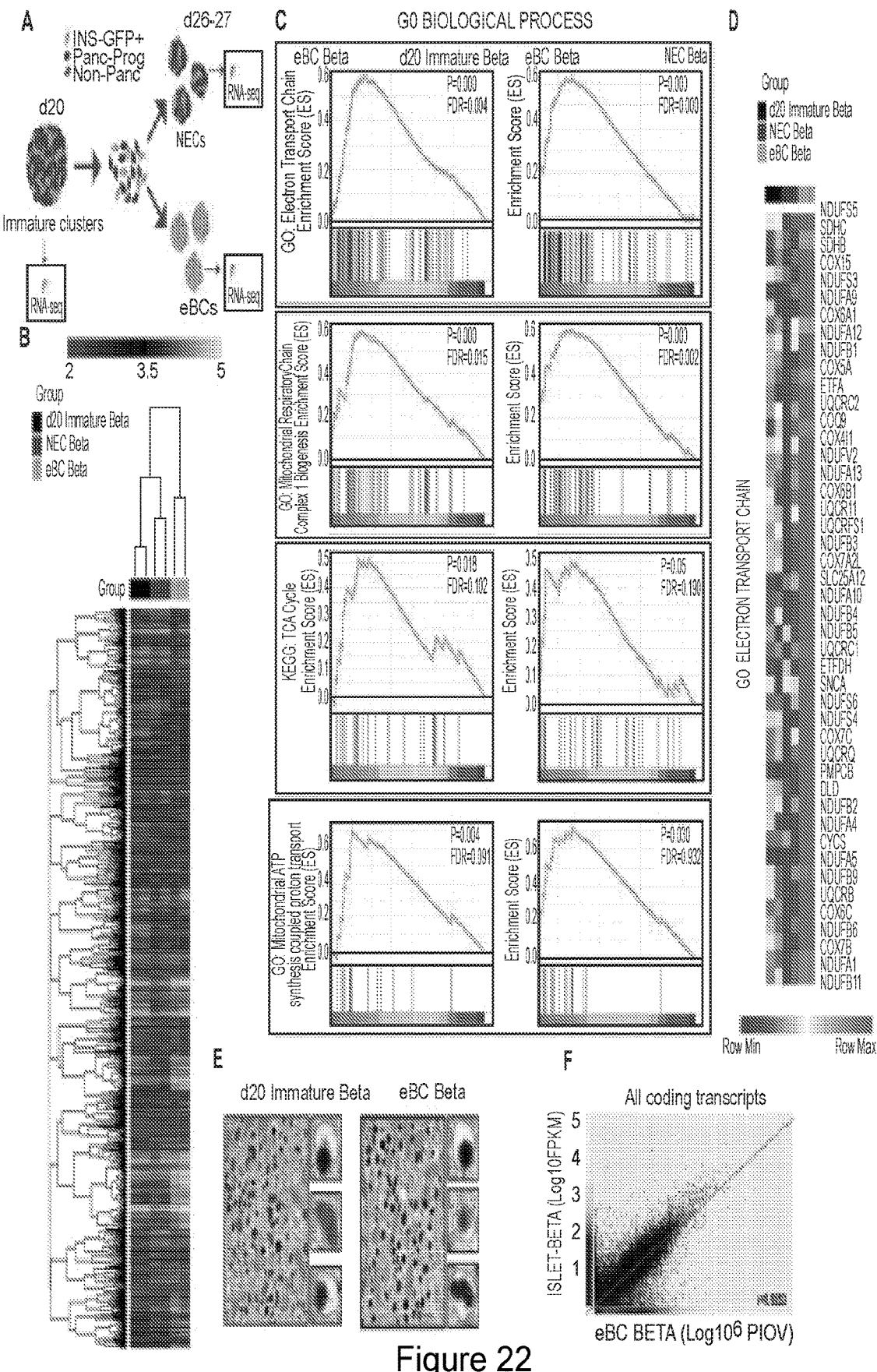
FIG. 22. β-cells in highly enriched endocrine-niche eBCs are distinct from immature β-cells in a progenitor-rich niche. (A) Schematic depicting the isolation of $INS^{GFP-high+}$ cells via FACS from d20 immature clusters, d26-27 NECs, and d26-27 eBCs for RNA-seq. Legend: INS–GFP+(GFP positive insulin-producing cells, green), Panc-Prog (Pancreatic progenitors, blue cells) and Non-Panc (Non-pancreatic cells, purple cells). (B) Heatmap of differentially expressed genes between the three types of β-cells. Hierarchical clustering indicates that d20 immature β-cells (black) and NEC β-cells (blue) are more closely related than β-cells from eBCs (green). (C) GSEA of the three types of β-cells with gene sets from MSigDB-biological process ontology revealed various sub-processes of oxidative phosphorylation (OXPHOS) to be highly enriched in β-cells isolated from eBCs compared to β-cells of d20 clusters or NECs. (D) Heat map of FPKM (Fragments Per Kilobase of transcript per Million mapped reads) values for the top hits in electron transport chain ontogeny. In RNA-Seq, the relative expression of a transcript is proportional to the number of cDNA fragments that originate from it. FPKM is calculated by counting fragments, not reads. Sample FPKM values were normalized across every gene. (E) Transmission electron micrograph of β-cells present in d20 immature clusters and β-cells found in d27 eBCs. Higher magnification images in the panels on the right show representative types of individual granules present in the samples. Scale bar, 1 μm. (F) Scatter plot of $log_{10}$FPKM values for all coding transcripts present in β-cells of eBCs and β-cells isolated from adult human islets. Pearson correlation coefficient=0.9253, p-value $<2.2\times10^{-16}$.
Figure 30:
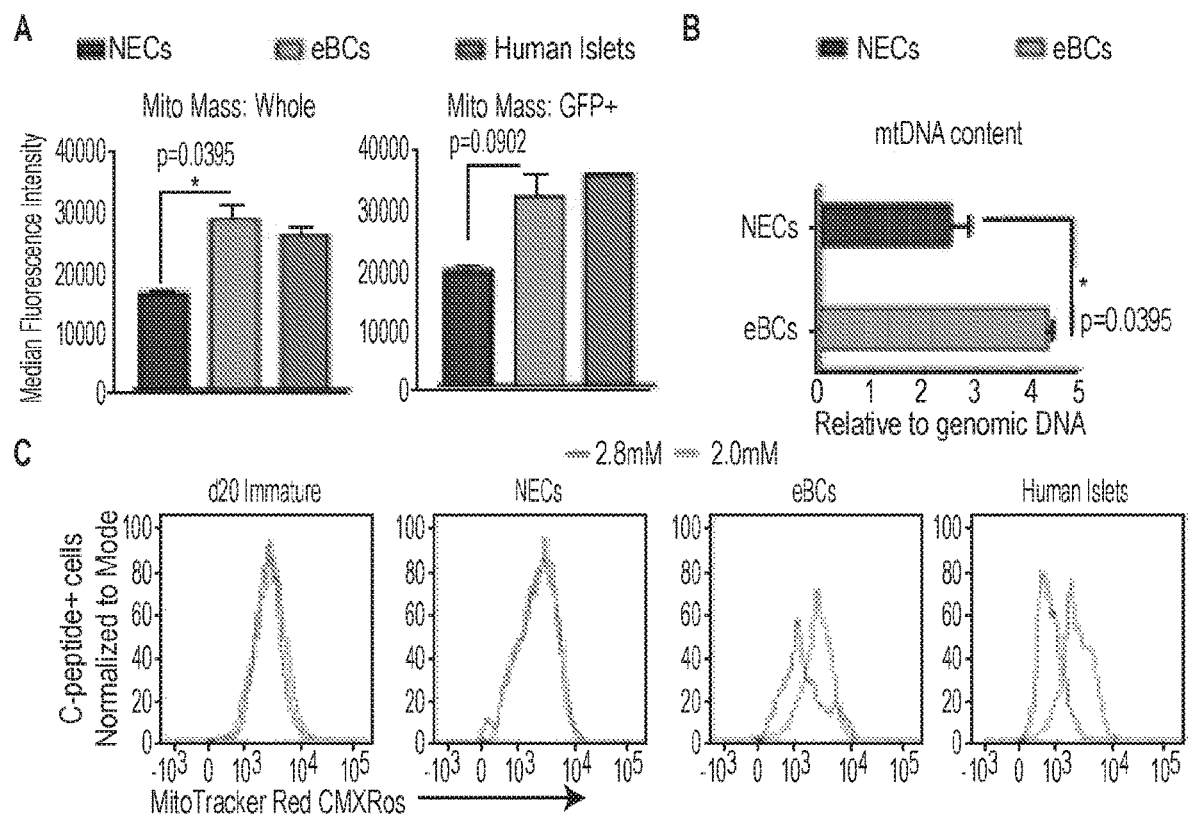
FIG. 30. eBCs contain higher numbers of active mitochondria. (A) Quantification of flow cytometric staining with MitoID, a dye used for the detection of mitochondrial mass. n=2 biological replicates. Data are presented as median fluorescence intensity±SEM. *P<0.05 determined by two-tailed unpaired t-test. P-values not significant between eBCs and islets. (B) Mitochondrial DNA (mtDNA) content assessed by the ratio of mtDNA/nuclear DNA by qPCR for the mitochondrial 16S rRNA gene and the nuclear β2 microglobulin gene. n=3 biological replicates. Data are presented as mean±SEM. *P<0.05 determined by two-tailed unpaired t-test. (C) FACS analyses of the indicated populations after incubation with 2.8 mM glucose or 20 mM glucose and stained with the mitochondrial membrane potential indicator dye MitoTracker Red CMXRos.

Example 11

β-Cells Residing in a Highly Enriched Endocrine-Niche are Distinct from β-Cells in a Progenitor-Rich Niche The data indicate that eBCs, as a population, are more mature than immature (d20) clusters. To dissect the changes in the state of INS⁻ GFP⁺ cells caused by coalescence, RNA-seq was conducted on GFP-high cells isolated from cell aggregates at these various stages (FIG. 22A). Heat map and hierarchical clustering of the three types of β-cell population shows that β-cells from d20 clusters and d27 NECs cluster together and are distinct from β-cells found in d27 eBCs (FIG. 22B). Indeed, 1321 genes were differentially expressed in β-cells from d27 eBCs and d20 immature clusters, and 920 genes were differentially expressed in β-cells from d27 eBCs and d27 NECs. GSEA pathways significantly upregulated in β-cells of eBCs compared with β-cells of both d20 immature and d27 NECs were sub-processes of oxidative phosphorylation (OXPHOS), including 'electron transport chain', 'mitochondrial respiratory complex 1 biogenesis', 'TCA cycle' and 'mitochondrial ATP synthesis coupled proton transport' (FIG. 22C). A heat map of ETC genes enriched in eBC-β-cells is shown in FIG. 22D. Graphical mapping of these genes illustrates that multiple steps of OXPHOS involving all the electron transport chain complexes (I, II, III, IV and V) are enhanced in β-cells of eBCs (FIG. 30). Another staple of β-cell maturity is the presence of well-defined insulin granules. The majority of β-cells within eBCs show the typical electron dense core and electron light halo (FIG. 22E). Finally, we compared the transcriptome of β-cells of eBCs to β-cells isolated from adult human islets using antibodies reported by Dorell et al.[29]. A scatter plot of all coding genes shows a high degree of correlation between the two types of β-cells (Pearson correlation co-efficient=0.9253 and p-value <2.2e-16) (FIG. 22F), illuminating that β-cells of eBCs are equivalent to islet β-cells. Thus, by multiple criteria re-aggregation of immature INS⁻GFP⁺ cells followed by extended culture results in mature and functional β-cells.

Example 12

β-Cell Clustering Induces Metabolic Maturation of Mitochondria

Figure 23:
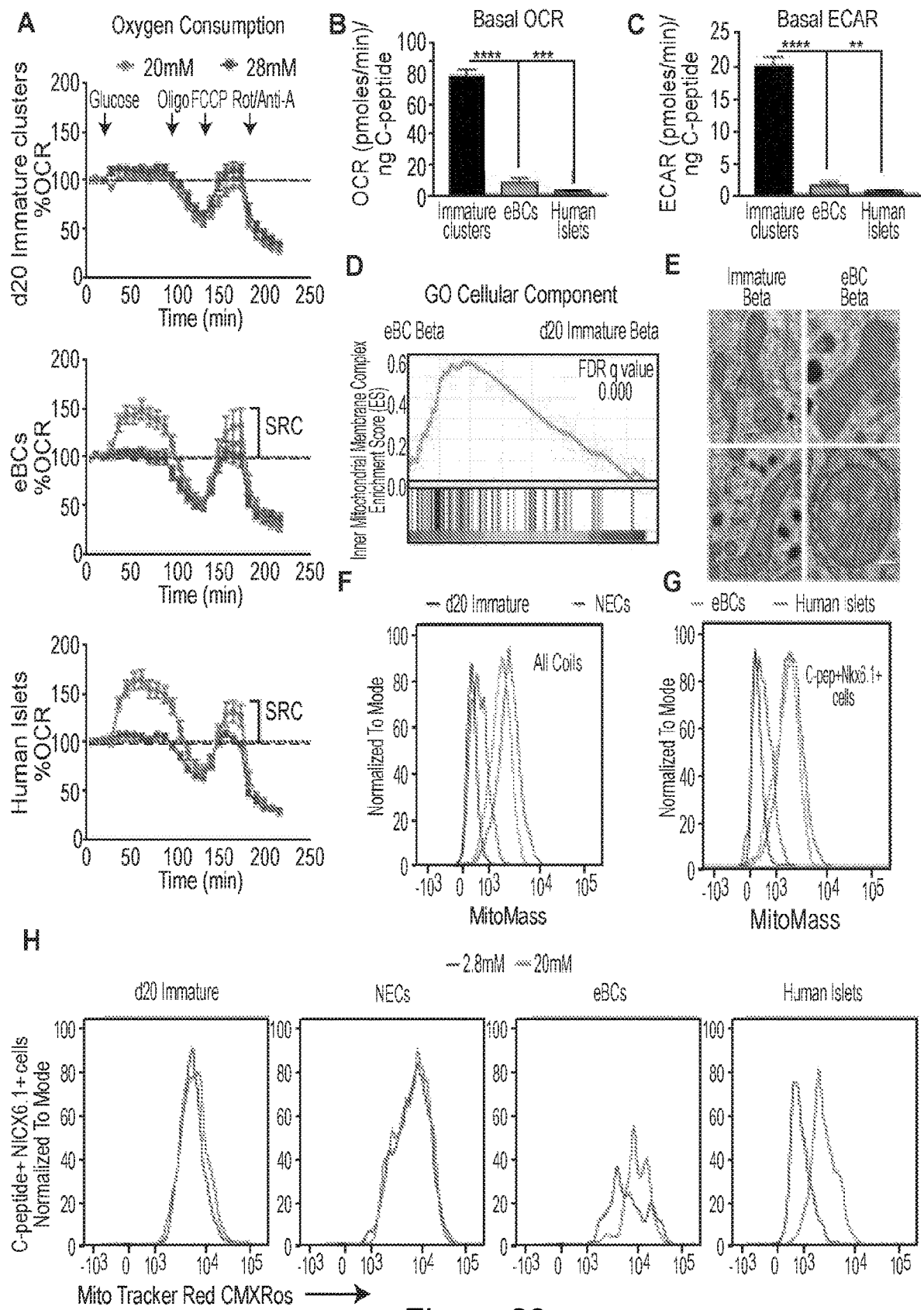
FIG. 23. eBCs possess functionally and structurally mature mitochondria. Mitochondrial respiration assessed by a Cell Mito Stress Test using a Seahorse XFe24 Bioanalyzer. (A) Oxygen consumption rate (OCR) was first measured under basal conditions (2.8 mM glucose) followed by sequential addition of either 2.8 mM (blue line) or 20 mM glucose (red line), 5 μM Oligomycin (Oligo), 1 μm FCCP, and 5 μm Rotenone+Antimycin A (Rot/Anti-M). eBCs showed similar OCR profile as human islets, while d20 immature clusters do not increase their OCR on glucose stimulation. n=5-7 biological replicates. Data are expressed as mean±SEM. (B) Basal OCR and (C) Basal ECAR (extracellular acidification rate) of immature clusters (black bar), eBCs (green bar) and human islets (red bar). n=5-13 biological replicates. Data are expressed as mean±SEM. P<0.01, *P<0.001, ****P<0.0001 determined by two-tailed unpaired t-tests without Welch's correction, or with Welch's correction if SD was unequal. (D) GSEA trace demonstrates enrichment of inner mitochondrial membrane complex signature in the cellular component ontology gene sets in eBCs compared to immature clusters. (E) Two representative transmission electron micrographs of mitochondria in β-cells in d20 immature clusters and eBCs. The mitochondrial cristae are denser and more tightly folded in eBCs. Scale bar, 250 nm. (F, G). Flow cytometry with MitoID was used to assess mitochondrial mass in the indicated populations. The experiment was repeated with three independent differentiations. (F) Flow histogram of whole populations stained with MitoID. (G) Flow histogram of C-pep$^+$/NKX6.1$^+$ cells within each population stained with MitoID. (H) Flow cytometry analyses of the indicated populations after incubation with 2.8 mM glucose or 20 mM glucose and stained with the mitochondrial membrane potential indicator dye MitoTracker Red CMXRos.

RNA-seq results implicate activation of OXPHOS, electron transport chain and ATP production as potentially essential steps for maturation of eBCs. In order to assess mitochondrial respiratory function at a phenotypic level, we performed the Cell Mito stress test using a Seahorse XFe24 analyzer. eBCs (FIG. 23A, center) and human islets (FIG. 23A, bottom) clearly increased their OCR upon stimulation with high glucose in an identical manner whereas d20 immature clusters (FIG. 23A, top) did not display a glucose-induced rise in OCR. Interestingly, the immature clusters had almost no spare respiratory capacity (SRC), indicating that they are respiring at their limit, a finding also substantiated by the significantly higher basal OCR (normalized to ng C-peptide to account for β-cells only) of immature clusters (FIG. 23B). Additionally, immature clusters also presented with significantly higher basal ECAR than eBCs and human islets (FIG. 23C). The capacity of immature hPSC-derived-β-like cells to raise ECAR, but not OCR, in response to glucose supports the notion that they rely on glycolysis and not mitochondrial oxidative phosphorylation for glucose oxidation, a phenomenon previously described for immature rodent β-cells[9, 17, 30]. In stark contrast, hPSC-derived eBCs are metabolically mature as they utilize mitochondrial respiration compulsory for maximal glucose stimulated insulin secretion as efficiently as human islets.

Figure 31:
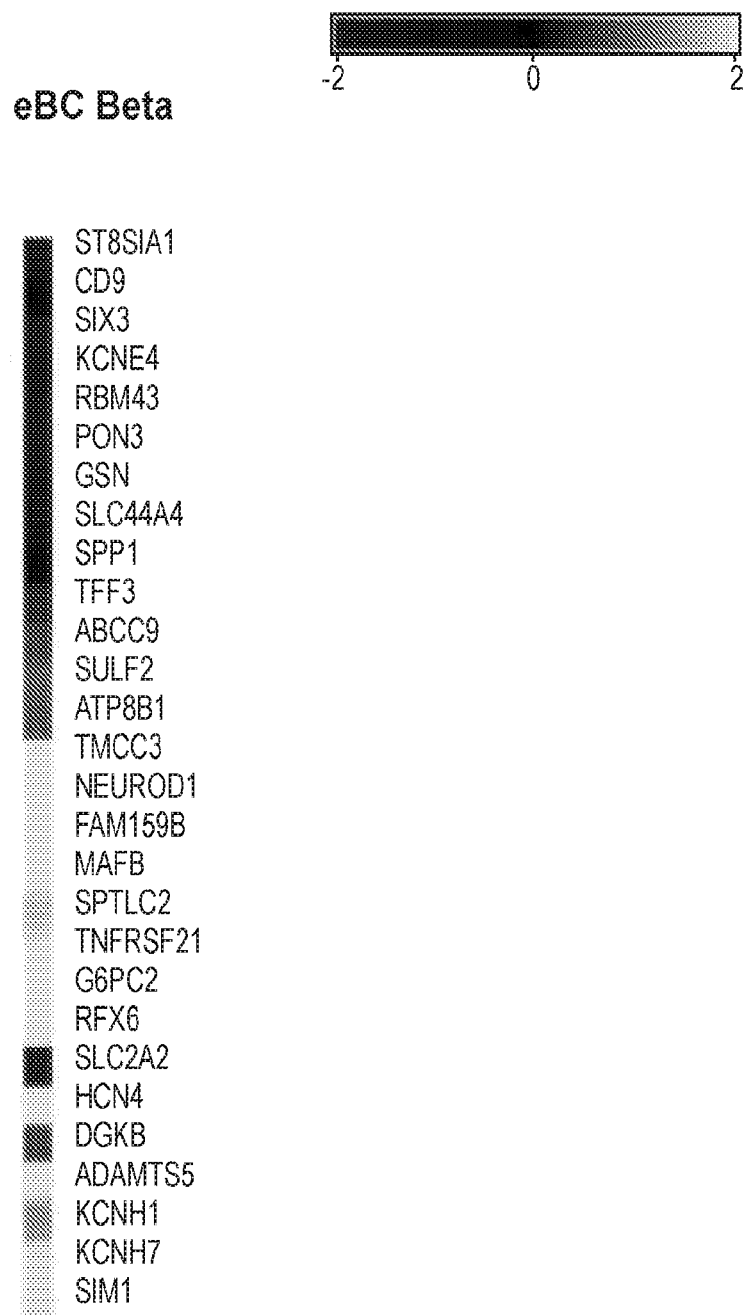
FIG. 31. Beta cells in eBCs closely resemble the Beta-1 subtype of beta cells present in adult human islets. Heat map of expression levels of genes that demarcate the Beta-1 subtype in eBCs. Note the low expression levels of CD9 and ST8SIA1.

As expected, GSEA also indicated enrichment of the components of the 'inner mitochondrial membrane complexes', the location of OXPHOS, in β-cells upon re-aggregation/clustering (FIG. 23D). On examining the ultrastructure of mitochondria in β-cells of eBCs, we observed highly folded (narrow gap between the two surfaces of the inner membrane) and stacked cristae (FIG. 23E) that indicate properly organized OXPHOS supercomplexes necessary for efficient electron transport and ATP generation[31]. In comparison, immature β-like-cells (d20) carry mitochondria that appear less organized (FIG. 23E). Notably, ERRγ, a mitochondrial regulator recently reported to induce metabolic maturation[17], was expressed at significantly higher levels in β-cells of eBCs (RNA-seq fold-change=2.25, p=0.02) than β-cells situated in progenitor-rich niche (d20 immature clusters/d27 NECs). Next, we investigated whether the enhanced mitochondrial function and ultrastructure also correlated with increased mitochondrial mass. At the whole population level, eBCs and human islets had similar mitochondrial mass, higher than both d20 immature and d27 NECs (FIGS. 26F and 34A). Likewise, analysis of only C-peptide$^+$ NKX6.1$^+$ cells, the presumable β-cells in each population, revealed that β-cells in eBCs and human islets had equivalent mitochondrial mass (FIG. 23G). Additionally, measurement of mtDNA content illuminated that mitochondrial numbers were also higher in eBCs (FIG. 31B). To directly assess mitochondrial function, we measured the membrane potential of mitochondria upon glucose stimulation. Mitochondria in C-peptide$^+$ and C-peptide$^+$ NKX6.1$^+$ cells in eBCs and human islets are differentially charged in low and high glucose, a phenotype absent from cells in d20 immature or d27 NECs (FIGS. 23H and 31C). Collectively, these findings indicate that re-aggregation of β-like-cells induces mitochondrial biogenesis and promotes mitochondrial oxidative metabolism.

Example 13 eBCs Rapidly Function In Vivo

Figure 24:
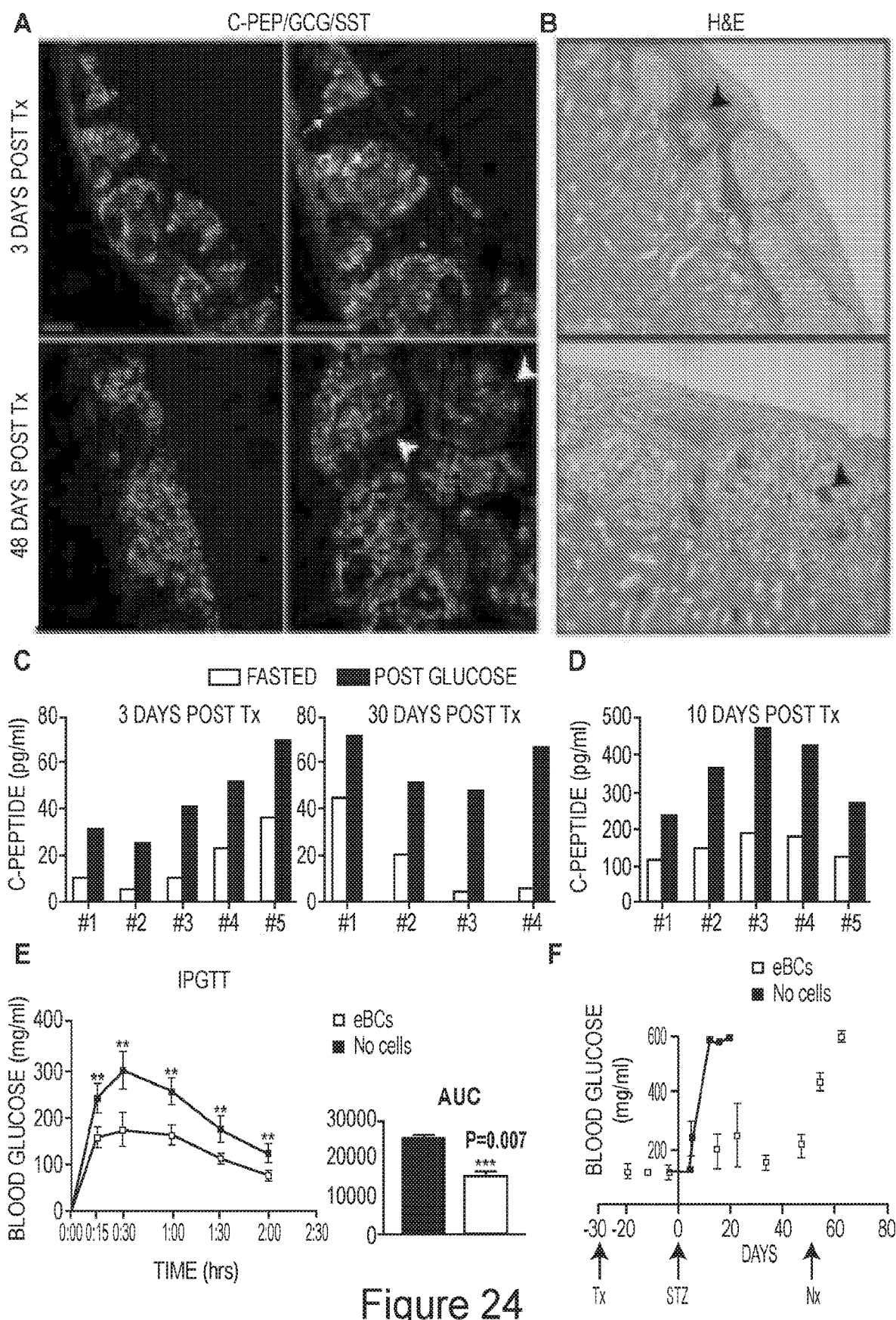
FIG. 24. eBCs are functional in vivo as early as 3 days after transplant. (A-C) 700 eBCs (about 0.7×10$^6$ cells) were transplanted under the kidney capsule of non-diabetic male NSG mice. (A) Grafts removed 3 days post-transplant (upper panel) or 48 days post-transplant (lower panel) were stained for C-peptide (C-PEP), glucagon (GCG) and somatostatin (SST). White arrows indicate GCG$^+$/C-PEP$^+$ double-positive cells. White arrowheads mark monohormonal GCG$^+$ or SST$^+$ cells. Scale bar, 100 μm. (B) H&E (hematoxylin and eosin) images at the corresponding time points indicated in (A). Scale bar, 100 μm. Black arrowheads indicate endothelial islands. (C) In vivo glucose challenge test at indicated days after transplant. Human C-peptide levels in the serum were measured after an overnight fast (grey bar) and again 30 minutes after an IP glucose injection (black bar). The numbers on the X axes indicate individual animals. ND: not detected. (D) 4000 eBCs (about 4×10$^6$ cells) were transplanted under the kidney capsule of non-diabetic male NSG mice. Human C-peptide levels following fasting (grey bar) and 60 minutes after an IP glucose bolus (black bar) were measured 10 days after transplant. The numbers on the X axes indicate individual animals. (E) Intra-Peritoneal Glucose Tolerance Test (IPGTT) was performed on NSG mice 30 days after transplantation with 700 eBCs (green, n=4) and control non-transplanted NSG mice (no cells) (black, n=5). P<0.01, **P<0.0001 determined by two-tailed unpaired t-tests. (F) Random fed glucose measurements taken from STZ-treated control NSG mice (no cells, black line, n=2) or NSG mice transplanted with 700 eBCs (green line, n=2). Mice that did not receive eBC grafts died 22 days after STZ treatment.

A distinctive feature of human islets and mature β-cells is their ability to function in vivo within days after transplantation. Yet, published protocols have reported positive responses to in vivo glucose challenges only 2-6 weeks after transplantation of their in vitro hPSC-derived-β-cells[2, 3, 25]. To test the functionality of our cells in vivo, we transplanted 700 eBCs (about 700,000 cells) of which about 80% are C-peptide$^+$ NKX6.1$^+$ (about 560,000 β-cells) into non-diabetic NSG mice. eBCs secreted more C-peptide after an acute glucose challenge as early as 3 days post-transplant (7/8 animals) and maintained their function even 30-days after transplant (FIG. 24C). Similar results were obtained when we transplanted a higher number of cells, 4×10$^6$ cells or 4000 eBCs, into non-diabetic NSG mice (FIG. 24D). Immunofluorescent staining of the transplanted kidney recovered 3 days following the transplant showed that majority of the graft consisted of C-peptide$^+$ cells with occasional co-positive C-peptide$^+$ Glucagon$^+$ or C-peptide$^+$ Somatostatin$^+$ cells (FIG. 24A, top-panel). The corresponding H&E image (FIG. 24B, top-panel) illustrates intact islet-like endocrine clusters, which are characterized by pale cytoplasm, infiltrated with endothelial islands (black-arrowhead). Upon examining the graft at day 48 we clearly observed clusters composed of monohormonal C-peptide$^+$, Glucagon$^+$ and Somatostatin$^+$ endocrine cells organized in a manner analogous to human islets. Though the majority of the cells in the graft were C-peptide$^+$, we found a significant number of Glucagon$^+$ and few Somatostatin$^+$ cells (FIG. 24A, bottom panel). H&E analysis at this stage revealed more extensive network of endothelial islands meandering through the grafts (FIG. 24B, bottom-panel). Next, we performed a glucose tolerance test on mice transplanted with 700 eBCs and control mice that did not receive any cells 30 days after transplant. eBC-transplanted mice were significantly more glucose-tolerant and cleared glucose more rapidly than control mice (FIG. 24E; note reduced area under curve (i.e., AUC) in transplanted mice; p=0.007). Finally, we tested whether eBCs were resistant to STZ-induced diabetes. eBC-transplanted mice, which had C-peptide levels post-glucose stimulation greater than 60 pg/ml, did not develop overt hyperglycemia for 50 days while untransplanted mice exhibited blood glucose levels greater than 600 mg/dl and died 22 days after STZ treatment. Importantly, mice transplanted with eBCs turned hyperglycemic on removal of engrafted kidney, demonstrating that normoglycemia was maintained by hPSC-derived-β-cells (FIG. 24F). Of note, mice that had circulating C-peptide less than 60 pg/ml post-glucose challenge with fewer numbers of engrafted β-cells were unable to be protected from diabetes. Summarily, these data indicate that eBCs are immediately functional upon transplantation and capable of preventing hyperglycemia upon destruction of endogenous β-cells.

REFERENCES FOR EXAMPLES 8-13

1. Barton, F. B., et al., Improvement in Outcomes of Clinical Islet Transplantation: 1999-2010. Diabetes Care, 2012. 35(7): p. 1436-1445.
2. Pagliuca, Felicia W., et al., Generation of Functional Human Pancreatic P Cells In Vitro. Cell, 2014. 159(2): p. 428-439.
3. Rezania, A., et al., Reversal of diabetes with insulin-producing cells derived in vitro from human pluripotent stem cells. Nat Biotech, 2014. 32(11): p. 1121-1133.
4. Russ, H. A., et al., Controlled induction of human pancreatic progenitors produces functional beta-like cells in vitro. The EMBO Journal, 2015: p. n/an/a.
5. Zhu, S., et al., Human pancreatic beta-like cells converted from fibroblasts. Nature Communications, 2016. 7: p. 10080.
6. Blum, B., et al., Functional beta-cell maturation is marked by an increased glucose threshold and by expression of urocortin 3. Nat Biotech, 2012. 30(3): p. 261-264.
7. Aguayo-Mazzucato, C., et al., Mafa expression enhances glucose-responsive insulin secretion in neonatal rat beta cells. Diabetologia, 2011. 54(3): p. 583-593.
8. Jermendy, A., et al., Rat neonatal beta cells lack the specialised metabolic phenotype of mature beta cells. Diabetologia, 2011. 54(3): p. 594-604.
9. Dhawan, S., et al., DNA methylation directs functional maturation of pancreatic β cells. The Journal of Clinical Investigation. 125(7): p. 2851-2860.
10. Arda, H. E., et al., Age-Dependent Pancreatic Gene Regulation Reveals Mechanisms Governing Human 3 Cell Function. Cell Metabolism, 2016. 23(5): p. 909-920.
11. Formation of a Human β-Cell Population within Pancreatic Islets Is Set Early in Life. The Journal of Clinical Endocrinology & Metabolism, 2012. 97(9): p. 3197-3206.
12. Gu, C., et al., Pancreatic β Cells Require NeuroD to Achieve and Maintain Functional Maturity. Cell Metabolism, 2010. 11(4): p. 298-310.

13. Gosmain, Y., et al., Pax6 Is Crucial for β-Cell Function, Insulin Biosynthesis, and Glucose-Induced Insulin Secretion. Molecular Endocrinology, 2012. 26(4): p. 696-709.
14. Dai, C., et al., Islet-enriched gene expression and glucose-induced insulin secretion in human and mouse islets. Diabetologia, 2012. 55(3): p. 707-718.
15. Scoville, D. W., et al., MLL3 and MLL4 Methyltransferases Bind to the MAFA and MAFB Transcription Factors to Regulate Islet β-Cell Function. Diabetes, 2015. 64(11): p. 3772-3783.
16. Lemaire, K., L. Thorrez, and F. Schuit, Disallowed and Allowed Gene Expression: Two Faces of Mature Islet Beta Cells. Annual Review of Nutrition, 2016. 36(1): p. 45-71.
17. Yoshihara, E., et al., ERRγ Is Required for the Metabolic Maturation of Therapeutically Functional Glucose-Responsive β Cells. Cell Metabolism. 23(4): p. 622-634.
18. Hawdon, J. M., et al., The role of pancreatic insulin secretion in neonatal glucoregulation. I. Healthy term and preterm infants. Archives of Disease in Childhood, 1993. 68(3 Spec No): p. 274-279.
19. Kaye, R., et al., The response of blood glucose, ketones, and plasma nonesterified fatty acids to fasting and epinephrine injection in infants and children. The Journal of Pediatrics, 1961. 59(6): p. 836-847.
20. Henquin, J.-C. and M. Nenquin, Dynamics and Regulation of Insulin Secretion in Pancreatic Islets from Normal Young Children. PLoS ONE, 2016. 11(11): p. e0165961.
21. Nair, G. and M. Hebrok, Islet formation in mice and men: lessons for the generation of functional insulin-producing β-cells from human pluripotent stem cells. Current Opinion in Genetics & Development, 2015. 32(0): p. 171-180.
22. Jeon, J., et al., Endocrine cell clustering during human pancreas development. J Histochem Cytochem, 2009. 57: p. 811-824.
23. Rahier, J., J. Wallon, and J. C. Henquin, Cell populations in the endocrine pancreas of human neonates and infants. Diabetologia, 1981. 20(5): p. 540-546.
24. Borden, P., et al., Sympathetic Innervation during Development Is Necessary for Pancreatic Islet Architecture and Functional Maturation. Cell Reports, 2013. 4(2): p. 287-301.
25. Russ, H. A., et al., Controlled induction of pancreatic endocrine progenitors from human embryonic stem cells enables formation of glucose responsive beta like cells in vitro. EMBO, 2015.
26. Pisania, A., et al., Quantitative analysis of cell composition and purity of human pancreatic islet preparations. Lab Invest, 2010. 90(11): p. 1661-1675.
27. Taylor, Brandon L., F.-F. Liu, and M. Sander, Nkx6.1 Is Essential for Maintaining the Functional State of Pancreatic Beta Cells. Cell Reports. 4(6): p. 1262-1275.
28. Ediger, B. N., et al., Islet-1 Is Essential for Pancreatic β-Cell Function. Diabetes, 2014. 63(12): p. 4206-4217.
29. Dorrell, C., et al., Transcriptomes of the major human pancreatic cell types. Diabetologia, 2011. 54(11): p. 2832.
30. Jacovetti, C., et al., Postnatal β-cell maturation is associated with islet-specific microRNA changes induced by nutrient shifts at weaning. Nature Communications, 2015. 6: p. 8084.
31. Cogliati, S., J. A. Enriquez, and L. Scorrano, Mitochondrial Cristae: Where Beauty Meets Functionality. Trends in Biochemical Sciences. 41(3): p. 261-273.
32. Hellerstrim, C. and I. Swenne, Functional Maturation and Proliferation of Fetal Pancreatic β-Cells. Diabetes, 1991. 40(Supplement 2): p. 89-93.
33. Lehmann, R., et al., Superiority of Small Islets in Human Islet Transplantation. Diabetes, 2007. 56(3): p. 594-603.
34. Rutter, Guy A., et al., Pancreatic β-cell identity, glucose sensing and the control of insulin secretion. Biochemical Journal, 2015. 466(2): p. 203-218.
35. Wijesekara, N., et al., Beta cell-specific Znt8 deletion in mice causes marked defects in insulin processing, crystallisation and secretion. Diabetologia, 2010. 53(8): p. 1656-1668.
36. Parnaud, G., et al., Cadherin Engagement Protects Human β-Cells from Apoptosis. Endocrinology, 2011. 152(12): p. 4601-4609.
37. Konstantinova, I., et al., EphA-Ephrin-A-Mediated β Cell Communication Regulates Insulin Secretion from Pancreatic Islets. Cell. 129(2): p. 359-370.
38. Wojtusciszyn, A., et al., Insulin secretion from human beta cells is heterogeneous and dependent on cell-to-cell contacts. Diabetologia, 2008. 51(10): p. 1843-1852.
39. Stolovich-Rain, M., et al., Weaning Triggers a Maturation Step of Pancreatic β Cells. Developmental Cell. 32(5): p. 535-545.
40. Dorrell, C., et al., Human islets contain four distinct subtypes of β cells. Nature Communications, 2016. 7: p. 11756.
41. Bader, E., et al., Identification of proliferative and mature β-cells in the islets of Langerhans. Nature, 2016. 535(7612): p. 430-434.

Each of the references listed below and cited throughout the disclosure is incorporated by reference herein in its entirety, or in relevant part, as would be apparent from context. The disclosed subject matter has been described with reference to various specific embodiments and techniques. It should be understood, however, that many variations and modifications may be made while remaining within the spirit and scope of the disclosed subject matter.

What is claimed is:

1. A method of producing human endocrine progenitor cells from pluripotent stem cells comprising:
   (a) incubating pluripotent stem cells (PSCs) in culture medium comprising Wnt3a, Activin A, TGβi, and keratinocyte growth factor (KGF) for 3-7 days;
   (b) exposing the cells resulting from step (a) to medium comprising retinoic acid (RA) for 2-3 days; and
   (c) culturing the cells resulting from step (b) in medium comprising RA, epidermal growth factor (EGF), and KGF,
   thereby producing a culture comprising greater than 70% PDX1$^+$ NKX6.1$^+$ human endocrine progenitor cells.

2. The method of claim 1 wherein incubating step (a) is five days, exposing step (b) is two days, or culturing step (c) is 3-5 days.

3. The method of claim 1 further comprising incubating the culture comprising PDX1$^+$ NKX6.1$^+$ endocrine progenitor cells in medium comprising Alki, T3, γ-secretase inhibitor XXi, LDN-193189, NEAA, N-acetyl Cysteine, zinc sulfate, glutamine supplement, heparin, and vitamin C for at least 8 days, thereby producing INS$^+$ NKX6.1$^+$ GCG$^-$ immature β-like cells.

4. The method of claim 3 further comprising sorting the PDX1$^+$ NKX6.1$^+$ cells in the culture to enrich for INS$^+$ NKX6.1$^+$ GCG$^-$ immature β-like cells.

5. The method of claim 4 further comprising re-aggregating the immature beta-like cells into clusters of about 100-150 μm.

6. The method of claim 5 further comprising culturing the re-aggregated clusters in medium comprising Alki, T3 and low glucose for at least 6 days, thereby producing mature functional beta cells in enhanced beta-clusters (eBCs).

7. The method of claim 6 wherein the eBCs respond to in vivo glucose challenges within three days of transplantation of the cells into a subject.

8. The method of claim 6 wherein culturing of the re-aggregated clusters produces no detectable cell types of exocrine pancreatic lineages.

9. The method of claim 6 wherein at least 95% of the eBC-cells express chromogranin A, or at least 95% of the eBC-cells eBCs stain positive for synaptophysin, or up to 80% of the eBC-cells are monohormonal C-peptide$^+$ cells.

10. The method of claim 6 wherein 80% of the eBC-cells are double positive for C-peptide and NKX6.1.

11. The method of claim 6 wherein the basal oxygen consumption rate of eBCs is more than about 10.799 picomoles of oxygen consumed per minute per nanogram of C-peptide.

12. The method of claim 6 wherein the extracellular acidification rate of eBCs is at most 0.6922 mpH/minute per nanogram of C-peptide.

13. The method of claim 3 further comprising producing beta cells from INS$^+$ NKX6.1$^+$ GCG$^-$ immature β-like cells comprising
   (a) sorting the INS$^+$ NKX6.1$^+$ GCG$^-$ immature β-like cells in a culture to enrich for INS$^+$ NKX6.1$^+$ GCG$^-$ immature β-like cells; and
   (b) re-aggregating the cells into islet-sized clusters by maintaining the self-organized clusters in CMRL containing B27 or FBS, glutamamide supplement, NEAA, Rock inhibitor, ALKi II, vitamin C, T3, N-acetyl cysteine, zinc sulfate and heparin for at least 6 days, thereby producing mature beta cells.

14. The method of claim 6 wherein maturation of beta cells is achieved through activation of mitochondrial oxidative respiration.

* * * * *

UNITED STATES PATENT AND TRADEMARK OFFICE
CERTIFICATE OF CORRECTION

PATENT NO. : 11,299,711 B2
APPLICATION NO. : 16/092166
DATED : April 12, 2022
INVENTOR(S) : Matthias Hebrok et al.

It is certified that error appears in the above-identified patent and that said Letters Patent is hereby corrected as shown below:

In the Claims

At Column 52, Line 48, "95% of the eBC-cells eBCs stain positive" should be -- 95% of the eBC-cells stain positive --.

At Column 52, Line 61, "comprising" should be -- comprising: --.

At Column 52, Line 67, "glutamamide" should be -- glutamine --.

Signed and Sealed this
Eighth Day of November, 2022

Katherine Kelly Vidal
*Director of the United States Patent and Trademark Office*